United States Patent
Liu et al.

(10) Patent No.: US 12,269,816 B2
(45) Date of Patent: Apr. 8, 2025

(54) BENZOTHIOPHENE COMPOUND, PREPARATION METHOD THEREFOR AND USE THEREOF

(71) Applicant: SICHUAN KELUN-BIOTECH BIOPHARMACEUTICAL CO., LTD., Sichuan (CN)

(72) Inventors: Jinming Liu, Sichuan (CN); Yun Ren, Sichuan (CN); Qiang Tian, Sichuan (CN); Hongmei Song, Sichuan (CN); Tongtong Xue, Sichuan (CN); Jingyi Wang, Sichuan (CN)

(73) Assignee: SICHUAN KELUN-BIOTECH BIOPHARMACEUTICAL CO., LTD., Sichuan (CN)

( * ) Notice: Subject to any disclaimer, the term of this patent is extended or adjusted under 35 U.S.C. 154(b) by 892 days.

(21) Appl. No.: 17/435,031

(22) PCT Filed: Apr. 20, 2020

(86) PCT No.: PCT/CN2020/085525
§ 371 (c)(1),
(2) Date: Aug. 30, 2021

(87) PCT Pub. No.: WO2020/221038
PCT Pub. Date: Nov. 5, 2020

(65) Prior Publication Data
US 2022/0162199 A1     May 26, 2022

(30) Foreign Application Priority Data

Apr. 30, 2019 (CN) .......................... 201910359616.0

(51) Int. Cl.
*C07D 409/12* (2006.01)
*C07D 409/14* (2006.01)

(52) U.S. Cl.
CPC ......... *C07D 409/12* (2013.01); *C07D 409/14* (2013.01)

(58) Field of Classification Search
CPC .......................... C07D 409/12; C07D 409/14
See application file for complete search history.

(56) References Cited

U.S. PATENT DOCUMENTS 10,414,747 B2 * 9/2019 Altman .................... A61P 37/04
10,793,557 B2 * 10/2020 Altman ................ C07D 495/04

FOREIGN PATENT DOCUMENTS

| AU | 2016204436 A1 | 7/2016 |
|----|---------------|--------|
| CN | 1835943 A | 9/2006 |

(Continued)

OTHER PUBLICATIONS

Valentino J. Stella, Journal of Pharmaceutical Sciences, vol. 109, Issue 12, 3514-3523, 2020, p. 351 (Year: 2020).*

(Continued)

*Primary Examiner* — Clinton A Brooks
*Assistant Examiner* — Izabela Schmidt
(74) *Attorney, Agent, or Firm* — Rothwell, Figg, Ernst & Manbeck, P.C.

(57) ABSTRACT

A compound represented by formula (I) or a pharmaceutically acceptable salt, a stereoisomer, a tautomer, a polymorph, a solvate, an N-oxide, an isotope labeled compound, a metabolite or a prodrug thereof, a pharmaceutical composition and a pill container comprising same, a preparation method therefor, and the use thereof in the preparation of drugs for preventing or treating STING-mediated related diseases.

(Continued)

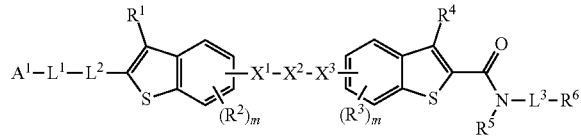

29 Claims, 3 Drawing Sheets

(56) References Cited

FOREIGN PATENT DOCUMENTS

| CN | 109563081 | A | | 4/2019 | |
|---|---|---|---|---|---|
| WO | 2004065380 | A1 | | 8/2004 | |
| WO | 2017175156 | A1 | | 10/2017 | |
| WO | WO-2018067423 | A1 | * | 4/2018 | ........... A61K 31/381 |
| WO | 2018234805 | A1 | | 12/2018 | |
| WO | 2018234807 | A1 | | 12/2018 | |
| WO | 2018234808 | A1 | | 12/2018 | |
| WO | 2019/027857 | A1 | | 2/2019 | |
| WO | 2019027858 | A1 | | 2/2019 | |
| WO | WO-2019069275 | A1 | * | 4/2019 | ......... A61K 31/4184 |
| WO | 2019195124 | A1 | | 10/2019 | |

OTHER PUBLICATIONS

Scott Obach, Pharmacol Rev 65:578-640, Apr. 2013 (Year: 2013).*
Su T, Zhang Y, Valerie K, Wang XY, Lin S, Zhu G. Sting activation in cancer immunotherapy. Theranostics. Oct. 15, 2019;9(25):7759-7771. doi: 10.7150/thno.37574. PMID: 31695799; PMCID: PMC6831454 (Year: 2019).*
International Search Report and Written Opinion issued in corresponding Chinese Application No. PCT/CN2020/085525, dated Jul. 7, 2020, 16 pages, with English translations.
The State Intellectual Property Office of People's Republic of China, First Office Action for CN 202080017726.X with English Translation, Jun. 29, 2023, 14 pages.
Lu Qianying et al., cGAS-STING signaling pathway and diseases, Int. J. Biomed. Eng., Dec. 2016, vol. 30, No. 6, 9 pages.
Extended European Search Report issued for European Application No. 20798155.6 dated Nov. 25, 2022, 8 pages.

* cited by examiner

BENZOTHIOPHENE COMPOUND, PREPARATION METHOD THEREFOR AND USE THEREOF

CROSS-REFERENCE TO RELATED APPLICATION

This application is a 35 U.S.C. 371 National Phase Entry application from PCT/CN2020/085525, filed Apr. 20, 2020, designating the United States, which claims priority under 35 U.S.C. § 119 to Chinese Patent Application No 201910359616.0, filed on Apr. 30, 2019, the disclosures of which are incorporated by reference in their entirety.

FIELD OF THE INVENTION

The present invention relates to a benzothiophene compound, a pharmaceutical composition and a kit comprising the same, a method for preparing the same, and use thereof in the manufacture of a medicament for treating a STING-mediated disease.

BACKGROUND OF THE INVENTION

STING (stimulator of interferon gene), also referred to as TMEM173, MPYS, MITA or ERIS, is an important signaling molecule in the immune response. When STING is stimulated and activated by a ligand (such as cyclic dinucleotide (CDN) derived from bacteria), it will up-regulate the IRF3 and NF-κB signaling pathways.

Specifically, activated STING recruits TANK-binding kinase (TBK1) in the cytoplasm and mediates the phosphorylation of IRF3 by TBK1, leading to the generation of interferons and other cytokines. Interferon is a group of active proteins with multiple functions, including regulating the immune function, enhancing the vaccine effect, acting against viruses, inhibiting the proliferation of tumor cells, inducing the apoptosis of tumor cells, etc. (Nature, 2008, 455, 674-678; Science Signaling, 2012, 5, ra20). In addition, STING protein also participates in various pathological and physiological processes such as tumor immunity, autoimmune inflammation, autophagy, etc. The STING-mediated type I interferon signaling pathway is a key step for activation of tumor-specific T cells and infiltration of tumor-infiltrating lymphocytes. Low expression of STING in many tumor tissues such as hepatocellular carcinoma, gastric cancer and colorectal cancer promotes the occurrence of tumor immune tolerance and/or immune escape. A large number of studies have shown that STING agonists have significant anti-tumor activity. For example, in a mouse model, a STING agonist (ADU-S100) can inhibit the growth of a secondary inoculated and transplanted tumor, reverse the immune tolerance against the tumor for a long time, and inhibit the recurrence of the tumor.

Currently, the disclosed STING agonists are mainly compounds with cyclic dinucleotide analog structures. For example, MIW815 (ADU-S100) has entered clinical phase 1,

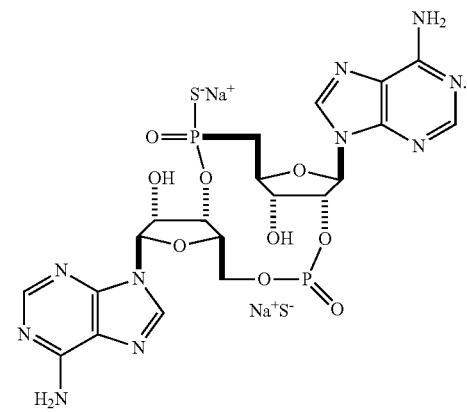

ADU-S100

In addition, research institutions have successively disclosed STING agonists with non-cyclic dinucleotide structures. WO2018067423 discloses a class of benzothiophene compounds as STING agonists for the treatment of diseases related to cell proliferation (such as cancers). WO2018234805, WO2018234807 and WO2018234808 also disclose a class of heterocyclic compounds, which can modulate or activate human STING proteins for the treatment of various diseases (including cancers).

Therefore, STING agonists have good application prospects as drugs in the pharmaceutical industry. In order to achieve better therapeutic effects on tumors and better meet the market demand, it is urgent to develop new and efficient STING agonists.

SUMMARY OF THE INVENTION

An aspect of the present invention provides a class of benzothiophene compounds, which have a strong agonistic effect on the STING signal pathway, and therefore a better therapeutic effect on tumors. The compound of the present invention also has various excellent properties, such as good physicochemical properties (e.g., solubility, physical and/or chemical stability) and good safety.

The compound is a compound of formula I:

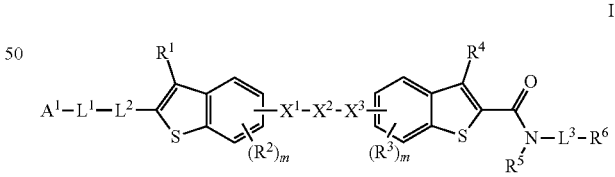

I wherein $X^1$ and $X^3$ are the same or different, and are each independently selected from the group consisting of a covalent bond, —O—, —S— and —NR$^a$—;

$X^2$ is selected from the group consisting of $C_{1-6}$ alkylene, $C_{2-6}$ alkenylene, $C_{2-6}$ alkynylene, $C_{3-6}$ cycloalkyl, 3-6 membered heterocyclyl, $C_{1-6}$ alkylene-$X^4$ and $C_{1-6}$ alkylene-$X^4$—$C_{1-6}$ alkylene, wherein the $C_{1-6}$ alkylene, $C_{2-6}$ alkenylene, $C_{2-6}$ alkynylene, $C_{3-6}$ cycloalkyl and 3-6 membered heterocyclyl are each optionally substituted with one or more substituents independently selected from the group consisting of halogen, cyano, hydroxy, $C_{1-6}$ alkyl and $C_{1-6}$ alkoxy;

$X^4$ is selected from the group consisting of —O—, —S—, —NR$^a$—, —C(O)—, —C(O)—NR$^a$—, —S(O)—, —S(O)$_2$—, —S(O)$_2$—NR$^a$—, —O—C(O)—NR$^a$—, —NR$^a$—C(O)—NR$^a$— and —NR$^a$—S(O)$_2$—NR$^a$;

$L^1$ is selected from the group consisting of a covalent bond and —(C(R$^8$)$_2$)$_p$—;

$L^2$ is selected from the group consisting of a covalent bond and —C(O)—;

$L^3$ is selected from the group consisting of a covalent bond and —(C(R$^9$)$_2$)$_q$—;

$A^1$ is selected from the group consisting of H, cyano. —OR$^a$, —SR$^a$, —S(O)R$^a$, —S(O)$_2$R$^a$, —NR$^a$R$^b$, —C(O)—OR$^a$, —O—C(O)—R$^a$, —C(O)—NR$^a$R$^b$, —NR$^a$—C(O)—R$^a$, —S(O)$_2$—NR$^a$R$^b$, —NR$^a$—S(O)$_2$—R$^a$, —O—C(O)—NR$^a$R$^b$, —NR$^a$—C(O)—OR$^a$, —NR$^a$—C(O)—NR$^a$R$^b$, —NR$^a$—S(O)$_2$—NR$^a$R$^b$, $C_{1-6}$ alkyl, $C_{2-6}$ alkenyl, $C_{2-6}$ alkynyl, $C_{3-6}$ cycloalkyl, 3-6 membered heterocyclyl, $C_{6-10}$ aryl and 5-10 membered heteroaryl, wherein the $C_{3-6}$ cycloalkyl, 3-6 membered heterocyclyl, $C_{6-10}$ aryl and 5-10 membered heteroaryl are each optionally substituted with one or more substituents independently selected from the group consisting of halogen. $C_{1-6}$ alkyl, $C_{1-6}$, haloalkyl, cyano, hydroxy and $C_{1-6}$, alkoxy;

$R^1$ and $R^4$ are the same or different, and are each independently selected from the group consisting of H, halogen, cyano, —OR$^a$, —NR$^a$R$^b$, $C_{1-6}$ alkyl, $C_{3-6}$ cycloalkyl, and 3-6 membered heterocyclyl, wherein the $C_{1-6}$ alkyl, $C_{3-6}$ cycloalkyl, and 3-6 membered heterocyclyl are each optionally substituted with one or more substituents independently selected from the group consisting of halogen, $C_{1-6}$ alkyl, $C_{1-6}$ haloalkyl, cyano, hydroxy and $C_{1-6}$ alkoxy;

$R^2$ and $R^3$ are the same or different, and are each independently selected from the group consisting of H, halogen, cyano, —OR$^a$, —SR, —S(O)R$^a$, —S(O)$_2$R$^a$, —NR$^a$R$^b$, —C(O)—NR$^a$R$^b$, —NR$^a$—C(O)—R$^a$, $C_{1-6}$ alkyl, $C_{2-6}$ alkenyl, $C_{2-6}$ alkynyl, $C_{3-6}$ cycloalkyl, 3-6 membered heterocyclyl, $C_{6-10}$ aryl and 5-10 membered heteroaryl, wherein the $C_{1-6}$ alkyl, $C_{2-6}$ alkenyl, $C_{2-6}$ alkynyl, $C_{3-6}$ cycloalkyl, 3-6 membered heterocyclyl, $C_{6-10}$ aryl and 5-10 membered heteroaryl are each optionally substituted with one or more substituents independently selected from the group consisting of halogen. $C_{1-6}$ alkyl, $C_{1-6}$ haloalkyl, cyano, hydroxy and $C_{1-6}$ alkoxy;

$R^5$ is selected from the group consisting of H, $C_{1-6}$ alkyl, $C_{3-10}$ cycloalkyl and 3-10 membered heterocyclyl, wherein the $C_{1-6}$ alkyl, $C_{3-10}$ cycloalkyl and 3-10 membered heterocyclyl are each optionally substituted with one or more substituents independently selected from the group consisting of halogen, cyano, hydroxy, $C_{1-6}$ alkyl, $C_{3-10}$ cycloalkyl, 3-10 membered heterocyclyl. $C_{1-6}$ haloalkyl, $C_{1-6}$ alkoxy, $C_{1-6}$ haloalkoxy, —NR$^a$R$^b$, —CO$_2$R$^a$ and —S(O)$_2$R$^a$;

$R^6$ is selected from the group consisting of H, $C_{1-6}$ alkyl, $C_{3-10}$ cycloalkyl, 3-10 membered heterocyclyl, $C_{6-10}$ aryl, 5-10 membered heteroaryl, —OR$^a$ and —C(O)$_2$ R$^7$, wherein the $C_{1-6}$ alkyl, $C_{3-10}$ cycloalkyl, 3-10 membered heterocyclyl, $C_{6-10}$ aryl and 5-10 membered heteroaryl are optionally substituted with one or more R$^c$;

R$^c$ is each independently selected from the group consisting of halogen, cyano, hydroxy, —NR$^a$R$^b$, —C(O)$_2$— R$^1$, $C_{1-6}$ alkyl, $C_{1-6}$ alkoxy and $C_{1-6}$ haloalkoxy, wherein the $C_{1-6}$ alkyl, $C_{1-6}$ alkoxy and $C_{1-6}$ haloalkoxy are each optionally substituted with one or more substituents independently selected from the group consisting of cyano, —OR$^a$, —NR$^a$R$^b$, —C(O)$_2$—R$^a$, $C_{1-6}$ alkoxy and —SO$_2$R$^a$;

$R^7$ is selected from the group consisting of H, $C_{1-6}$ alkyl, $C_{3-10}$ cycloalkyl and 3-10 membered heterocyclyl, wherein the $C_{1-6}$ alkyl, $C_{3-10}$ cycloalkyl and 3-10 membered heterocyclyl are each optionally substituted with one or more substituents independently selected from the group consisting of halogen, cyano, hydroxy, 3-10 membered heterocyclyl. —NR$^a$R$^b$, —C(O)$_2$—R$^a$, $C_{1-6}$ alkoxy and —SO$_2$R$^a$;

$R^8$ is each independently selected from the group consisting of H, halogen, cyano, —OR$^a$, —SR$^a$, —NR$^a$R$^b$, $C_{1-6}$ alkyl, $C_{2-6}$ alkenyl, $C_{2-6}$ alkynyl, $C_{3-6}$ cycloalkyl, 3-6 membered heterocyclyl, $C_{6-10}$ aryl and 5-10 membered heteroaryl, wherein the $C_{1-6}$ alkyl, $C_{2-6}$ alkenyl, $C_{2-6}$ alkynyl, $C_{3-6}$ cycloalkyl, 3-6 membered heterocyclyl, $C_{6-10}$ aryl and 5-10 membered heteroaryl are each optionally substituted with one or more substituents independently selected from the group consisting of halogen, $C_{1-6}$ alkyl, $C_{1-6}$ haloalkyl, cyano, hydroxy, $C_{3-6}$ cycloalkyl, 3-6 membered heterocyclyl, $C_{6-10}$ aryl, 5-10 membered heteroaryl, $C_{1-6}$ alkoxy and —OR$^a$; or two R$^b$ on different carbon atoms are taken together with the carbon atoms between them to form a $C_{3-6}$ cycloalkyl or a 3-6 membered heterocyclyl; or two R$^8$ on the same carbon atom are taken together with the carbon atom to which they are bonded to form a $C_{3-6}$ cycloalkyl or a 3-6 membered heterocyclyl;

$R^9$ is each independently selected from the group consisting of H, halogen, cyano, —OR$^a$, —SR$^a$, —NR$^a$R$^b$, $C_{1-6}$ alkyl, $C_{2-6}$ alkenyl, $C_{2-6}$ alkynyl, $C_{3-6}$ cycloalkyl, 3-6 membered heterocyclyl, $C_{6-10}$ aryl and 5-10 membered heteroaryl, wherein the $C_{1-6}$ alkyl, $C_{2-6}$ alkenyl, $C_{2-6}$ alkynyl, $C_{3-6}$ cycloalkyl, 3-6 membered heterocyclyl, $C_{6-10}$ aryl and 5-10 membered heteroaryl are each optionally substituted with one or more substituents independently selected from the group consisting of halogen, $C_{1-6}$ alkyl, $C_{1-6}$ haloalkyl, cyano, hydroxy, $C_{3-6}$ cycloalkyl, 3-6 membered heterocyclyl, $C_{6-10}$ aryl, 5-10 membered heteroaryl, $C_{1-6}$ alkoxy and —OR$^a$; or two R$^9$ are taken together with the carbon atom to which they are bonded to form a $C_{3-10}$ cycloalkyl or a 3-10 membered heterocyclyl; or any R$^9$ and R$^5$ are taken together with the atoms between them to form a 3-10 membered heterocyclyl;

R$^a$ and R$^b$ are each independently selected from the group consisting of H, $C_{1-6}$ alkyl, $C_{3-6}$ cycloalkyl and $C_{1-6}$ alkoxy, wherein the $C_{1-6}$ alkyl, $C_{3-6}$ cycloalkyl and $C_{1-6}$ alkoxy are each optionally substituted with one or more substituents independently selected from the group consisting of hydroxy, halogen and $C_{1-6}$ alkyl; or R$^a$ and R$^b$ are taken together with the nitrogen atom to which they are bonded to form a 3-7 membered heterocyclyl;

m and n are each independently selected from the group consisting of 0, 1, 2 and 3; and p and q are each independently selected from the group consisting of 1, 2, and 3, or a pharmaceutically acceptable salt, a stereoisomer, a tautomer, a polymorph, a solvate, an N-oxide, an isotope-labeled compound, a metabolite or a prodrug thereof.

Another aspect of the present invention provides a pharmaceutical composition comprising a prophylactically or therapeutically effective amount of the compound of the present invention, or a pharmaceutically acceptable salt, a stereoisomer, a tautomer, a polymorph, a solvate, an N-oxide, an isotope-labeled compound, a metabolite or a prodrug thereof, and one or more pharmaceutically acceptable carriers.

Another aspect of the present invention provides a kit comprising the compound of the present invention, or a pharmaceutically acceptable salt, a stereoisomer, a tautomer, a polymorph, a solvate, an N-oxide, an isotope-labeled compound, a metabolite or a prodrug thereof, or the pharmaceutical composition of the present invention.

Another aspect of the present invention provides use of the compound of the present invention, or a pharmaceutically acceptable salt, a stereoisomer, a tautomer, a polymorph, a solvate, an N-oxide, an isotope-labeled compound, a metabolite or a prodrug thereof for activating the STING signal pathway.

Another aspect of the present invention provides use of the compound of the present invention, or a pharmaceutically acceptable salt, a stereoisomer, a tautomer, a polymorph, a solvate, an N-oxide, an isotope-labeled compound, a metabolite or a prodrug thereof, or the pharmaceutical composition of the present invention for the prophylaxis or treatment of a STING-mediated disease.

Another aspect of the present invention provides use of the compound of the present invention, or a pharmaceutically acceptable salt, a stereoisomer, a tautomer, a polymorph, a solvate, an N-oxide, an isotope-labeled compound, a metabolite or a prodrug thereof, or the pharmaceutical composition of the present invention in the manufacture of a medicament for the prophylaxis or treatment of a STING-mediated disease.

Another aspect of the present invention provides a method for the prophylaxis or treatment of a STING-mediated disease, comprising administering to a subject in need thereof a prophylactically or therapeutically effective amount of the compound of the present invention, or a pharmaceutically acceptable salt, a stereoisomer, a tautomer, a polymorph, a solvate, an N-oxide, an isotope-labeled compound, a metabolite or a prodrug thereof, or the pharmaceutical composition of the present invention.

Another aspect of the present invention provides a method for preparing the compound of the present invention.

DETAILED DESCRIPTION OF THE INVENTION

Definition

Figure 1:
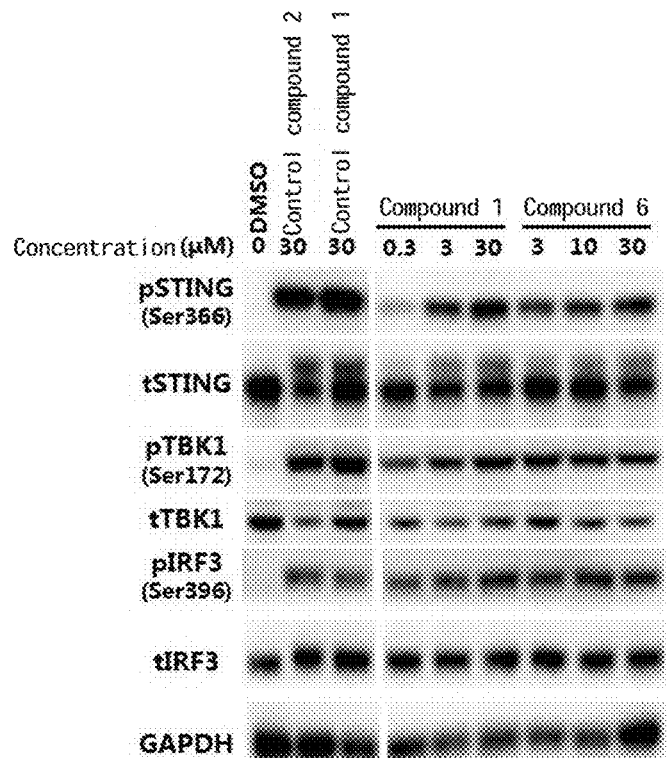
FIG. 1 is a graph showing the experimental results of Western blotting of STING signaling pathway proteins in human THP-1 cells using compounds 1 and 6.
Figure 2:
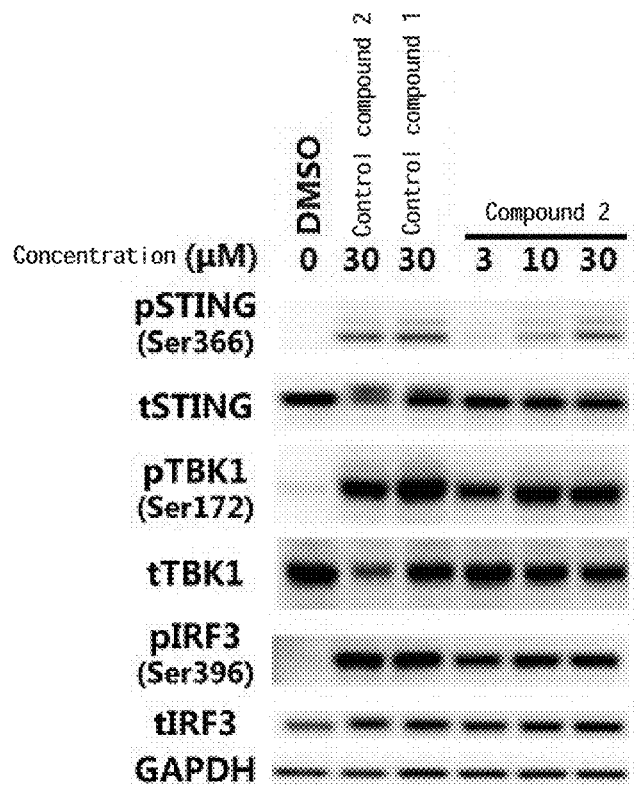
FIG. 2 is a graph showing the experimental results of Western blotting of STING signaling pathway proteins in human THP-1 cells using compound 2.
Figure 3:
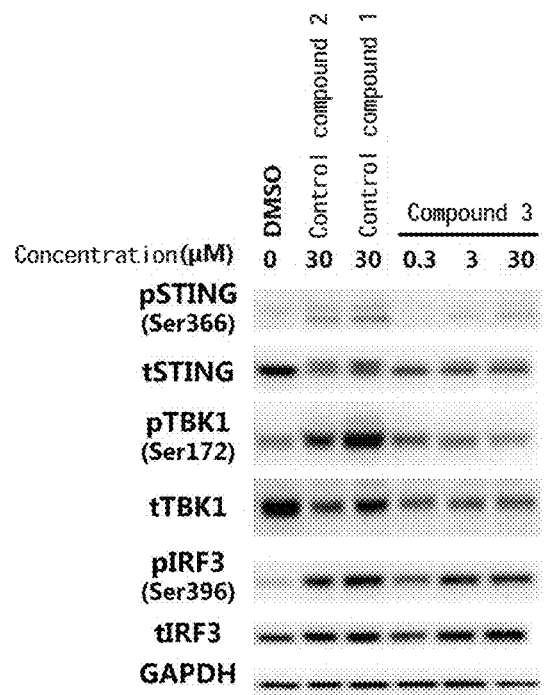
FIG. 3 is a graph showing the experimental results of Western blotting of STING signaling pathway proteins in human THP-1 cells using compound 3.
Figure 4:
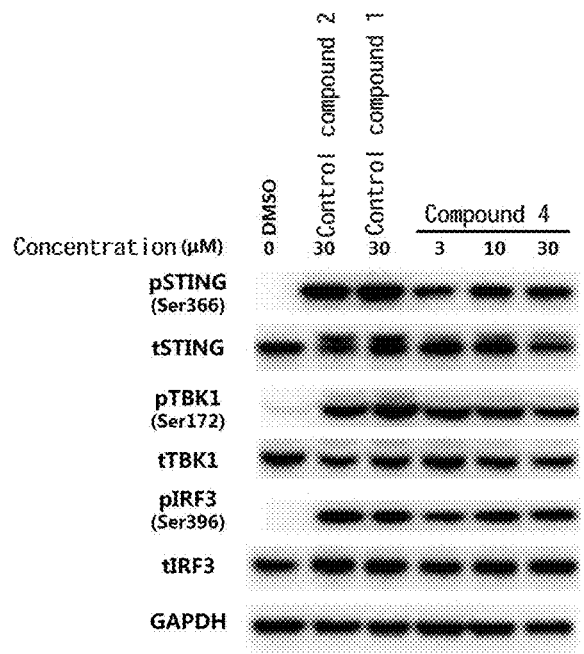
FIG. 4 is a graph showing the experimental results of Western blotting of STING signaling pathway proteins in human THP-1 cells using compound 4.
Figure 5:
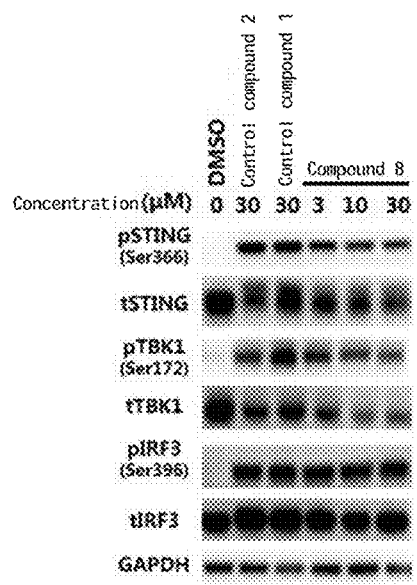
FIG. 5 is a graph showing the experimental results of Western blotting of STING signaling pathway proteins in human THP-1 cells using compound 8.

Unless otherwise defined below, all technical and scientific terms used herein are intended to have the same meanings as those commonly understood by a person skilled in the art. References to techniques employed herein are intended to refer to the techniques as commonly understood in the art, including variations on those techniques or substitutions of equivalent techniques which would be apparent to a person skilled in the art. While it is believed that most of the following terms will be readily understood by a person skilled in the art, the following definitions are put forth to better illustrate the present invention.

The terms "include", "comprise", "have", "contain", or "involve", as well as other variations used herein are inclusive or open-ended, and do not exclude additional, unrecited elements or method steps.

As used herein, the term "alkyl" refers to a linear or branched, saturated aliphatic hydrocarbon residue. For example, as used herein, the term "$C_{1-6}$ alkyl" refers to a linear or branched alkyl group containing 1 to 6 carbon atoms, such as methyl, ethyl, n-propyl, isopropyl, n-butyl, isobutyl, sec-butyl, tert-butyl, n-pentyl or n-hexyl, optionally substituted with one or more (e.g., 1 to 3) suitable substituents, such as halogen.

As used herein, the term "alkylene" refers to a linear or branched divalent alkyl.

As used herein, the term "cycloalkyl" refers to a saturated or partially unsaturated, non-aromatic, monocyclic or polycyclic (such as bicyclic) hydrocarbon ring (e.g. a monocyclic hydrocarbon ring, such as cyclopropyl, cyclobutyl, cyclopentyl, cyclohexyl, cycloheptyl, cyclooctyl or cyclononyl; or a bicyclic hydrocarbon ring, including spiro, fused or bridged ring systems (such as bicyclo[1.1.1]pentyl, bicyclo[2.2.1]heptyl, bicyclo[3.2.1]octyl, bicyclo[5.2.0]nonyl, decahydronaphthyl, etc.)), optionally substituted with one or more (e.g., 1 to 3) suitable substituents. For example, the term "$C_{3-6}$cycloalkyl" refers to a saturated or partially unsaturated, non-aromatic, monocyclic or polycyclic (such as bicyclic) hydrocarbon ring containing 3 to 6 ring-forming carbon atoms, (e.g., cyclopropyl, cyclobutyl, cyclopentyl or cyclohexyl), optionally substituted with one or more (e.g., 1 to 3) suitable substituents, such as methyl-substituted cyclopropyl.

As used herein, the term "alkoxy" means a group obtained by inserting an oxygen atom at any suitable position in an alkyl group (as defined above), such as $C_{1-8}$ alkoxy, $C_{1-6}$ alkoxy, $C_{1-4}$ alkoxy or $C_{1-3}$ alkoxy. Representative examples of the $C_{1-6}$ alkoxy group include, but are not limited to, methoxy, ethoxy, n-propoxy, isopropoxy, n-butoxy, isobutoxy, t-butoxy, pentoxy, hexyloxy, etc., and the alkoxy group is optionally substituted with one or more (e.g., 1 to 3) the same or different substituents.

As used herein, the term "halo" or "halogen" is defined to include fluorine, chlorine, bromine or iodine.

As used herein, the term "haloalkyl" refers to an alkyl substituted with one or more (e.g., 1 to 3) the same or different halogen atoms. For example, the term "$C_{1-6}$ haloalkyl" refers to a haloalkyl having 1 to 6 carbon atoms, such as —CF$_3$, —C$_2$F$_5$, —CHF$_2$, —CH$_2$F, —CH$_2$CF$_3$, —CH$_2$Cl or —CH$_2$CH$_2$CF$_3$, and the like.

As used herein, the term "heterocyclyl" refers to a saturated or partially unsaturated monocyclic or polycyclic group having, for example, 2, 3, 4, 5, 6, 7, 8 or 9 carbon atoms and one or more (e.g., 1, 2, 3 or 4) heteroatoms independently selected from the group consisting of N, O and S(O)$_p$ (wherein p is 0, 1 or 2) in the ring, such as 3-10 membered heterocyclyl, 3-7 membered heterocyclyl, 3-6 membered heterocyclyl, 5-6 membered heterocyclyl, and the like. Representative examples of heterocyclyl include, but are not limited to, oxiranyl, aziridinyl, azetidinyl, oxetanyl, tetrahydrofuranyl, pyrrolidinyl, pyrrolidinonyl, imidazolidinyl, pyrazolidinyl, tetrahydropyranyl, piperidinyl, morpholinyl, dithianyl, thiomorpholinyl, piperazinyl, trithianyl, and the like.

As used herein, the term "aryl" or "aromatic ring" refers to an all-carbon monocyclic or fused polycyclic aromatic group having a conjugated n electron system. For example, the term "C$_{6-10}$ aryl" or "C$_{6-10}$ aromatic ring" refers to an aromatic group containing 6 to 10 carbon atoms, such as phenyl (ring) or naphthyl (ring). The aryl group is optionally substituted with one or more (e.g., 1 to 3) suitable substituents (e.g. halogen, —OH, —CN, —NO$_2$, C$_{1-6}$ alkyl, and the like).

As used herein, the term "heteroaryl" or "heteroaromatic ring" refers to a monocyclic, bicyclic or tricyclic aromatic ring system having, for example, 5, 6, 8, 9, 10, 11, 12, 13 or 14 ring atoms, particularly 1 or 2 or 3 or 4 or 5 or 6 or 9 or 10 carbon atoms, and at least one heteroatom selected from the group consisting of N, O and S, and in each case it may be benzo-fused. For example, a heteroaryl or a heteroaromatic ring can be selected from the group consisting of thienyl (ring), furyl (ring), pyrrolyl (ring), oxazolyl (ring), thiazolyl (ring), imidazolyl (ring), pyrazolyl (ring), isoxazolyl (ring), isothiazolyl (ring), oxadiazolyl (ring), triazolyl (ring), thiadiazolyl (ring), and benzo derivatives thereof; or pyridyl (ring), pyridazinyl (ring), pyrimidinyl (ring), pyrazinyl (ring), triazinyl (ring), and benzo derivatives thereof.

The term "substituted" means that one or more (e.g., one, two, three, or four) hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

If a substituent is described as being "optionally substituted with . . . ", the substituent may be either (1) not substituted, or (2) substituted. If a carbon of a substituent is described as being optionally substituted with one or more of a list of substituents, one or more of the hydrogens on the carbon (to the extent there are any) may or may not separately and/or together be replaced with an independently selected optional substituent. If a nitrogen of a substituent is described as being optionally substituted with one or more of a list of substituents, one or more of the hydrogens on the nitrogen (to the extent there are any) may or may not each be replaced with an independently selected optional substituent.

If substituents are described as being "independently selected" from a group, each substituent is selected independent of the other(s). Each substituent therefore may be identical to or different from the other substituent(s).

As used herein, the term "one or more" means one or more than one (e.g., 2, 3, 4, 5, 6, 7, 8, 9 or 10) as reasonable.

As used herein, unless specified, the point of attachment of a substituent can be from any suitable position of the substituent.

When a bond to a substituent is shown to cross a bond connecting two atoms in a ring, then such substituent may be bonded to any of the ring-forming atoms in that ring that are substitutable.

The present invention also includes all pharmaceutically acceptable isotopically labeled compounds, which are identical to those of the present invention except that one or more atoms are replaced by an atom having the same atomic number, but an atomic mass or mass number different from the atomic mass or mass number which predominates in nature. Examples of isotopes suitable for inclusion in the compound of the present invention include, but are not limited to, isotopes of hydrogen, such as $^2$H (D), and $^3$H (T); carbon, such as $^{11}$C, $^{13}$C, and $^{14}$C; chlorine, such as $^{37}$Cl; fluorine, such as $^{18}$F; iodine, such as $^{123}$I and $^{125}$I; nitrogen, such as $^{13}$N and $^{15}$N; oxygen, such as $^{15}$O, $^{17}$O, and $^{18}$O; phosphorus, such as $^{32}$P; and sulfur, such as $^{35}$S. Certain isotopically labeled compounds of the present invention, for example those incorporating a radioactive isotope, are useful in drug and/or substrate tissue distribution studies (e.g., assays). The radioactive isotopes tritium, i.e., $^3$H, and carbon-14. i.e., $^{14}$C, are particularly useful for this purpose in view of their ease of incorporation and ready means of detection. Substitution with positron-emitting isotopes, such as $^{11}$C, $^{18}$F, $^{15}$O and $^{13}$N, can be useful in positron emission tomography (PET) studies for examining substrate receptor occupancy. Isotopically labeled compounds of the present invention can generally be prepared by processes analogous to those described in the accompanying Schemes and/or in the Examples and Preparations, by using an appropriate isotopically labeled reagent in place of the non-labeled reagent previously employed. Pharmaceutically acceptable solvates in accordance with the invention include those wherein the solvent of crystallization may be isotopically substituted, e.g., D$_2$O, acetone-d$_6$, or DMSO-d$_6$.

The term "stereoisomer" refers to isomers formed due to the presence of at least one asymmetric center. For a compound having one or more (e.g., 1, 2, 3 or 4) asymmetric centers, racemic mixtures, single enantiomers, diastereomeric mixtures and individual diastereomers can be formed. Certain molecules may also have geometric isomers (cis/trans). Similarly, the compound of the present invention may exist as a mixture of two or more forms having different structures in rapid equilibrium (often referred to as tautomers). Representative examples of tautomers include ketone-enol tautomers, phenol-ketone tautomers, nitroso-oxime tautomers, imine-enamine tautomers, etc. It is understood that the present application cover all isomers in any percentage (e.g., 60%, 65%, 70%, 75%, 80%, 85%, 90%, 95%, 96%, 97%, 98%, 99%) or mixtures thereof.

The present invention includes all possible crystalline forms or polymorphs of the compound of the present invention, either as a single polymorph, or as a mixture of more than one polymorph, in any ratio.

It also should be understood that, certain compounds of the present invention can be used for the treatment in a free form, or where appropriate, in a form of a pharmaceutically acceptable derivative. In the present invention, the pharmaceutically acceptable derivative includes, but is not limited to a pharmaceutically acceptable salt, solvate, metabolite or prodrug, which can directly or indirectly provide the compound of the present invention or a metabolite or residue thereof after being administered to a patient in need thereof. Therefore, "the compound of the present invention" mentioned herein also means to encompass various derivative forms of the compound as mentioned above.

A pharmaceutically acceptable salt of the compound of the present invention includes an acid addition salt and a base addition salt. A suitable acid addition salt is formed from an acid which forms a pharmaceutically acceptable salt. A suitable base addition salt is formed from a base which forms a pharmaceutically acceptable salt. For a review on suitable salts, see "Handbook of Pharmaceutical Salts: Properties, Selection, and Use" by Stahl and Wermuth (Wiley-VCH, 2002). Methods for preparing a pharmaceutically acceptable salt of the compound of the present invention are known to those skilled in the art.

The compound of the present invention can exist as a solvate (preferably a hydrate), wherein the compound of the present invention contains a polar solvent, in particular water, methanol or ethanol for example, as a structural element of the crystal lattice of the compound. The amount of the polar solvent, in particular water, may exist in a stoichiometric or non-stoichiometric ratio.

As can be appreciated by a person skilled in the art, not all nitrogen containing heterocycles can form N-oxides since the nitrogen requires an available lone-pair electron for oxidation to the oxide. A person skilled in the art will recognize those nitrogen containing heterocycles which can form N-oxides. A person skilled in the art will also recognize that tertiary amines can form N-oxides. Synthetic methods for the preparation of N-oxides of heterocycles and tertiary amines are well known to a person skilled in the art, and they include, but are not limited to, the oxidation of heterocycles and tertiary amines with peroxy acids such as peracetic acid and m-chloroperbenzoic acid (MCPBA), hydrogen peroxide, alkyl hydroperoxides such as tert-butyl hydroperoxide, sodium perborate, and dioxiranes such as dimethyldioxirane. These methods for the preparation of N-oxides have been extensively described and reviewed in literatures, see e.g., T. L. Gilchrist, *Comprehensive Organic Synthesis*, vol. 7, pp 748-750; A. R. Katritzky and A. J. Boulton, Eds., Academic Press; and G W. H. Cheeseman and E. S. G. Werstiuk, Advances in *Heterocyclic Chemistry*, vol. 22, pp 390-392, A. R. Katritzky and A. J. Boulton, Eds., Academic Press.

The metabolite of the compound of the present invention, namely a substance formed in vivo upon administration of the compound of the present invention, is also included within the scope of the present invention. Such a product may result e.g., from the oxidation, reduction, hydrolysis, amidation, de-amidation, esterification, enzymolysis, and the like, of the administered compound. Accordingly, the present invention encompasses the metabolite of the compound of the present invention, including a compound produced by a method comprising contacting the compound of the present invention with a mammal for a period of time sufficient to result in a metabolic product thereof.

Also within the scope of the present invention is a prodrug of the compound of the invention, which is a certain derivative of the compound of the invention that may have little or no pharmacological activity itself, but can, when administered into or onto the body, be converted into the compound of the invention having the desired activity, for example, by hydrolytic cleavage. In general, such prodrug will be a functional derivative of the compound which is readily converted in vivo into the compound with desired therapeutic activity. Further information on the use of the prodrug may be found in "Pro-drugs as Novel Delivery Systems". Vol. 14, ACS Symposium Series (T. Higuchi and V. Stella) and "Bioreversible Carriers in Drug Design", Pergamon Press, 1987 (edited by E. B. Roche, American Pharmaceutical Association). The prodrug in accordance with the invention can, for example, be produced by replacing appropriate functionalities present in the compound of the present invention with certain moieties known to those skilled in the art as "pro-moieties" as described, for example, in "Design of Prodrugs" by H. Bundgaard (Elsevier, 1985).

The present invention further encompasses the compound of the present invention having a protecting group. During any of the processes for preparation of the compound of the present invention, it may be necessary and/or desirable to protect sensitive or reactive groups on any of the molecules concerned, thereby resulting in the chemically protected form of the compound of the present invention. This may be achieved by means of conventional protecting groups, e.g., those described in Protective Groups in Organic Chemistry, ed. J. F. W. McOmie, Plenum Press, 1973 and T. W. Greene & P. G. M. Wuts, Protective Groups in Organic Synthesis, John Wiley & Sons, 1991, which are incorporated herein by reference. The protecting groups may be removed at a convenient subsequent stage using methods known from the art.

The term "about" refers to a range within ±10%, preferably within +5%, and more preferably within ±2% of the specified value.

Compound

One object of the present invention is to provide a compound of formula (I):

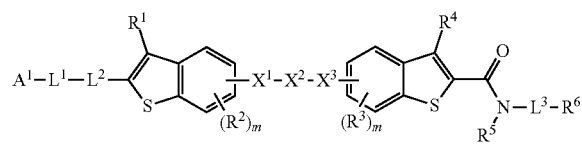

wherein $X^1$ and $X^3$ are the same or different, and are each independently selected from the group consisting of a covalent bond, —O—, —S— and —NR$^a$—;

$X^2$ is selected from the group consisting of $C_{1-6}$ alkylene, $C_{2-6}$ alkenylene, $C_{2-6}$ alkynylene, $C_{3-6}$ cycloalkyl, 3-6 membered heterocyclyl, $C_{1-6}$ alkylene-$X^4$ and $C_{1-6}$ alkylene-$X^4$—$C_{1-6}$ alkylene, wherein the $C_{1-6}$ alkylene, $C_{2-6}$ alkenylene, $C_{2-6}$ alkynylene, $C_{3-6}$ cycloalkyl and 3-6 membered heterocyclyl are each optionally substituted with one or more substituents independently selected from the group consisting of halogen, cyano, hydroxy, $C_{1-6}$ alkyl and $C_{1-6}$ alkoxy;

$X^4$ is selected from the group consisting of —O—, —S—, —NR$^a$—, —C(O)—, —C(O)—NR$^a$—, —S(O)—, —S(O)$_2$—, —S(O)$_2$—NR$^a$—, —O—C(O)—NR$^a$—, —NR$^a$—C(O)—NR$^a$— and —NR$^a$—S(O)$_2$—NR$^a$—;

$L^1$ is selected from the group consisting of a covalent bond and —(C(R$^8$)$_2$)$_p$—;

$L^2$ is selected from the group consisting of a covalent bond and —C(O)—;

$L^3$ is selected from the group consisting of a covalent bond and —(C(R$^9$)$_2$)$_q$—;

$A^1$ is selected from the group consisting of H, cyano, —OR$^a$, —SR$^a$, —S(O)R$^a$, —S(O)$_2$R$^a$, —NR$^a$R$^b$, —C(O)—OR$^a$, —O—C(O)—R$^a$, —C(O)—NR$^a$R$^b$, —NR$^a$—C(O)—R$^a$, —S(O)$_2$—NR$^a$R$^b$, —NR$^a$—

$S(O)_2$—$R^a$, —O—C(O)—$NR^aR^b$, —$NR^a$—C(O)—$OR^a$, —$NR^a$—C(O)—$NR^aR^b$, —$NR^a$—$S(O)_2$—$NR^aR^b$, $C_{1-6}$ alkyl, $C_{2-6}$ alkenyl, $C_{2-6}$ alkynyl, $C_{3-6}$ cycloalkyl, 3-6 membered heterocyclyl, $C_{6-10}$ aryl and 5-10 membered heteroaryl, wherein the $C_{3-6}$ cycloalkyl, 3-6 membered heterocyclyl, $C_{6-10}$ aryl and 5-10 membered heteroaryl are each optionally substituted with one or more substituents independently selected from the group consisting of halogen, $C_{1-6}$ alkyl, $C_{1-6}$ haloalkyl, cyano, hydroxy and $C_{1-6}$ alkoxy;

$R^1$ and $R^4$ are the same or different, and are each independently selected from the group consisting of H, halogen, cyano, —$OR^a$, —$NR^aR^b$, $C_{1-6}$ alkyl, $C_{3-6}$ cycloalkyl, and 3-6 membered heterocyclyl, wherein the $C_{1-6}$ alkyl, $C_{3-6}$ cycloalkyl, and 3-6 membered heterocyclyl are each optionally substituted with one or more substituents independently selected from the group consisting of halogen, $C_{1-6}$ alkyl, $C_{1-6}$ haloalkyl, cyano, hydroxy and $C_{1-6}$ alkoxy;

$R^2$ and $R^3$ are the same or different, and are each independently selected from the group consisting of H, halogen, cyano, —$OR^a$, —$SR^a$, —$S(O)R^a$, —$S(O)_2R^a$, —$NR^aR^b$, —C(O)—$NR^aR^b$, —$NR^a$—C(O)—$R^a$, $C_{1-6}$ alkyl, $C_{2-6}$ alkenyl, $C_{2-6}$ alkynyl, $C_{3-6}$ cycloalkyl, 3-6 membered heterocyclyl, $C_{6-10}$ aryl and 5-10 membered heteroaryl, wherein the $C_{1-6}$ alkyl, $C_{2-6}$ alkenyl, $C_{2-6}$ alkynyl, $C_{3-6}$ cycloalkyl, 3-6 membered heterocyclyl, $C_{6-10}$ aryl and 5-10 membered heteroaryl are each optionally substituted with one or more substituents independently selected from the group consisting of halogen, $C_{1-6}$ alkyl, $C_{1-6}$ haloalkyl, cyano, hydroxy and $C_{1-6}$ alkoxy;

$R^5$ is selected from the group consisting of H, $C_{1-6}$ alkyl, $C_{3-10}$ cycloalkyl and 3-10 membered heterocyclyl, wherein the $C_{1-6}$ alkyl, $C_{3-10}$ cycloalkyl and 3-10 membered heterocyclyl are each optionally substituted with one or more substituents independently selected from the group consisting of halogen, cyano, hydroxy, $C_{1-6}$ alkyl, $C_{3-10}$ cycloalkyl, 3-10 membered heterocyclyl, $C_{1-6}$ haloalkyl, $C_{1-6}$ alkoxy, $C_{1-6}$ haloalkoxy, —$NR^aR^b$, —$CO_2R^a$ and —$S(O)_2R^a$;

$R^6$ is selected from the group consisting of H, $C_{1-6}$ alkyl, $C_{3-10}$ cycloalkyl, 3-10 membered heterocyclyl, $C_{6-10}$ aryl, 5-10 membered heteroaryl, —$OR^a$ and —$C(O)_2R^7$, wherein the $C_{1-6}$ alkyl, $C_{6-10}$ cycloalkyl, 3-10 membered heterocyclyl, $C_{6-10}$ aryl and 5-10 membered heteroaryl are optionally substituted with one or more $R^c$;

$R^c$ is each independently selected from the group consisting of halogen, cyano, hydroxy, —$NR^aR^b$, —$C(O)_2$—$R^a$, $C_{1-6}$ alkyl, $C_{1-6}$ alkoxy and $C_{1-6}$ haloalkoxy, wherein the $C_{1-6}$ alkyl, $C_{1-6}$ alkoxy and $C_{1-6}$ haloalkoxy are each optionally substituted with one or more substituents independently selected from the group consisting of cyano, —$OR^a$, —$NR^aR^b$, —$C(O)_2$—$R^a$, $C_{1-6}$ alkoxy and —$SO_2R^a$;

$R^7$ is selected from the group consisting of H, $C_{1-6}$ alkyl, $C_{3-10}$ cycloalkyl and 3-10 membered heterocyclyl, wherein the $C_{1-6}$ alkyl, $C_{3-10}$ cycloalkyl and 3-10 membered heterocyclyl are each optionally substituted with one or more substituents independently selected from the group consisting of halogen, cyano, hydroxyl, 3-10 membered heterocyclyl, —$NR^aR^b$, —$C(O)_2$—$R^a$, $C_{1-6}$ alkoxy and —$SO_2R^a$;

$R^8$ is each independently selected from the group consisting of H, halogen, cyano, —$OR^a$, —$SR^a$, —$NR^aR^b$, $C_{1-6}$ alkyl, $C_{2-6}$ alkenyl, $C_{2-6}$ alkynyl, $C_{3-6}$ cycloalkyl, 3-6 membered heterocyclyl, $C_{6-10}$ aryl and 5-10 membered heteroaryl, wherein the $C_{1-6}$ alkyl, $C_{2-6}$ alkenyl, $C_{2-6}$ alkynyl, $C_{3-6}$ cycloalkyl, 3-6 membered heterocyclyl, $C_{6-10}$ aryl and 5-10 membered heteroaryl are each optionally substituted with one or more substituents independently selected from the group consisting of halogen, $C_{1-6}$ alkyl, $C_{1-6}$ haloalkyl, cyano, hydroxy, $C_{3-6}$ cycloalkyl, 3-6 membered heterocyclyl. $C_{6-10}$ aryl, 5-10 membered heteroaryl, $C_{1-6}$ alkoxy and —$OR^a$; or two $R^8$ on different carbon atoms are taken together with the carbon atoms between them to form a $C_{3-6}$ cycloalkyl or a 3-6 membered heterocyclyl; or two $R^8$ on the same carbon atom are taken together with the carbon atom to which they are bonded to form a $C_{3-6}$ cycloalkyl or a 3-6 membered heterocyclyl;

$R^9$ is each independently selected from the group consisting of H, halogen, cyano, —$OR^a$, —$SR^a$, —$NR^aR^b$, $C_{1-6}$ alkyl, $C_{2-6}$ alkenyl, $C_{2-6}$ alkynyl, $C_{1-6}$ cycloalkyl, 3-6 membered heterocyclyl, $C_{6-10}$ aryl and 5-10 membered heteroaryl, wherein the $C_{1-6}$ alkyl, $C_{2-6}$ alkenyl, $C_{2-6}$ alkynyl, $C_{3-6}$ cycloalkyl, 3-6 membered heterocyclyl, $C_{6-10}$ aryl and 5-10 membered heteroaryl are each optionally substituted with one or more substituents independently selected from the group consisting of halogen, $C_{1-6}$ alkyl, $C_{1-6}$ haloalkyl, cyano, hydroxy, $C_{3-6}$ cycloalkyl, 3-6 membered heterocyclyl, $C_{6-10}$ aryl, 5-10 membered heteroaryl, $C_{1-6}$ alkoxy and —$OR^a$; or two $R^9$ are taken together with the carbon atom to which they are bonded to form a $C_{3-10}$ cycloalkyl or a 3-10 membered heterocyclyl; or any $R^9$ and $R^5$ are taken together with the atoms between them to form a 3-10 membered heterocyclyl;

$R^a$ and $R^b$ are each independently selected from the group consisting of H, $C_{1-6}$ alkyl, $C_{3-6}$ cycloalkyl and $C_{1-6}$ alkoxy, wherein the $C_{1-6}$ alkyl, $C_{3-6}$ cycloalkyl and $C_{1-6}$ alkoxy are each optionally substituted with one or more substituents independently selected from the group consisting of hydroxy, halogen and $C_{1-6}$ alkyl; or $R^a$ and $R^b$ are taken together with the nitrogen atom to which they are bonded to form a 3-7 membered heterocyclyl;

m and n are each independently selected from the group consisting of 0, 1, 2 and 3; and p and q are each independently selected from the group consisting of 1, 2, and 3, or a pharmaceutically acceptable salt, a stereoisomer, a tautomer, a polymorph, a solvate, an N-oxide, an isotope-labeled compound, a metabolite or a prodrug thereof.

According to some embodiments of the present invention, $R^a$ and $R^b$ are each independently selected from the group consisting of H and $C_{1-6}$ alkyl, wherein the $C_{1-6}$ alkyl is optionally substituted with one or more substituents selected from the group consisting of halogen, hydroxy and $C_{1-6}$ alkyl.

According to some embodiments of the present invention, $X^1$ and $X^3$ are the same or different, and are each independently selected from the group consisting of a covalent bond, —O—, —S—, —NH—, —N($C_{1-6}$ alkyl)-, —N($C_{1-6}$ haloalkyl)-, —N($C_{3-6}$ cycloalkyl)- and —N($C_{1-6}$ alkoxy)-. In a preferred embodiment, $X^1$ and $X^3$ are the same, and are selected from the group consisting of —O—, —S—, —NH— and —N($C_{1-6}$ alkyl)-. In a more preferred embodiment, $X^1$ and $X^3$ are the same, and are selected from the group consisting of —O— and —S—. In a particularly preferred embodiment, both $X^1$ and $X^3$ are —O—.

According to some embodiments of the present invention, $X^2$ is selected from the group consisting of $C_{1-4}$ alkylene, $C_{2-4}$ alkenylene, $C_{2-4}$ alkynylene, $C_{3-6}$ cycloalkyl, 3-6 membered heterocyclyl, $C_{1-4}$ alkylene-$X^4$— and $C_{1-4}$ alkylene-$X^4$—$C_{1-4}$ alkylene, wherein the $C_{1-4}$ alkylene, $C_{2-4}$ alkenylene, $C_{2-4}$ alkynylene, $C_{3-6}$ cycloalkyl and 3-6 membered heterocyclyl are optionally substituted with one or more substituents selected from the group consisting of halogen, cyano, hydroxy, $C_{1-6}$ alkyl and $C_{1-6}$ alkoxy. In a preferred embodiment, $X^2$ is selected from the group consisting of $C_{1-4}$ alkylene, $C_{2-4}$ alkenylene, $C_{1-4}$ alkylene-O—$C_{1-4}$ alkylene, $C_{1-4}$ alkylene-S—$C_{1-4}$ alkylene and $C_{1-4}$ alkylene-$NR^a$—$C_{1-4}$ alkylene, wherein the $C_{1-4}$ alkylene and $C_{2-4}$ alkenylene are optionally substituted with one or more substituents selected from the group consisting of halogen, cyano, hydroxy, $C_{1-6}$ alkyl and $C_{1-6}$ alkoxy. In a more preferred embodiment. $X^2$ is $C_{1-4}$ alkylene optionally substituted with one or more substituents selected from the group consisting of hydroxy and $C_{1-4}$ alkyl. In a more preferred embodiment, $X^2$ is unsubstituted $C_{1-4}$ alkylene. In a particularly preferred embodiment, $X^2$ is propylene.

According to some embodiments of the present invention, $R^8$ is each independently selected from the group consisting of H and $C_{1-6}$ alkyl. In a preferred embodiment, $R^8$ is H.

According to some embodiments of the present invention, p is 2.

According to some embodiments of the present invention, $L^1$ is —$(C(R^8)_2)_p$—. In a preferred embodiment, $L^1$ is —$(CH_2)_p$— or —$(C(C_{1-6}\ alkyl)_2)_p$—. In a particularly preferred embodiment, $L^1$ is —$(CH_2)_2$—.

According to some embodiments of the present invention, $L^2$ is —C(O)—.

According to some embodiments of the present invention, $R^9$ is each independently selected from the group consisting of H and $C_{1-6}$ alkyl. In a preferred embodiment, $R^9$ is H.

According to some embodiments of the present invention, q is 1, 2 or 3.

According to some embodiments of the present invention, $L^3$ is —$(C(R^9)_2)_q$—. In a preferred embodiment, $L^3$ is —$(CH_2)_q$— or —$(C(C_{1-6}\ alkyl)_2)_q$—. In a particularly preferred embodiment, $L^3$ is —$CH_2$, —$(CH_2)_2$— or —$(CH_2)_3$—.

According to some embodiments of the present invention, $A^1$ is —C(O)—$OR^a$. In a preferred embodiment, $A^1$ is selected from the group consisting of —C(O)—OH and —C(O)—O($C_{1-6}$ alkyl). In a more preferred embodiment, $A^1$ is selected from the group consisting of —C(O)—OH and —C(O)—O($C_{1-3}$ alkyl). In a particularly preferred embodiment, $A^1$ is selected from the group consisting of —C(O)—OH and —C(O)—O—($CH_2CH_3$).

According to some embodiments of the present invention, $R^1$ and $R^4$ are the same or different, and are each independently selected from the group consisting of H, halogen, $C_{1-6}$ alkyl, and $C_{3-6}$ cycloalkyl, wherein the $C_{1-6}$ alkyl and $C_{3-6}$ cycloalkyl are each optionally substituted with one or more substituents independently selected from the group consisting of halogen, $C_{1-6}$ alkyl, $C_{1-6}$ haloalkyl, cyano, hydroxy and $C_{1-6}$ alkoxy. In a preferred embodiment, $R^1$ and/or $R^4$ are H. In a particularly preferred embodiment, both $R^1$ and $R^4$ are H.

According to some embodiments of the present invention, $R^2$ and $R^3$ are the same or different, and are each independently selected from the group consisting of H, halogen and —$OR^a$. In a preferred embodiment, $R^2$ and $R^3$ are the same or different, and are each independently selected from the group consisting of —OH and —O($C_{1-6}$ alkyl), wherein the $C_{1-6}$ alkyl in the —O($C_{1-6}$ alkyl) is optionally substituted with one or more substituents selected from the group consisting of halogen, hydroxy and $C_{1-6}$ alkyl. In a particularly preferred embodiment, $R^2$ and $R^3$ are the same or different, and are each independently selected from the group consisting of methoxy, 2-hydroxy-2-methylpropoxy and 3-hydroxy-3-methylbutoxy.

According to some embodiments of the present invention, $R^5$ is selected from the group consisting of H, $C_{1-6}$ alkyl, and $C_{3-6}$ cycloalkyl. In a preferred embodiment, $R^5$ is $C_{1-6}$ alkyl. In a particularly preferred embodiment, $R^5$ is methyl.

According to some embodiments of the present invention, $R^6$ is selected from the group consisting of 5-6 membered heteroaryl (for example, 5-6 membered nitrogen-containing heteroaryl), —$OR^8$ and —$C(O)_2R^7$, wherein the 5-6 membered heteroaryl is optionally substituted with one or more $C_{1-6}$ alkyl. In a preferred embodiment. $R^6$ is selected from the group consisting of pyrazolyl, —O($C_{1-6}$ alkyl), —$C(O)_2$H and —$C(O)_2$—($C_{1-6}$ alkyl), wherein the pyrazolyl is optionally substituted with one or more $C_{1-6}$ alkyl. In a particularly preferred embodiment, $R^6$ is selected from the group consisting of N-methylpyrazolyl, methoxy, —$C(O)_2$H and —$C(O)_2$—($CH_2CH_3$).

According to some embodiments of the present invention, m and n are each independently selected from the group consisting of 0 and 1. In a preferred embodiment, both m and n are 1.

The present invention encompasses compounds of formula (I) obtained through any combination of the above-mentioned preferred definitions of substituents.

According to some embodiments of the present invention, the compound of the present invention has a structure of formula (II):

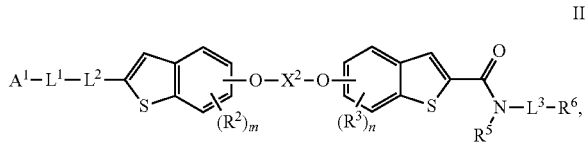

II wherein $A^1$, $L^1$, $L^2$, $L^3$, $R^2$, $R^3$, $R^5$, $R^6$, $X^2$, m and n are as defined above.

According to some embodiments of the present invention, the compound of the present invention has a structure of formula (III):

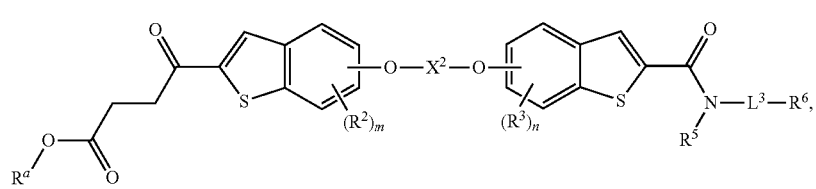

III wherein L³, R², R³, R⁵, R⁶, Rᵃ, X², m and n are as defined above.

According to some embodiments of the present invention, the compound of the present invention has a structure of formula (III-1):

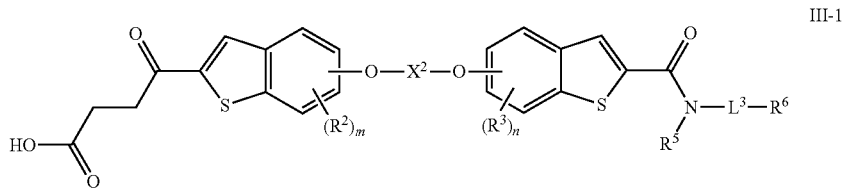

III-1 wherein L³, R², R³, R⁵, R⁶, X², m and n are as defined above.

According to some embodiments of the present invention, the compound of the present invention has a structure of formula (IV):

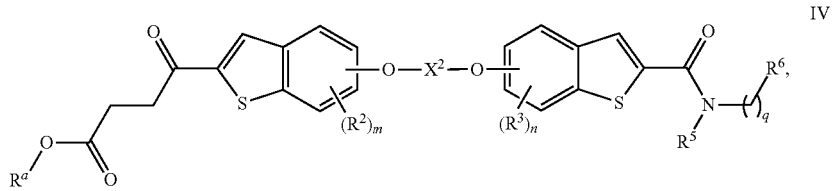

IV wherein R², R³, R⁵, R⁶, Rᵃ, X², m, n and q are as defined above.

Preferably, in the compound of formula (IV),
R² and R³ are the same or different, and are each independently selected from —ORᵃ;
R⁵ is $C_{1-6}$ alkyl;
R⁶ is selected from the group consisting of 5-6 membered heteroaryl, —ORᵃ and —C(O)₂R⁷, wherein the 5-6 membered heteroaryl is optionally substituted with one or more $C_{1-6}$ alkyl;
Rᵃ is selected from the group consisting of H and $C_{1-6}$ alkyl, wherein the $C_{1-6}$ alkyl is optionally substituted with one or more substituents selected from the group consisting of hydroxy and $C_{1-6}$ alkyl;
X² is $C_{1-6}$ alkylene;
q is 1, 2 or 3; and
both m and n are 1.

According to some embodiments of the present invention, the compound of the present invention is selected from the group consisting of:

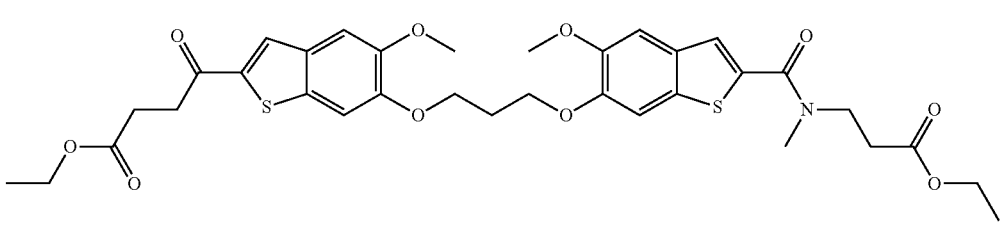

1

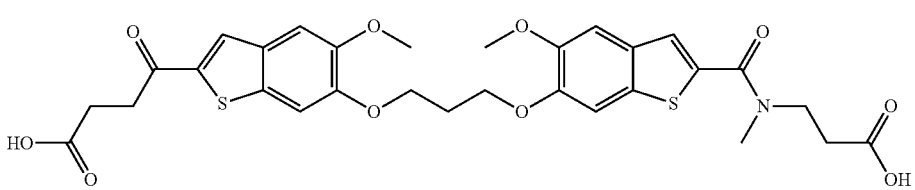

2

3
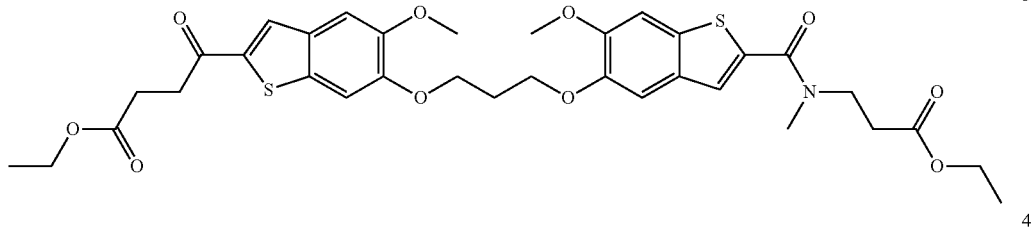
4
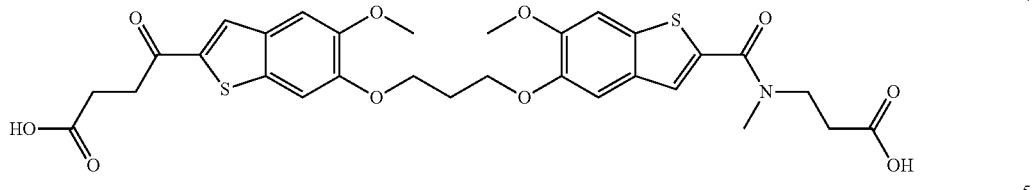
5
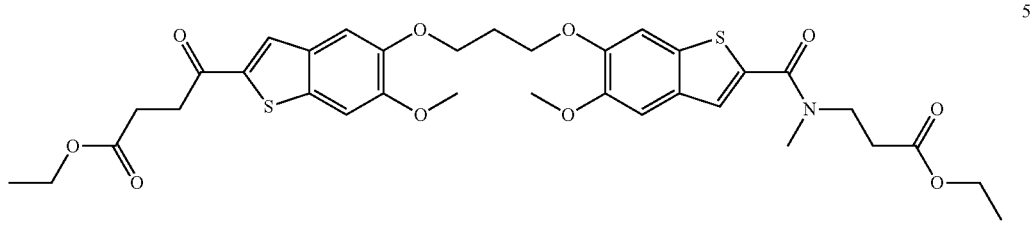
6
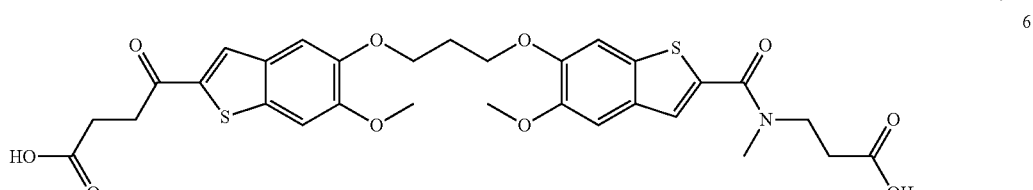
7
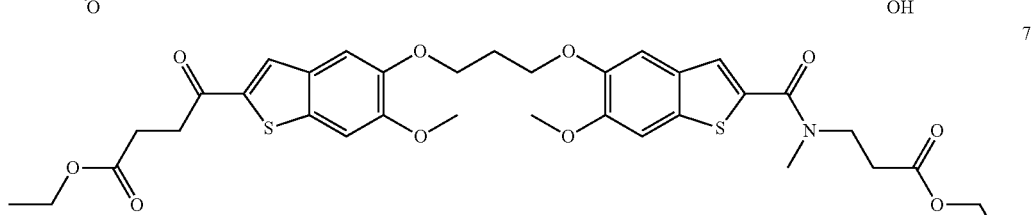
8
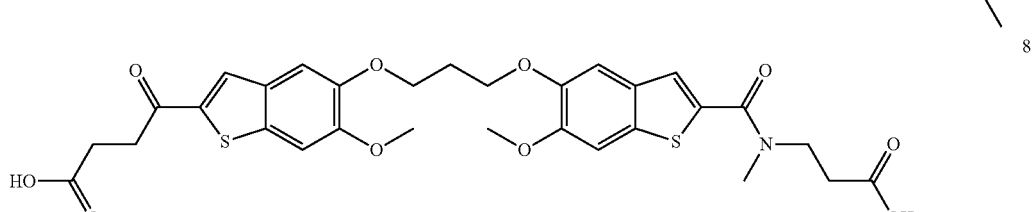
9
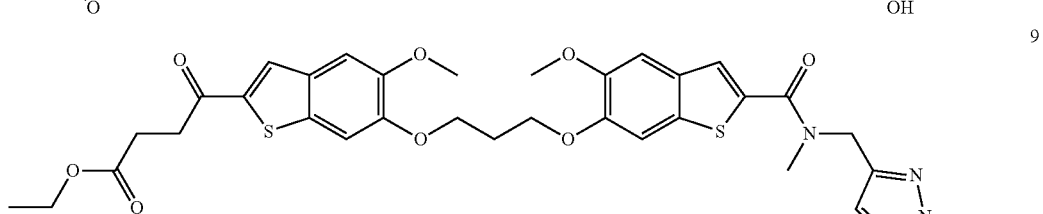
10
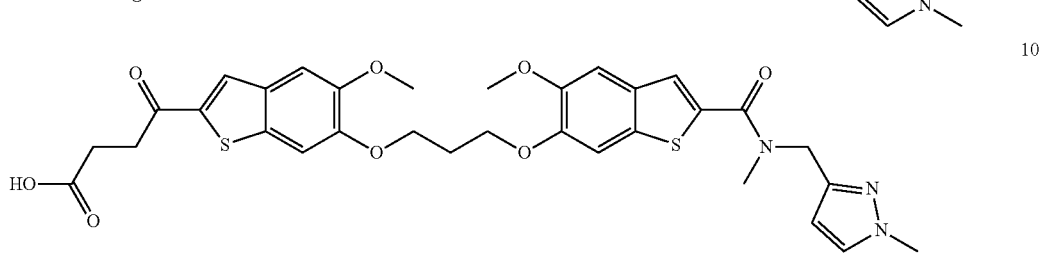

-continued
11
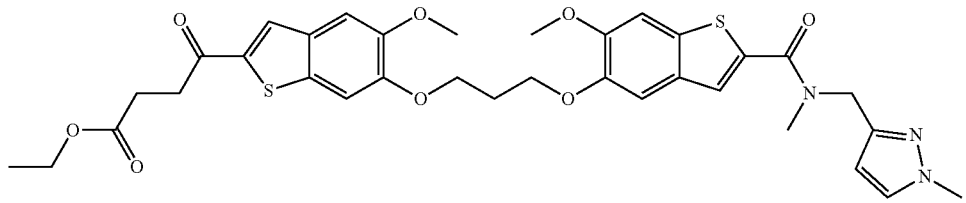
12
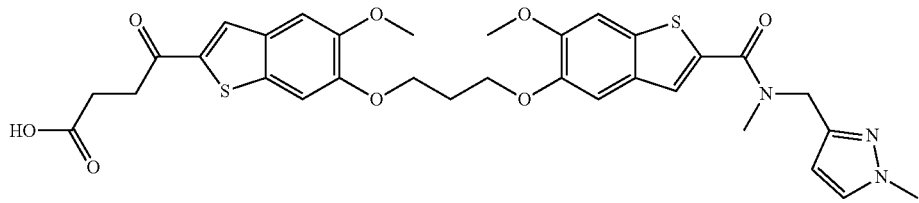
13
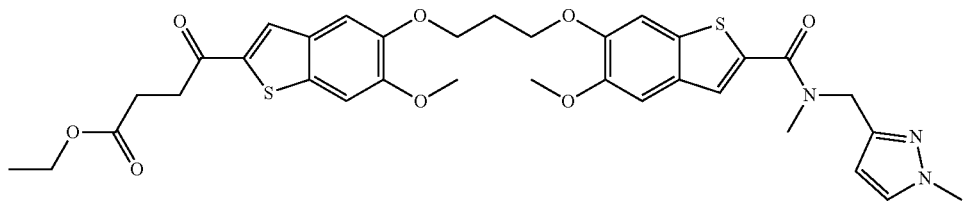
14
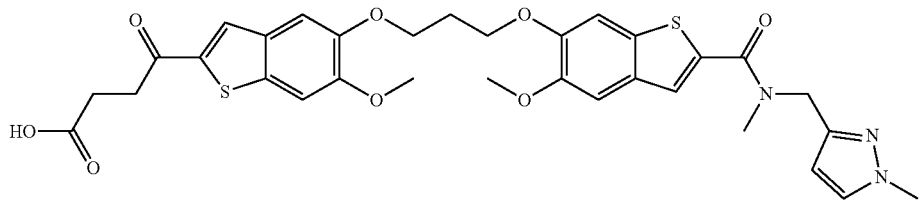
15
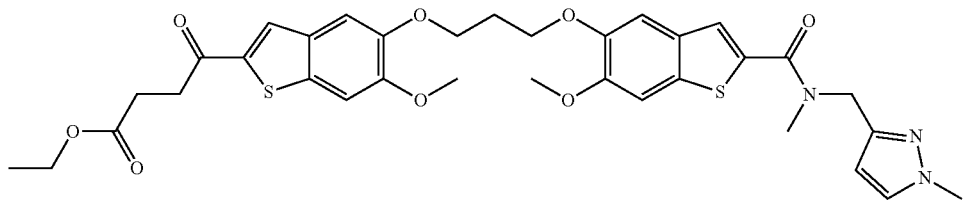
16
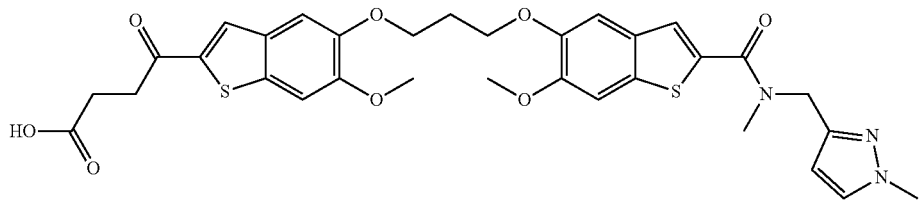
17
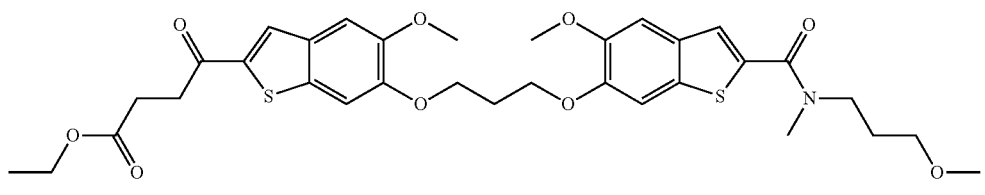
18
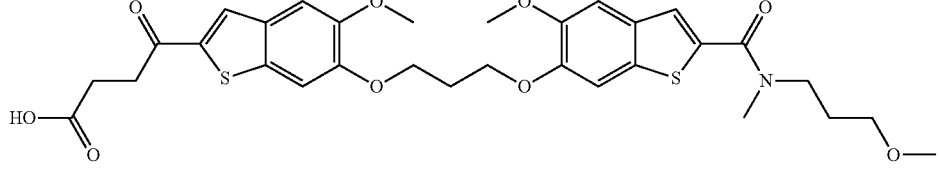

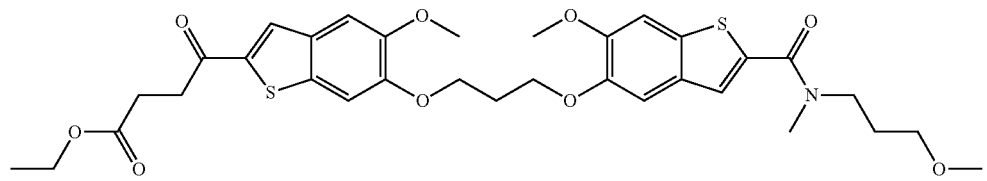
19
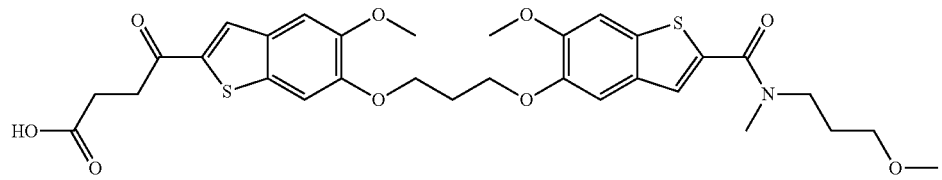
20
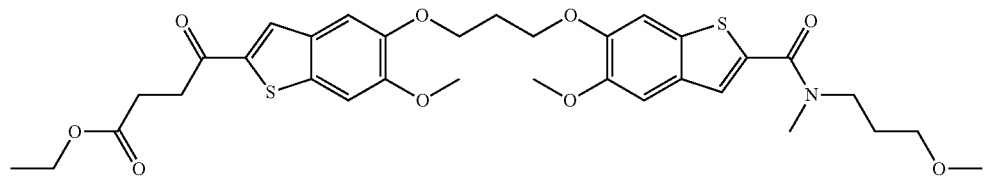
21
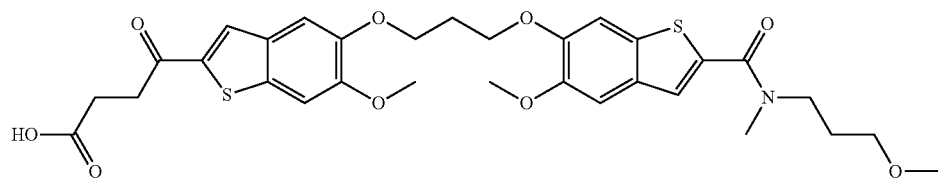
22
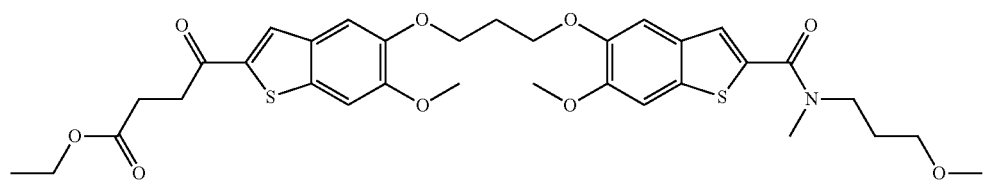
23
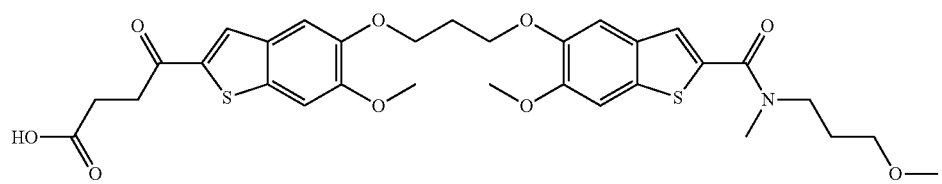
24
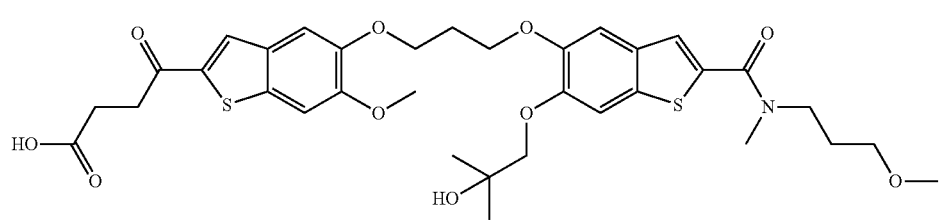
25
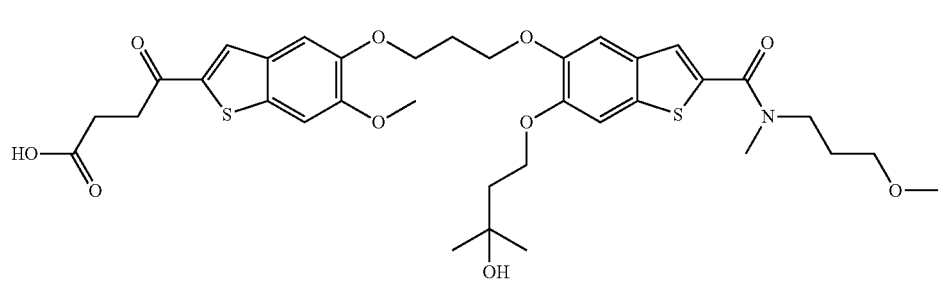
26

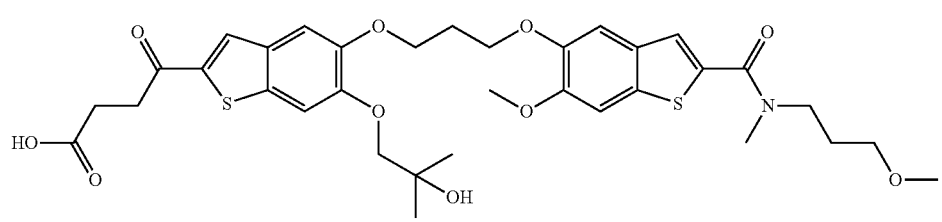
27
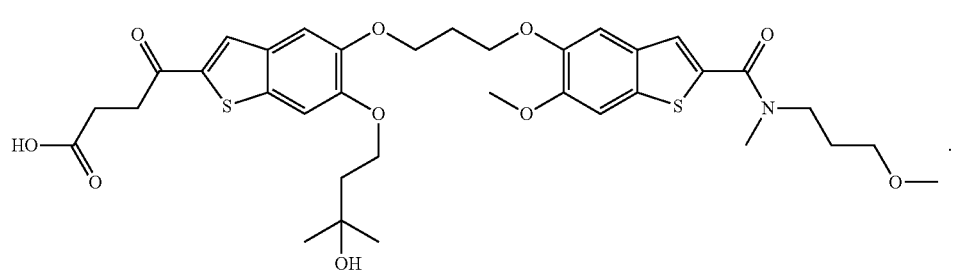
28
Preparation Method
Another object of the present invention is to provide a method for preparing the compound of the present invention. For example, the present invention provides a method for preparing a compound of formula (III), comprising the following steps:
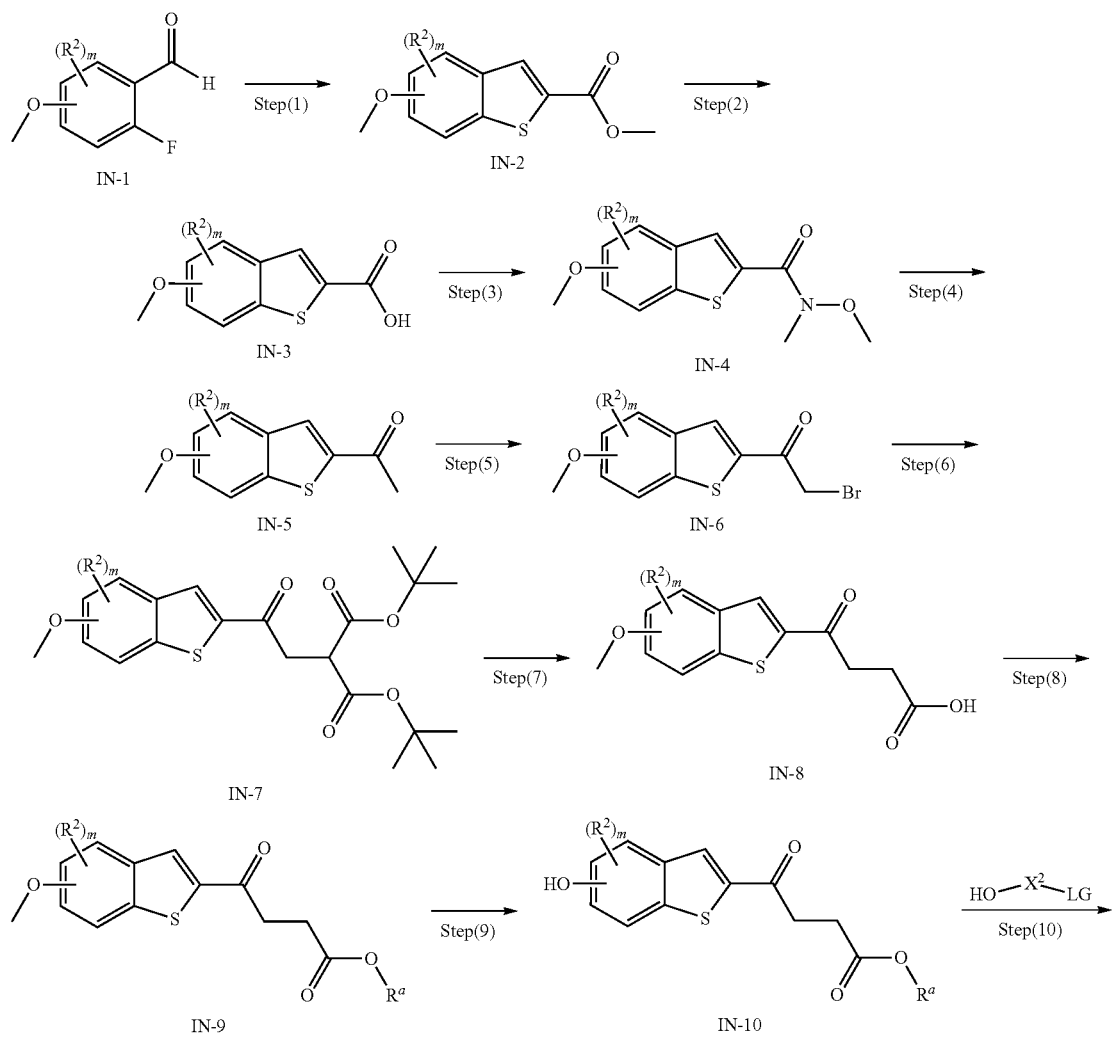

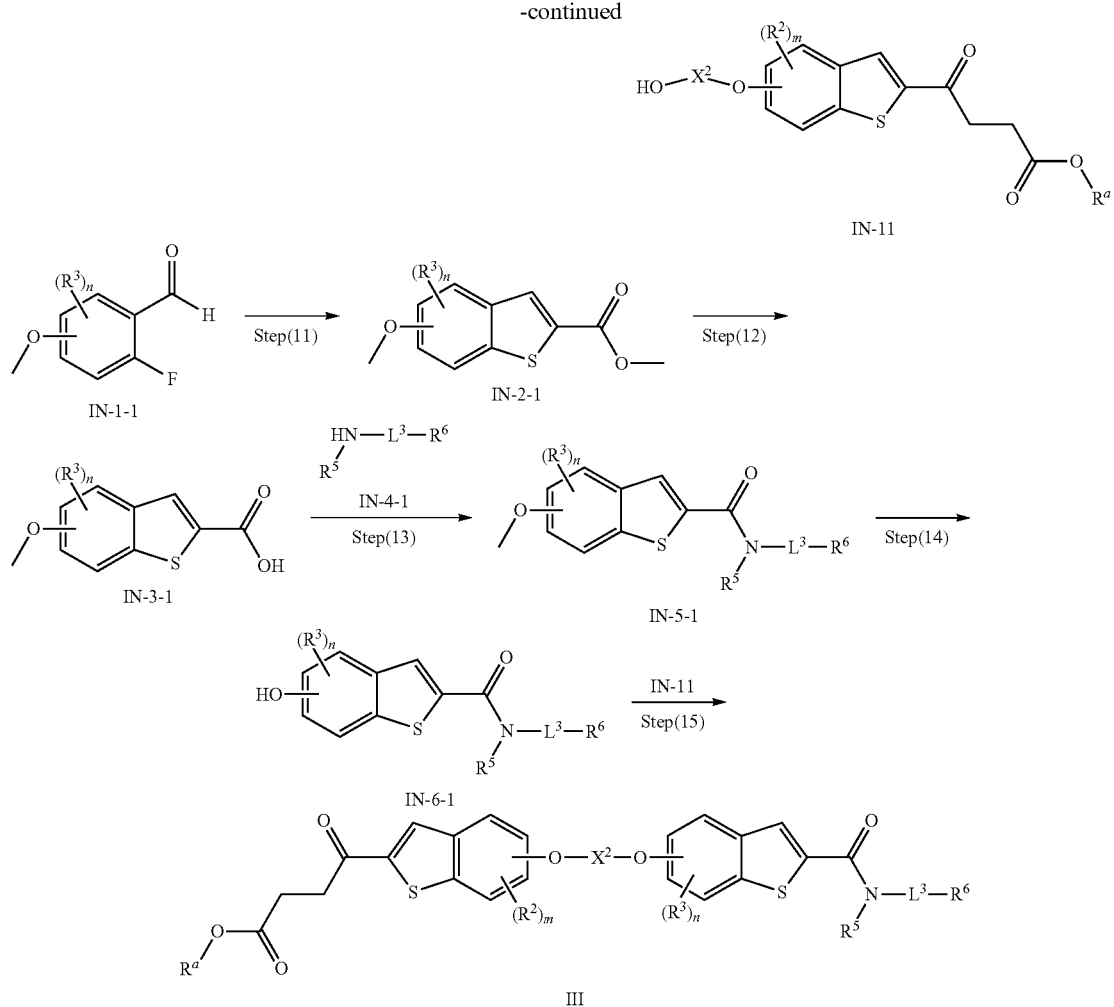

wherein

L³, R², R³, R⁵, R⁶, X², m and n are as defined above;

$R^a$ is selected from the group consisting of $C_{1-6}$ alkyl and $C_{3-6}$ cycloalkyl, wherein the $C_{1-6}$ alkyl and $C_{3-6}$ cycloalkyl are each optionally substituted with one or more substituents independently selected from the group consisting of halogen, hydroxy and $C_{1-6}$ alkyl; and LG represents a leaving group, wherein the leaving group includes, but is not limited to, a halogen atom, methanesulfonyloxy, p-toluenesulfonyloxy, and the like.

Step (1): Reacting Compound IN-1 with Methyl Thioglycolate to Obtain Compound IN-2.

The reaction is preferably carried out in a suitable organic solvent. The organic solvent can be selected from the group consisting of tetrahydrofuran, N,N-dimethylformamide, N,N-dimethylacetamide, acetonitrile, and any combination thereof, preferably N,N-dimethylformamide.

The reaction is preferably carried out in the presence of a suitable base. The base can be selected from diisopropylethylamine, triethylamine, pyridine, 4-dimethylaminopyridine, sodium carbonate, potassium carbonate, and sodium bicarbonate, preferably potassium carbonate.

The reaction is carried out at a suitable temperature, preferably 25-100° C.

The reaction lasts for a suitable period, for example, 2-8 hours.

Step (2): Hydrolyzing Compound IN-2 to Obtain Compound IN-3.

The reaction is preferably carried out in a suitable solvent. The solvent is water or a mixed solvent of water and a solvent selected from the group consisting of tetrahydrofuran, methanol, ethanol, and any combination thereof, preferably a mixed solvent of methanol and water.

The reaction is preferably carried out in the presence of a suitable base. The base can be selected from the group consisting of lithium hydroxide and sodium hydroxide, preferably sodium hydroxide.

The reaction is carried out at a suitable temperature, preferably 25-60° C.

The reaction lasts for a suitable period, for example, 2-8 hours.

Step (3): Reacting Compound IN-3 with Dimethylhydroxylamine Hydrochloride to Obtain Compound IN-4.

The reaction is preferably carried out in a suitable organic solvent. The organic solvent can be selected from the group consisting of tetrahydrofuran, N,N-dimethylformamide, N,N-dimethylacetamide, dichloromethane, and any combination thereof, preferably dichloromethane.

The reaction is preferably carried out in the presence of a suitable condensing agent. The condensing agent can be selected from the group consisting of dicyclohexylcarbodiimide, 1-(3-dimethylaminopropyl)-3-ethylcarbodiimide, HATU, benzotriazole-N,N,N',N'-tetramethyluronium hexafluorophosphate and 1H-benzotriazol-1-yloxytripyrrolidinophosphonium hexafluorophosphate, preferably HATU.

The reaction is preferably carried out in the presence of an organic base. The organic base can be selected from the group consisting of triethylamine, pyridine, 4-dimethylaminopyridine, diisopropylethylamine, preferably diisopropylethylamine.

The reaction is carried out at a suitable temperature, preferably 25-60° C.

The reaction lasts for a suitable period, for example, 2-8 hours.

Step (4): Reacting Compound IN-4 with Methylmagnesium Bromide to Obtain Compound IN-5.

The reaction is preferably carried out in a suitable organic solvent. The organic solvent can be selected from the group consisting of diethyl ether, tetrahydrofuran, 1,4-dioxane, and any combination thereof, preferably tetrahydrofuran.

The reaction is carried out at a suitable temperature, preferably −10-50° C.

The reaction lasts for a suitable period, for example, 2-8 hours.

Step (5): Reacting Compound IN-5 with a Suitable Brominating Agent to Obtain Compound IN-6.

The reaction is preferably carried out in a suitable organic solvent. The organic solvent can be selected from the group consisting of ethyl acetate, acetonitrile, tetrahydrofuran, and any combination thereof, preferably ethyl acetate.

The brominating agent can be selected from the group consisting of N-bromosuccinimide, trimethylphenylammonium tribromide, pyridinium tribromide and copper bromide, preferably copper bromide.

The reaction is carried out at a suitable temperature, preferably 25-100° C.

The reaction lasts for a suitable period, for example, 2-8 hours.

Step (6): Reacting Compound IN-6 with Di-Tert-Butyl Malonate to Obtain Compound IN-7.

The reaction is preferably carried out in a suitable organic solvent. The organic solvent can be selected from the group consisting of diethyl ether, tetrahydrofuran, 1,4-dioxane, and any combination thereof, preferably tetrahydrofuran.

The reaction is preferably carried out in the presence of a suitable base. The base can be selected from the group consisting of sodium hydride, potassium tert-butoxide, sodium tert-butoxide, sodium methoxide, potassium carbonate, and the like, preferably sodium hydride.

The reaction is carried out at a suitable temperature, preferably −10-40° C.

The reaction lasts for a suitable period, for example, 2-8 hours.

Step (7): Allowing Compound IN-7 to React to Obtain Compound IN-8.

The reaction is preferably carried out in a suitable solvent. The solvent can be selected from the group consisting of 1,4-dioxane, ethyl acetate, water, and any combination thereof, preferably 1,4-dioxane.

The reaction is preferably carried out in the presence of a suitable acid. The acid can be selected from the group consisting of hydrochloric acid, sulfuric acid and trifluoroacetic acid, preferably hydrochloric acid.

The reaction is carried out at a suitable temperature, preferably 60-150° C.

The reaction lasts for a suitable period, for example, 12-36 hours.

Step (8): Subjecting Compound IN-8 and HO—$R^a$ to an Esterification Reaction to Obtain Compound IN-9.

The reaction is carried out in a suitable organic solvent. The organic solvent can be selected from the group consisting of tetrahydrofuran, N,N-dimethylformamide, acetonitrile, toluene, alcohol solvents (such as methanol and ethanol), and any combination thereof. When $R^a$ is ethyl, the reaction is preferably carried out in ethanol.

The reaction is preferably carried out in the presence of a suitable catalyst. The catalyst can be selected from the group consisting of hydrochloric acid, sulfuric acid and thionyl chloride, preferably sulfuric acid.

The reaction is carried out at a suitable temperature, preferably 60-150° C.

The reaction lasts for a suitable period, for example, 2-6 hours.

Step (9): Subjecting Compound IN-9 to a Demethylation Reaction to Obtain Compound IN-10.

The reaction is preferably carried out in a suitable organic solvent. The organic solvent can be selected from the group consisting of dichloromethane, chloroform, toluene, and any combination thereof, preferably dichloromethane.

The reaction is preferably carried out in the presence of a suitable Lewis acid.

The Lewis acid can be selected from the group consisting of boron tribromide, aluminum trichloride, and the like, preferably aluminum trichloride.

The reaction is carried out at a suitable temperature, preferably 25-100° C.

The reaction lasts for a suitable period, for example, 15-36 hours.

Step (10): Reacting Compound IN-10 with HO—$X_2$-LG to Obtain Compound IN-11.

The reaction is preferably carried out in a suitable organic solvent. The organic solvent can be selected from the group consisting of N,N-dimethylformamide, N-methylpyrrolidone, tetrahydrofuran, acetone, and the like, and any combination thereof, preferably acetone.

The reaction is preferably carried out in the presence of a suitable base. The base can be selected from the group consisting of potassium carbonate, sodium carbonate, sodium hydride, potassium tert-butoxide, sodium tert-butoxide, sodium methoxide, and the like, preferably potassium carbonate.

The reaction is preferably carried out in the presence of a suitable catalyst. The catalyst can be selected from the group consisting of potassium iodide, sodium iodide, and the like, preferably potassium iodide.

The reaction is carried out at a suitable temperature, preferably 20-100° C.

The reaction lasts for a suitable period, for example, 2-8 hours.

Step (11): Reacting Compound IN-1-1 with Methyl Thioglycolate to Obtain Compound IN-2-1.

The reaction is preferably carried out in a suitable organic solvent. The organic solvent can be selected from the group consisting of tetrahydrofuran, N,N-dimethylformamide, N,N-dimethylacetamide, acetonitrile, and any combination thereof, preferably N,N-dimethylformamide.

The reaction is preferably carried out in the presence of a suitable base. The base can be selected from the group consisting of diisopropylethylamine, triethylamine, pyridine, 4-dimethylaminopyridine, sodium carbonate, potassium carbonate, and sodium bicarbonate, preferably potassium carbonate.

The reaction is carried out at a suitable temperature, preferably 25-100° C.

The reaction lasts for a suitable period, for example, 2-8 hours.

Step (12): Hydrolyzing Compound IN-2-1 to Obtain Compound IN-3-1.

The reaction is preferably carried out in a suitable solvent. The solvent is water or a mixed solvent of water and a solvent selected from the group consisting of tetrahydrofuran, methanol, ethanol, and any combination thereof, preferably a mixed solvent of methanol and water.

The reaction is preferably carried out in the presence of a suitable base. The base can be selected from the group consisting of lithium hydroxide and sodium hydroxide, preferably sodium hydroxide.

The reaction is carried out at a suitable temperature, preferably 25-60° C.

The reaction lasts for a suitable period, for example, 2-8 hours.

Step (13): Reacting Compound IN-3-1 with Compound IN-4-1 to Obtain Compound IN-5-1.

The reaction is preferably carried out in a suitable organic solvent. The organic solvent can be selected from the group consisting of tetrahydrofuran, N,N-dimethylformamide, N,N-dimethylacetamide, dichloromethane, and any combination thereof, preferably dichloromethane.

The reaction is preferably carried out in the presence of a suitable condensing agent. The condensing agent can be selected from the group consisting of dicyclohexylcarbodiimide, 1-(3-dimethylaminopropyl)-3-ethylcarbodiimide, HATU, benzotriazole-N,N,N',N'-tetramethyluronium hexafluorophosphate and 1H-benzotriazol-1-yloxytripyrrolidinophosphonium hexafluorophosphate, preferably HATU.

The Lewis acid can be selected from the group consisting of boron tribromide, aluminum trichloride, and the like, preferably aluminum trichloride.

The reaction is carried out at a suitable temperature, preferably 25-100° C.

The reaction lasts for a suitable period, for example, 15-36 hours.

Step (15): Reacting Compound IN-6-1 with Compound IN-11 to Obtain the Compound of Formula III.

The reaction is preferably carried out in a suitable organic solvent. The organic solvent can be selected from the group consisting of N,N-dimethylformamide, N-methylpyrrolidone, toluene, tetrahydrofuran, 1,4-dioxane, and any combination thereof, preferably tetrahydrofuran.

The reaction is preferably carried out in the presence of a suitable phosphine reagent. The phosphine reagent can be selected from the group consisting of tri-n-butylphosphine, triphenylphosphine, and the like, preferably triphenylphosphine.

The reaction is preferably carried out in the presence of a suitable azo reagent. The azo reagent can be selected from the group consisting of diisopropyl azodicarboxylate, diethyl azodicarboxylate, azodicarboxylic acid dipiperidide, and the like, preferably diisopropyl azodicarboxylate.

The reaction is carried out at a suitable temperature, preferably 20-60° C.

The reaction lasts for a suitable period, for example, 2-8 hours.

The present invention further provides a method for preparing a compound of formula (III-1), comprising the following steps:

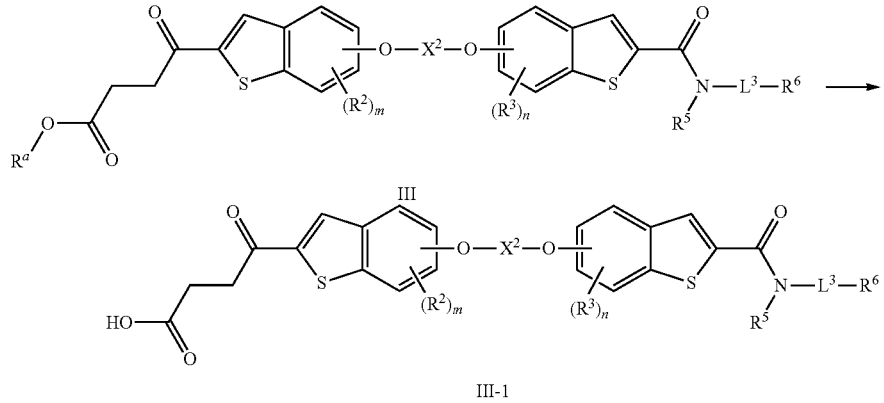

III-1 wherein $L^3$, $R^2$, $R^3$, $R^a$, $R^5$, $R^6$, $X^2$, m and n are as defined above in the method for preparing the compound of formula (III).

The reaction is preferably carried out in a suitable solvent. The solvent is water or a mixed solvent of water and a solvent selected from the group consisting of tetrahydrofuran, methanol, ethanol, and any combination thereof, preferably a mixed solvent of ethanol and water.

The reaction is preferably carried out in the presence of a suitable base. The base can be selected from the group consisting of lithium hydroxide and sodium hydroxide, preferably sodium hydroxide.

The reaction is carried out at a suitable temperature, preferably 25-100° C.

The reaction lasts for a suitable period, for example, 2-8 hours.

The reaction is preferably carried out in the presence of an organic base. The organic base can be selected from the group consisting of triethylamine, pyridine, 4-dimethylaminopyridine, and diisopropylethylamine, preferably diisopropylethylamine.

The reaction is carried out at a suitable temperature, preferably 25-60° C.

The reaction lasts for a suitable period, for example, 2-8 hours.

Step (14): Subjecting Compound IN-5-1 to a Demethylation Reaction to Obtain Compound IN-6-1.

The reaction is preferably carried out in a suitable organic solvent. The organic solvent can be selected from the group consisting of dichloromethane, chloroform, toluene, and any combination thereof, preferably dichloromethane.

The reaction is preferably carried out in the presence of a suitable Lewis acid.

Pharmaceutical Composition and Kit

Another object of the present invention is to provide a pharmaceutical composition comprising a prophylactically or therapeutically effective amount of the compound of the present invention, or a pharmaceutically acceptable salt, a stereoisomer, a tautomer, a polymorph, a solvate, an N-oxide, an isotope-labeled compound, a metabolite or a prodrug thereof, and one or more pharmaceutically acceptable carriers.

Another object of the present invention is to provide a kit comprising the compound of the present invention, or a pharmaceutically acceptable salt, a stereoisomer, a tautomer, a polymorph, a solvate, an N-oxide, an isotope-labeled compound, a metabolite or a prodrug thereof, or the pharmaceutical composition of the present invention.

The term "pharmaceutically acceptable carrier" used in the present invention refers to a diluent, adjuvant, excipient, or vehicle administered together with the therapeutic agent, which, according to sound medical judgment, is suitable for contacting the tissues of human and/or other animals without undue toxicity, irritation, allergic reaction or other problems or complications beyond a reasonable benefit/risk ratio.

The pharmaceutically acceptable carrier which can be employed in the pharmaceutical composition of the present invention includes, but is not limited to, sterile liquids, such as water and oils, including those of petroleum, animal, vegetable or synthetic origin, such as peanut oil, soybean oil, mineral oil, sesame oil and the like.

The pharmaceutical composition may be in the form of, for example, a solid preparation, a semi-solid preparation, a liquid preparation, or a gaseous preparation. The solid preparation is, for example, a tablet, a capsule, a powder, a granule, or a suppository, etc., and the liquid preparation is, for example, a solution, a suspension, or an injection. The composition may also be in the form of liposomes, microspheres, and the like. In particular, the pharmaceutical composition is in a dosage form suitable for oral administration.

Water is an exemplary carrier when the pharmaceutical composition is for intravenous administration. Physiological saline as well as aqueous dextrose and glycerol solutions can also be employed as liquid carriers, particularly for injectable solutions. Suitable pharmaceutical excipients include starch, glucose, lactose, sucrose, gelatin, maltose, chalk, silica gel, sodium stearate, glyceryl monostearate, talc, sodium chloride, dried skim milk, glycerol, propylene glycol, water, ethanol and the like. The composition, if desired, can also contain minor amounts of wetting agents, emulsifying agents, or pH buffering agents. Oral formulations may include standard carriers, such as mannitol, lactose, starch, magnesium stearate, sodium saccharine, cellulose, magnesium carbonate, and the like in pharmaceutical grade. Examples of suitable pharmaceutical acceptable carriers are described in e.g. Remington's Pharmaceutical Sciences (1990).

The pharmaceutical composition of the present invention can act systemically and/or topically. For this purpose, it can be administered through a suitable route, for example, it can be administered via injection (for example, intravenous, intraarterial, subcutaneous, intraperitoneal, or intramuscular injection, including infusion), or via transdermal route, or via oral, buccal, nasal, transmucosal or topical route, or as an ophthalmic formulation, or via inhalation.

For these routes of administration, the pharmaceutical composition of the present invention may be administered in a suitable dosage form. Such dosage forms include, but are not limited to, tablets, capsules, lozenges, hard candies, powders, sprays, creams, salves, suppositories, gels, pastes, lotions, ointments, aqueous suspensions, injectable solutions, elixirs, syrups, and the like.

The content or amount of the compound of the present invention in a pharmaceutical composition may be from about 0.001 mg to about 1000 mg, suitably 0.01-800 mg, preferably 0.05-500 mg, more preferably 0.1-350 mg, particularly preferably 0.5-100 mg.

In some embodiments, the present invention provides a method for preparing the pharmaceutical composition of the present invention, comprising: combining the compound of the present invention, or a pharmaceutically acceptable salt, a stereoisomer, a tautomer, a polymorph, a solvate, an N-oxide, an isotope-labeled compound, a metabolite or a prodrug thereof, with one or more pharmaceutically acceptable carriers.

Therapeutic Method and Use

Another object of the present invention is to provide use of the compound of the present invention, or a pharmaceutically acceptable salt, a stereoisomer, a tautomer, a polymorph, a solvate, an N-oxide, an isotope-labeled compound, a metabolite or a prodrug thereof, or the pharmaceutical composition of the present invention for activating the STING signal pathway.

Another object of the present invention is to provide use of the compound of the present invention, or a pharmaceutically acceptable salt, a stereoisomer, a tautomer, a polymorph, a solvate, an N-oxide, an isotope-labeled compound, a metabolite or a prodrug thereof, or the pharmaceutical composition of the present invention for the prophylaxis or treatment of a STING-mediated disease.

Another object of the present invention is to provide use of the compound of the present invention, or a pharmaceutically acceptable salt, a stereoisomer, a tautomer, a polymorph, a solvate, an N-oxide, an isotope-labeled compound, a metabolite or a prodrug thereof, or the pharmaceutical composition of the present invention in the manufacture of a medicament for the prophylaxis or treatment of a STING-mediated disease.

Another object of the present invention is to provide a method for the prophylaxis or treatment of a STING-mediated disease, comprising administering to a subject in need thereof a prophylactically or therapeutically effective amount of the compound of the present invention, or a pharmaceutically acceptable salt, a stereoisomer, a tautomer, a polymorph, a solvate, an N-oxide, an isotope-labeled compound, a metabolite or a prodrug thereof, or the pharmaceutical composition of the present invention.

According to some embodiments of the present invention, the STING-mediated disease is tumor. Preferably, the disease is cancer.

The term "effective amount" as used herein refers to an amount sufficient to achieve a desired prophylactic or therapeutic effect, for example, an amount that achieves alleviation of one or more symptoms associated with the disease to be treated.

The dose regimen can be adjusted to achieve an optimal response. For example, the drug can be administered in a single bolus or in several sub-doses over time, or the dose can be proportionally decreased or increased according to practical requirement of treatment. It should be noted that the dose may vary depending on the type and severity of the condition to be alleviated, and may include single- or multi-doses. It will be further understood that for any particular subject, the specific dose regimen should be adjusted according to the requirement of the subject, and the professional judgment of the skilled physician who is in charge of administering or monitoring the administration of the pharmaceutical composition.

The amount of the compound of the present invention administered will be dependent on the subject being treated, the severity of the disorder or condition, the rate of administration, the disposition of the compound and the discretion of the prescribing physician. Generally, an effective dosage is in the range of about 0.0001 to about 50 mg per kg body weight per day, for example about 0.01 to about 10 mg/kg/day (in single- or multi-doses). For a person of 70 kg, the effective dose will be about 0.007 mg/day to about 3,500 mg/day in total, for example, about 0.7 mg/day to about 700 mg/day in total. In some instances, dosage levels below the lower limit of the aforesaid range may be more than adequate, while in other cases, still larger doses may be employed without causing any harmful side effect, provided that such larger doses are first divided into several small doses for administration throughout the day.

Unless otherwise indicated, the term "treating" or "treatment", as used herein, means reversing, alleviating, inhibiting the progress of, or preventing the disorder or condition to which such term applies, or one or more symptoms of such disorder or condition.

As used herein, the term "subject" includes a human or non-human animal. An exemplary human subject includes a human subject having a disease (such as one described herein) (referred to as a patient), or a normal subject. The term "non-human animal" as used herein includes all vertebrates, such as non-mammals (e.g., birds, amphibians, reptiles) and mammals, such as non-human primates, livestock and/or domesticated animals (such as sheep, dog, cat, cow, pig and the like).

EXAMPLES

The present invention has been further described in detail with reference to the following examples for apparency of the purposes and technical solutions of the present invention. It should be understood by those skilled in the art that these examples are merely provided for illustration of the present invention and are not intended to limit the scope of the invention. If specific conditions are not indicated in the examples, the experiments shall be carried out in accordance with conventional conditions or conditions recommended by the manufacturers. Reagents or instruments used without indication of the manufacturers are all conventional products that are commercially available.

The structures of compounds were identified by nuclear magnetic resonance ($^1$H NMR) or mass spectrometry (MS). $^1$H NMR was determined with a JEOL Eclipse 400 NMR spectrometer, using deuterated methanol (CD$_3$OD), deuterated chloroform (CDCl$_3$) or hexadeuterodimethyl sulfoxide (DMSO-d$_6$) as the solvent, and tetramethylsilane (TMS) as the internal standard, and the chemical shift (δ) was given in ppm.

The MS was determined with an Agilent (ESI) mass spectrometer (manufacturer: Agilent, model: Agilent 6120B).

Parameters of the preparative high-performance liquid chromatography are provided as follows:

Instrument model: Agilent 1260; chromatographic column: Waters SunFire Prep C18 OBD (19 mm×150 mm×5.0 µm); chromatographic column temperature: 25° C.; flow rate: 20.0 mL/min; detection wavelength: 214 nm; elution gradient: (0 min: 10% A, 90% B; 16.0 min: 90% A, 10% B); mobile phase A: acetonitrile; mobile phase B: 0.05% formic acid aqueous solution.

The aluminum plates (20×20 cm) from Merck were used as thin layer chromatographic (TLC) silica gel plates, and the GF 254 (1 mm) from Yantai was used for thin layer chromatographic separation and purification.

The reactions were monitored by thin layer chromatography (TLC) or LC-MS. The developing solvent systems as used included: dichloromethane-methanol system, n-hexane-ethyl acetate system, as well as petroleum ether-ethyl acetate system. The volume ratio of solvents was adjusted according to the polarities of the compounds or by adding triethylamine.

The microwave reactions were conducted using a Biotage Initiator+(400 W, RT to 300° C.) microwave reactor.

Silica gel of 200 to 300 mesh was generally used as the stationary phase in column chromatography. The eluent systems included: dichloromethane-methanol system, and petroleum ether-ethyl acetate system. The volume ratio of solvents was adjusted according to the polarities of compounds, or by adding a small amount of triethylamine.

Unless specified otherwise, the reaction temperature in the following examples was room temperature (20° C.-35° C.).

The reagents used in the present invention were purchased from Acros Organics, Aldrich Chemical Company, Topbiochem, etc.

In conventional synthetic methods, examples and intermediate preparation examples of the present invention, the abbreviations as used herein have the following meanings.

| Abbreviation | Meaning |
|---|---|
| TLC | Thin layer chromatography |
| LC-MS | Liquid chromatography-mass spectrometry |
| DIPEA | N,N-diisopropylethylamine |
| HATU | 2-(7-azobenzotriazole)-N,N,N',N'-tetramethyluronium hexafluorophosphate |
| DMF | N,N-dimethylformamide |
| CD$_3$OD | Deuterated methanol |
| CDCl$_3$ | Deuterated chloroform |
| DMSO-d$_6$ | Hexadeuterodimethyl sulfoxide |
| TMS | Tetramethylsilane |
| NMR | Nuclear magnetic resonance |
| MS | Mass spectrum |
| s | Singlet |
| d | Doublet |
| t | Triplet |
| q | Quartet |
| dd | Double doublet |
| m | Multiplet |
| br | Broad |
| J | Coupling constant |
| Hz | Hertz |

Intermediate Preparation Example 1: Preparation of ethyl 4-(6-hydroxy-5-methoxybenzo[b]thiophen-2-yl)-4-oxobutyrate (Int-A) and ethyl 4-(5-hydroxy-6-methoxybenzo[b]thiophen-2-yl)-4-oxobutyrate (Int-B)

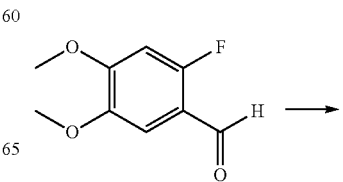

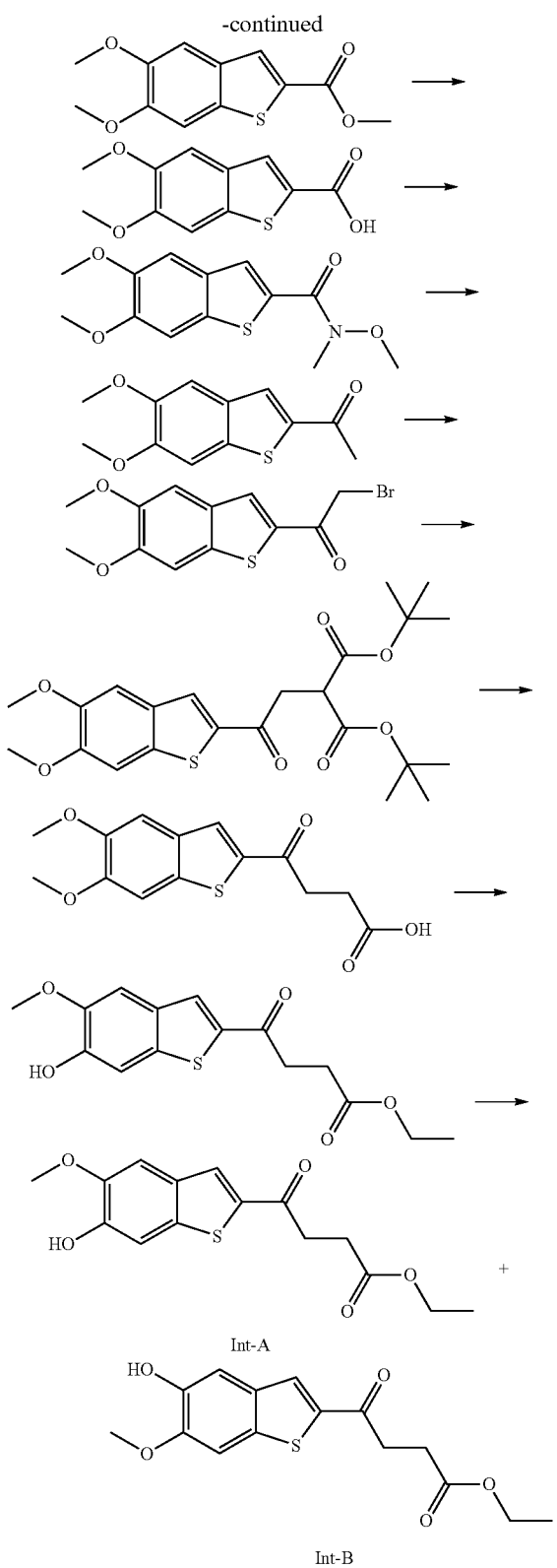

thioglycolate (6.9 g, 65.2 mmol) and potassium carbonate (22.5 g, 162.9 mmol) were added. The reaction mixture was heated to 60° C., and allowed to react for 15 hours. The reaction solution was slowly poured into water (1000 mL). The mixture was stirred for 2 hours and filtered. The resulting solid was washed with water (500 mL), and dried under vacuum at 60° C. to obtain the title compound of this step (12.0 g, yield: 87.6%).

MS m/z (ESI): 253.0 [M+H]$^+$.

Step 2: Preparation of 5,6-dimethoxybenzo[b]thiophene-2-formic Acid

Methyl 5,6-dimethoxybenzo[b]thiophene-2-formate (12.0 g, 47.6 mmol) was dissolved in methanol (100 mL) and water (20 mL), and sodium hydroxide (3.8 g, 95.1 mmol) was added. The reaction mixture was allowed to react at room temperature for 4 hours. The reaction solution was concentrated under reduced pressure at 40° C. to remove part of methanol. The residue was added to water (500 mL). The resulting mixture was adjusted to pH=3 with dilute hydrochloric acid, and filtered. The resulting solid was washed with water (500 mL) and dried under vacuum at 60° C. to obtain the title compound (8.0 g, yield: 70.6%).

MS m/z (ESI): 239.0 [M+H]$^+$.

Step 3: Preparation of N,5,6-trimethoxy-N-methyl-benzo[b]thiophene-2-formamide 5,6-Dimethoxybenzo[b]thiophene-2-formic acid (8.2 g, 34.4 mmol) and dimethylhydroxylamine hydrochloride (4.1 g, 41.3 mmol) were added to dichloromethane (100 mL), and then HATU (13.1 g, 34.4 mmol) and DIPEA (8.9 g, 68.8 mmol) were added sequentially. Then the mixture was allowed to react at room temperature for 4 hours. The reaction solution was poured into water (300 mL), and the mixture was extracted with dichloromethane (50 mL) for three times. The organic phases were combined, dried with anhydrous sodium sulfate, and filtered. The filtrate was concentrated under reduced pressure to obtain the title compound of this step (9.5 g, yield: 98.1%).

MS m/z (ESI): 282.1 [M+H]$^+$.

Step 4: Preparation of 1-(5,6-dimethoxybenzo[b]thiophen-2-yl)ethanone

N,5,6-trimethoxy-N-methylbenzo[b]thiophene-2-formamide (10.0 g, 35.6 mmol) was dissolved in tetrahydrofuran (200 mL). A solution of methylmagnesium bromide (106.6 mmol) in tetrahydrofuran (35.6 mL) was slowly added at 0° C. The reaction mixture was slowly warmed to room temperature and allowed to react for 4 hours. The reaction solution was poured into a saturated aqueous ammonium chloride solution (600 mL), and the mixture was extracted with ethyl acetate (100 mL) for three times. The organic phases were combined, dried with anhydrous sodium sulfate, and filtered. The filtrate was concentrated under reduced pressure to obtain the title compound of this step (7.9 g, yield: 94.1%).

MS m/z (ESI): 237.1 [M+H]$^+$.

Step 5: Preparation of 2-bromo-1-(5,6-dimethoxy-benzo[b]thiophen-2-yl)ethanone 1-(5,6-Dimethoxybenzo[b]thiophen-2-yl)ethanone (2.0 g, 8.5 mmol) and copper bromide (5.7 g, 25.4 mmol) were added to ethyl acetate (60 mL). The mixture was heated up Step 1: Preparation of methyl 5,6-dimethoxy benzo[b]thiophene-2-formate 6-Fluoroveratraldehyde (10.0 g, 54.3 mmol) was dissolved in N,N-dimethylformamide (200 mL), and methyl to 80° C. and allowed to react for 8 hours. The reaction mixture was filtered, and the filtrate was concentrated under reduced pressure. Sodium sulfite (1.8 g, 14.2 mmol), acetonitrile (15 mL), water (15 mL) and acetic acid (8 mL) were added to the residue, followed by stirring at room temperature for 2 hours. The reaction solution was poured into water (150 mL), and the mixture was extracted with ethyl acetate (30 mL) for three times. The organic phases were combined, washed with a saturated aqueous sodium bicarbonate solution, dried with anhydrous sodium sulfate, and filtered. The filtrate was concentrated under reduced pressure to obtain the title compound of this step (1.5 g, yield: 67.0%).

MS m/z (ESI): 315.0 [M+H]$^+$.

Step 6: Preparation of di-tert-butyl 2-(2-(5,6-dimethoxybenzo[b]thiophen-2-yl)-2-oxoethyl)malonate Di-tert-butyl malonate (23.8 g, 110.4 mmol) was dissolved in tetrahydrofuran (200 mL). After that, 60% sodium hydride (4.2 g, 110.4 mmol) was slowly added at 0° C., and the reaction mixture was stirred at 0° C. for 1 hour. A solution of 2-bromo-1-(5,6-dimethoxybenzo[b]thiophen-2-yl)ethanone (17.4 g, 55.2 mmol) in tetrahydrofuran (20 mL) was added slowly. After that, the mixture was slowly warmed up to room temperature, and allowed to react for 2 hours. The reaction solution was poured into a saturated aqueous ammonium chloride solution (500 mL), and the mixture was extracted with ethyl acetate (100 mL) for three times. The organic phases were combined, dried with anhydrous sodium sulfate, and filtered. The filtrate was concentrated under reduced pressure, and the concentrate was purified via preparative high-performance liquid chromatography to obtain the title compound of this step (22.5 g, yield: 90.5%).

Step 7: Preparation of 4-(5,6-dimethoxybenzo[b]thiophen-2-yl)-4-oxobutanoic Acid Di-tert-butyl 2-(2-(5,6-dimethoxy benzo[b]thiophen-2-yl)-2-oxoethyl)malonate (8.0 g, 17.8 mmol) was dissolved in a solution of hydrogen chloride in 1,4-dioxane (80 mL, 4 mol/L). The reaction mixture was allowed to react under stirring at 120° C. for 18 hours. The reaction solution was poured into water (200 mL), and the mixture was extracted with ethyl acetate (50 mL) for three times. The organic phases were combined, washed with a saturated aqueous sodium chloride solution for three times, dried with anhydrous sodium sulfate, and filtered. The filtrate was concentrated under reduced pressure to obtain the title compound of this step (4.7 g, yield: 89.9%).

MS m/z (ESI): 295.1 [M+H]$^+$.

Step 8: Preparation of ethyl 4-(5,6-dimethoxybenzo[b]thiophen-2-yl)-4-oxobutyrate 4-(5,6-Dimethoxybenzo[b]thiophen-2-yl)-4-oxobutanoic acid (4.0 g, 13.6 mmol) was dissolved in ethanol (80 mL). Concentrated sulfuric acid (1 mL) was added while stirring at room temperature. The reaction mixture was heated to 80° C., and allowed to react for 3 hours. The reaction solution was poured into water (200 mL), and the mixture was extracted with ethyl acetate (50 mL) for three times. The organic phases were combined, washed with a saturated aqueous sodium bicarbonate solution, dried with anhydrous sodium sulfate, and filtered. The filtrate was concentrated under reduced pressure to obtain the title compound of this step (3.9 g, yield: 89.0%).

MS m/z (ESI): 323.1 [M+H]$^+$.

Step 9: Preparation of ethyl 4-(6-hydroxy-5-methoxybenzo[b]thiophen-2-yl)-4-oxobutyrate (Int-A) and ethyl 4-(5-hydroxy-6-methoxybenzo[b]thiophen-2-yl)-4-oxobutyrate (Int-B)

Ethyl 4-(5,6-dimethoxybenzo[b]thiophen-2-yl)-4-oxobutyrate (0.73 g, 2.3 mmol) was dissolved in dichloromethane (8 mL). Aluminum trichloride (4.2 g, 22.7 mmol) was added slowly in an ice bath, and the mixture was heated up to room temperature and stirred for 24 hours. The reaction solution was poured into water (100 mL). The resulting mixture was adjusted to pH=2 with dilute hydrochloric acid, and extracted with ethyl acetate (30 mL) for three times. The organic phases were combined, dried with anhydrous sodium sulfate, and filtered. The filtrate was concentrated under reduced pressure. The concentrate was purified by preparative high performance liquid chromatography to obtain ethyl 4-(6-hydroxy-5-methoxybenzo[b]thiophen-2-yl)-4-oxobutyrate (Int-A: 493 mg, yield: 71.4%) and ethyl 4-(5-hydroxy-6-methoxybenzo[b]thiophen-2-yl)-4-oxobutyrate (Int-B: 170 mg, yield: 24.3%).

Int-A:

MS m/z (ESI): 309.1[M+H];

$^1$H-NMR (400 MHz, CDCl$_3$) δ: 7.87 (s, 1H), 7.33 (s, 1H), 7.22 (s, 1H), 6.08 (s, 1H), 4.17 (q, J=8.0 Hz, 2H), 3.97 (s, 3H), 3.32-3.29 (m, 2H), 2.80-2.76 (m, 2H), 1.27 (t, J=8.0 Hz, 3H).

Int-B:

MS m/z (ESI): 309.1[M+H];

$^1$H-NMR (400 MHz, CDCl$_3$) δ: 7.84 (s, 1H), 7.32 (s, 1H), 7.22 (s, 1H), 5.85 (s, 1H), 4.17 (q, J=8.0 Hz, 2H), 3.98 (s, 3H), 3.33-3.30 (m, 2H), 2.79-2.76 (m, 2H), 1.27 (t, J=8.0 Hz, 3H).

Intermediate Preparation Example 2: Preparation of ethyl 4-(6-(3-hydroxypropoxy)-5-methoxybenzo[b]thiophen-2-yl)-4-oxobutyrate (Int C)

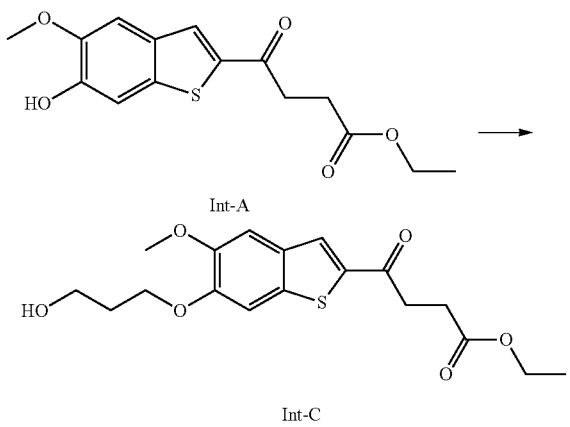

Ethyl 4-(6-hydroxy-5-methoxybenzo[b]thiophen-2-yl)-4-oxobutyrate (Int-A, 500.0 mg, 1.6 mmol) was dissolved in acetone (10 mL). Then potassium carbonate (447.0 mg, 3.2 mmol), potassium iodide (43.0 mg, 0.32 mmol) and 3-bromo-1-propanol (338.0 mg, 2.4 mmol) were added. The reaction mixture was heated to 60° C., and allowed to react for 5 hours. The reaction solution was concentrated and poured into water (50 mL), and the mixture was extracted with ethyl acetate (25 mL) for three times. The organic phases were combined, dried with anhydrous sodium sulfate, and filtered. The filtrate was concentrated under reduced pressure to obtain the title compound of this step (Int C, 485.0 mg, yield: 81.6%).

MS m/z (ESI): 367.1 [M+H]$^+$.

Intermediate Preparation Example 3: Preparation of ethyl 4-(5-(3-hydroxypropoxy)-6-methoxybenzo[b]thiophen-2-yl)-4-oxobutyrate (Int D)

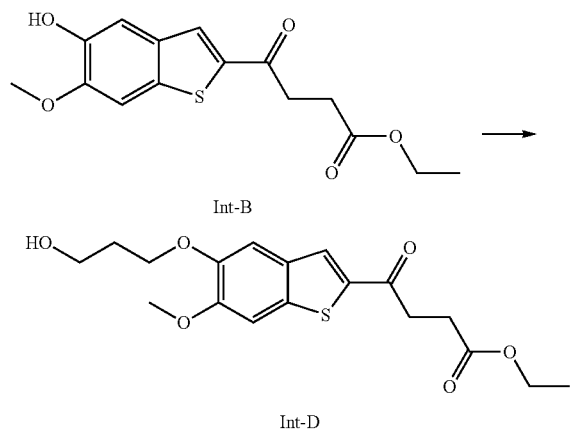

The title compound (Int-D, 380 mg, yield: 79.8%) was obtained using the synthetic route of Intermediate Preparation Example 2, except that ethyl 4-(6-hydroxy-5-methoxybenzo[b]thiophen-2-yl)-4-oxobutyrate (Int-A) was replaced with 4-(5-hydroxy-6-methoxybenzo[b]thiophen-2-yl)-4-oxoethyl butyrate (Int-B).

MS m/z (ESI): 367.1 [M+H]$^+$.

Intermediate Preparation Example 4: Preparation of ethyl 3-(N-methyl-6-hydroxy-5-methoxybenzo[b]thiophene-2-formamido)propionate (Int-E) and ethyl 3-(N-methyl-5-hydroxy-6-methoxybenzo[b]thiophene-2-formamido)propionate (Int-F)

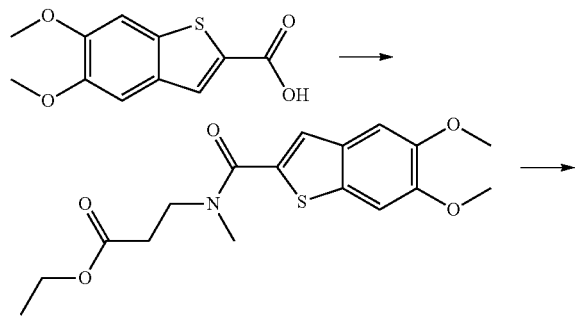

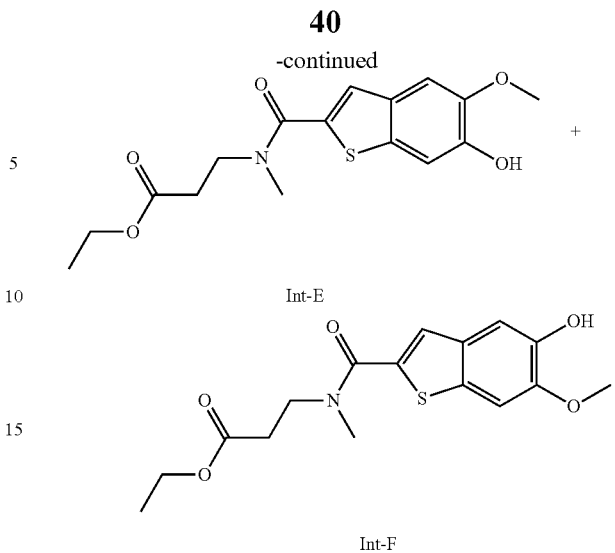

Step 1: Preparation of ethyl 3-(N-methyl-5,6-dimethoxybenzo[b]thiophene-2-formamido)propionate 5,6-Dimethoxybenzo[b]thiophene-2-formic acid (500 mg, 2.10 mmol) and ethyl 3-(methylamino)propionate (389 mg, 2.32 mmol) were dissolved in tetrahydrofuran (15 mL). Then HATU (1.6 g, 4.2 mmol) and DIPEA (814 mg, 6.3 mmol) were added. The reaction mixture was heated to 60° C. and then allowed to react for 4 hours. The reaction solution was poured into water (100 mL), and the mixture was extracted with ethyl acetate (30 mL) for three times. The organic phases were combined, dried with anhydrous sodium sulfate, and filtered. The filtrate was concentrated under reduced pressure, and the concentrate was purified by preparative high-performance liquid chromatography to obtain the title compound of this step (492 mg, yield: 66.8%).

MS m/z (ESI): 352.1 [M+H]$^+$.

$^1$H-NMR (400 MHz, CDC) δ: 7.47 (s, 1H), 7.25 (s, 1H), 7.21 (s, 1H), 4.16 (q, J=7.2 Hz, 2H), 3.97 (s, 3H), 3.95 (s, 3H), 3.88-3.85 (m, 2H), 3.28 (s, 3H), 2.74-2.71 (m, 2H), 1.27 (t, J=7.2 Hz, 3H).

Step 2: Preparation of ethyl 3-(N-methyl-6-hydroxy-5-methoxybenzo[b]thiophene-2-formamido)propionate (Int-E) and ethyl 3-(N-methyl-5-hydroxy-6-methoxybenzo[b]thiophene-2-formamido)propionate (Int-F)

Ethyl 3-(N-methyl-5,6-dimethoxybenzo[b]thiophene-2-formamido)propionate (520 mg, 1.48 mmol) was dissolved in dichloromethane (25 mL). Then aluminum trichloride (1.97 g, 14.80 mmol) was slowly added in an ice bath. The reaction mixture was warmed up to room temperature and stirred for 24 hours. The reaction solution was poured into water (100 mL). The resulting mixture was adjusted to pH=2 with dilute hydrochloric acid, and extracted with ethyl acetate (30 mL) for three times. The organic phases were combined, dried with anhydrous sodium sulfate, and filtered. The filtrate was concentrated under reduced pressure. The concentrate was purified by preparative high performance liquid chromatography to obtain ethyl 3-(N-methyl-6-hydroxy-5-methoxybenzo[b]thiophene-2-formamido)propionate (Int-E, 305 mg, yield: 61.2%) and ethyl 3-(N-methyl-5-hydroxy-6-methoxybenzo[b]thiophene-2-formamido)propionate (Int-F, 174 mg, yield: 34.9%).

Int-E:

MS m/z (ESI): 338.1 [M+H]$^+$;

$^1$H-NMR (400 MHz, DMSO-$d_6$) δ: 9.55 (s, 1H), 7.62 (s, 1H), 7.38 (s, 1H), 7.27 (s, 1H), 4.07 (q, J=8.0 Hz, 2H), 3.85-3.83 (m, 3H), 3.73-3.65 (m, 2H), 3.21-3.18 (m, 3H), 2.68-2.65 (m, 2H), 1.17 (t, J=8.0 Hz, 3H).

Int-F:

MS m/z (ESI): 338.1 [M+H]$^+$;

$^1$H-NMR (400 MHz, DMSO-$d_6$) δ: 9.25 (s, 1H), 7.58 (s, 1H), 7.50 (s, 1H), 7.23 (s, 1H), 4.07 (q, J=8.0 Hz, 2H), 3.85-3.82 (m, 3H), 3.73-3.68 (m, 2H), 3.21-3.18 (m, 3H), 2.68-2.65 (m, 2H), 1.17 (t, J=8.0 Hz, 3H).

Example 1: Preparation of ethyl 4-(6-(3-((2-((3-ethoxy-3-oxopropyl)(methyl)carbamoyl)-5-methoxy-benzo[b]thiophen-6-yl)oxy)propoxy)-5-methoxy-benzo[b]thiophen-2-yl)-4-oxobutyrate (compound 1)

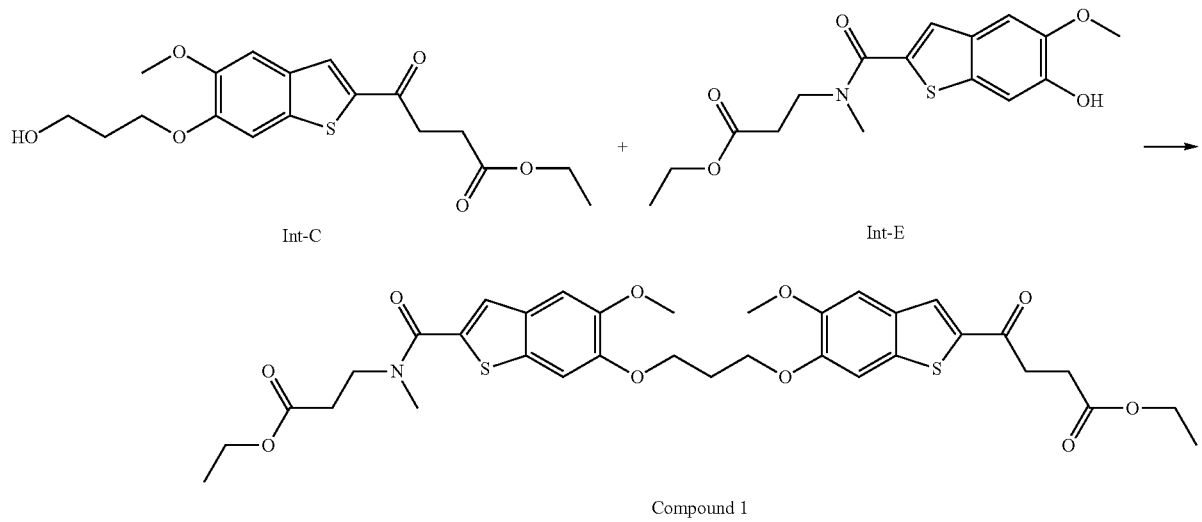

Compound 1

Ethyl 4-(6-(3-hydroxypropoxy)-5-methoxybenzo[b]thiophen-2-yl)-4-oxobutyrate (Int-C, 100 mg, 272.9 μmol), ethyl 3-(N-methyl-6-hydroxy-5-methoxybenzo[b]thiophene-2-formamido)propionate (Int-E, 96 mg, 272.9 μmol) and triphenyl phosphine (143 mg, 545.9 μmol) were dissolved in tetrahydrofuran (10 mL), and diisopropyl azodicarboxylate (110 mg, 545.9 μmol) was added under nitrogen protection. The mixture was then stirred at room temperature for 12 hours. The reaction solution was concentrated under reduced pressure at 40° C. to remove tetrahydrofuran, and the concentrate was purified by preparative high performance liquid chromatography to obtain the title compound (98 mg, yield: 52.4%).

MS m/z (ESI): 686.2 [M+H]$^+$.

$^1$H-NMR (400 MHz, DMSO-$d_6$) δ: 8.21 (s, 1H), 7.66-7.64 (m, 2H), 7.62 (s, 1H), 7.49 (s, 1H), 7.42 (s, 1H), 4.27-4.21 (m, 4H), 4.08-4.03 (m, 4H), 3.84 (s, 3H), 3.82 (s, 3H), 3.74 (s, 2H), 3.32-3.29 (m, 2H), 3.18 (s, 3H), 2.68-2.65 (m, 4H), 2.29-2.26 (m, 2H), 1.23-1.16 (m, 6H).

Example 2: Preparation of 4-(6-(3-((2-((2-carboxyethyl)(methyl)carbamoyl)-5-methoxybenzo[b]thiophen-6-yl)oxy) propoxy)-5-methoxybenzo[b]thiophen-2-yl)-4-oxobutanoic acid (compound 2)

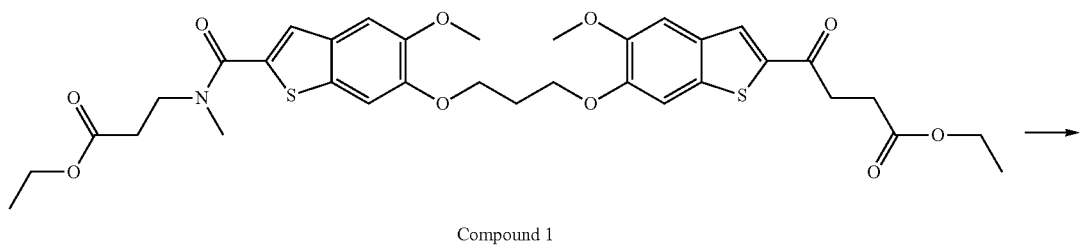

Compound 1

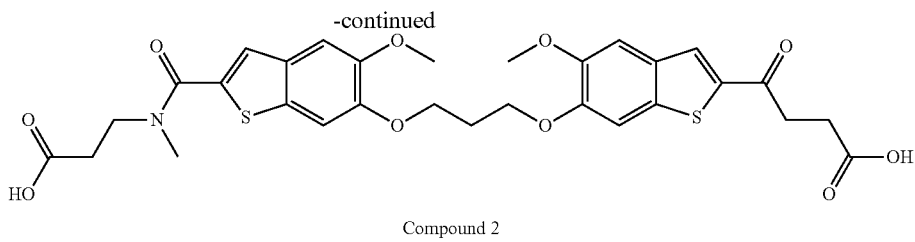

Compound 2

Ethyl 4-(6-(3-((2-((3-ethoxy-3-oxopropyl)(methyl)carbamoyl)-5-methoxybenzo[b]thiophen-6-yl)oxy)propoxy)-5-methoxybenzo[b]thiophen-2-yl)-4-oxobutyrate (compound 1, 80.0 mg, 116.6 μmol) was dissolved in ethanol (10 mL) and water (5 mL). Sodium hydroxide (23 mg, 583.26 μmol) was added. The mixture was heated to 80° C., and then allowed to react for 3 hours. After being cooled to room temperature, the reaction solution was poured into water (50 mL). The resulting mixture was adjusted to pH=2 with dilute hydrochloric acid, and extracted with ethyl acetate (15 mL) for three times. The organic phases were combined, dried with anhydrous sodium sulfate, and filtered. The filtrate was concentrated under reduced pressure, and the concentrate was purified by preparative high performance liquid chromatography to obtain the title compound (55 mg, yield: 75.1%).

MS m/z (ESI): 630.1 [M+H]$^+$.

$^1$H-NMR (400 MHz, DMSO-d$_6$) δ: 12.26 (s, 2H), 8.20 (s, 1H), 7.66-7.61 (m, 3H), 7.49 (s, 1H), 7.42 (s, 1H), 4.27-4.21 (m, 4H), 3.84 (s, 3H), 3.82 (s, 3H), 3.71 (s, 2H), 3.27-3.24 (m, 2H), 3.17 (s, 3H), 2.61-2.58 (m, 4H), 2.29-2.26 (m, 2H).

Example 3: Preparation of ethyl 4-(6-(3-((2-((3-ethoxy-3-oxopropyl)(methyl)carbamoyl)-6-methoxybenzo[b]thiophen-5-yl)oxy)propoxy)-5-methoxybenzo[b]thiophen-2-yl-4-oxobutyrate (compound 3)

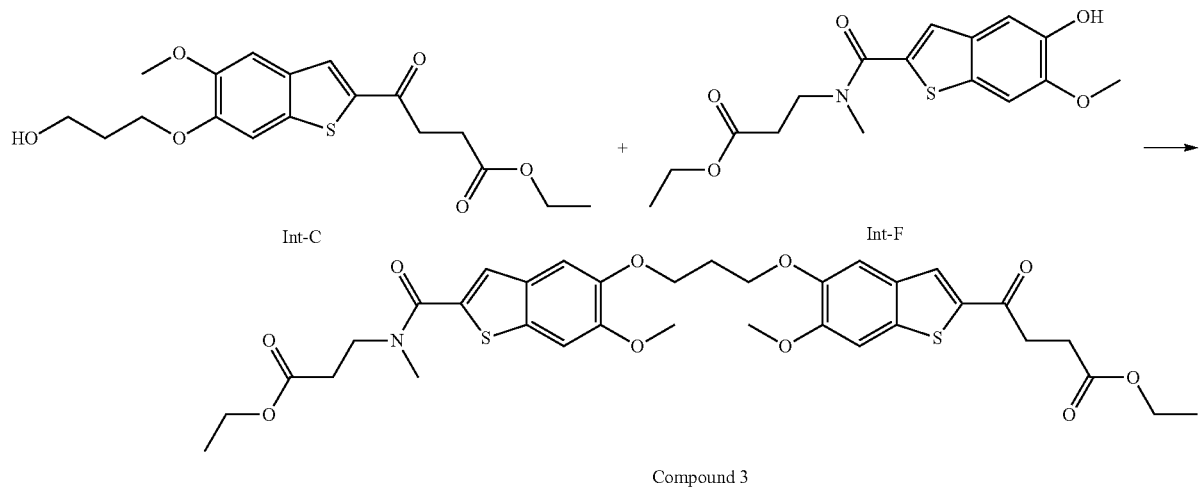

Compound 3

The title compound (67 mg, yield: 60.4%) was obtained using the synthetic route of Example 1, except that the starting material ethyl 3-(N-methyl-6-hydroxy-5-methoxybenzo[b]thiophene-2-formamido)propionate (Int-E) was replaced with ethyl 3-(N-methyl-5-hydroxy-6-methoxybenzo[b]thiophene-2-formamido)propionate (Int-F).

MS m/z (ESI): 686.2 [M+H]$^+$.

$^1$H-NMR (400 MHz, DMSO-d$_6$) δ: 8.21 (s, 1H), 7.67-7.62 (m, 2H), 7.57-7.55 (m, 1H), 7.49-7.42 (m, 2H), 4.26-4.03 (m, 8H), 3.85-3.82 (m, 6H), 3.77-3.74 (m, 2H), 3.33 (s, 3H), 3.31-3.29 (m, 2H), 2.68-2.65 (m, 4H), 2.30-2.23 (m, 2H), 1.28-1.20 (m, 6H).

Example 4: Preparation of 4-(6-(3-((2-((2-carboxyethyl)(methyl)carbamoyl)-6-methoxybenzo[b]thiophen-5-yl)oxy)propoxy)-5-methoxybenzo[b]thiophen-2-yl)-4-oxobutanoic acid (compound 4)

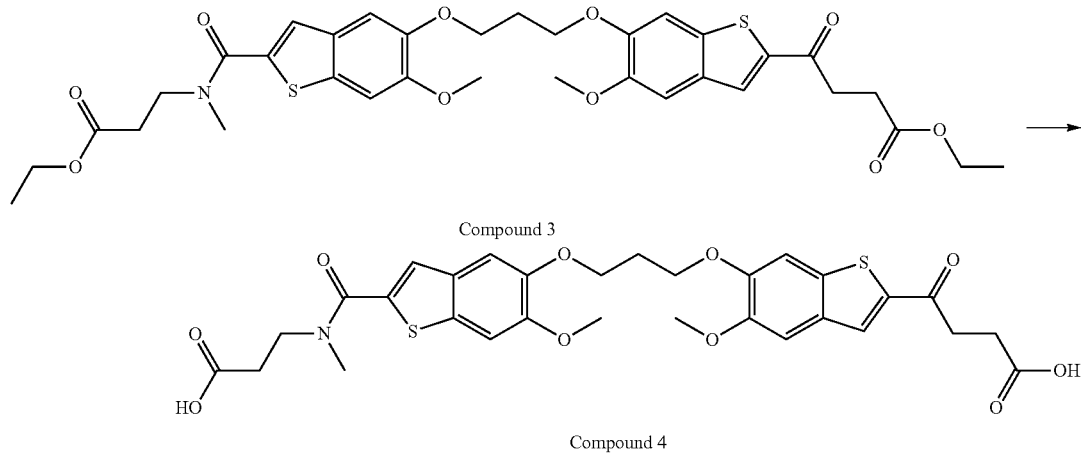

The title compound (29 mg, yield: 68.3%) was obtained using the synthetic route of Example 2, except that the starting material ethyl 4-(6-(3-((2-((3-ethoxy-3-oxopropyl)(methyl)carbamoyl)-5-methoxybenzo[b]thiophen-6-yl)oxy)propoxy)-5-methoxybenzo[b]thiophen-2-yl)-4-oxobutyrate (compound 1) was replaced with ethyl 4-(6-(3-((2-((3-ethoxy-3-oxopropyl)(methyl)carbamoyl)-6-methoxybenzo[b]thiophen-5-yl)oxy)propoxy)-5-methoxybenzo[b]thiophen-2-yl)-4-oxobutyrate (compound 3).

MS m/z (ESI): 630.1 [M+H]$^+$.

$^1$H-NMR (400 MHz, DMSO-d$_6$) δ: 12.29 (s, 2H), 8.20 (s, 1H), 7.66 (s, 1H), 7.62 (s, 1H), 7.56 (s, 1H), 7.49-7.47 (m, 2H), 4.28-4.25 (m, 2H), 4.21-4.18 (m, 2H), 3.84 (s, 6H), 3.70-3.65 (m, 2H), 3.27-3.24 (m, 2H), 3.18 (s, 3H), 2.61-2.58 (m, 4H), 2.33-2.26 (m, 2H).

Example 5: Preparation of ethyl 4-(5-(3-((2-((3-ethoxy-3-oxopropyl)(methyl)carbamoyl)-5-methoxybenzo[b]thiophen-6-yl)oxy)propoxy)-6-methoxybenzo[b]thiophen-2-yl)-4-oxobutyrate (compound 5)

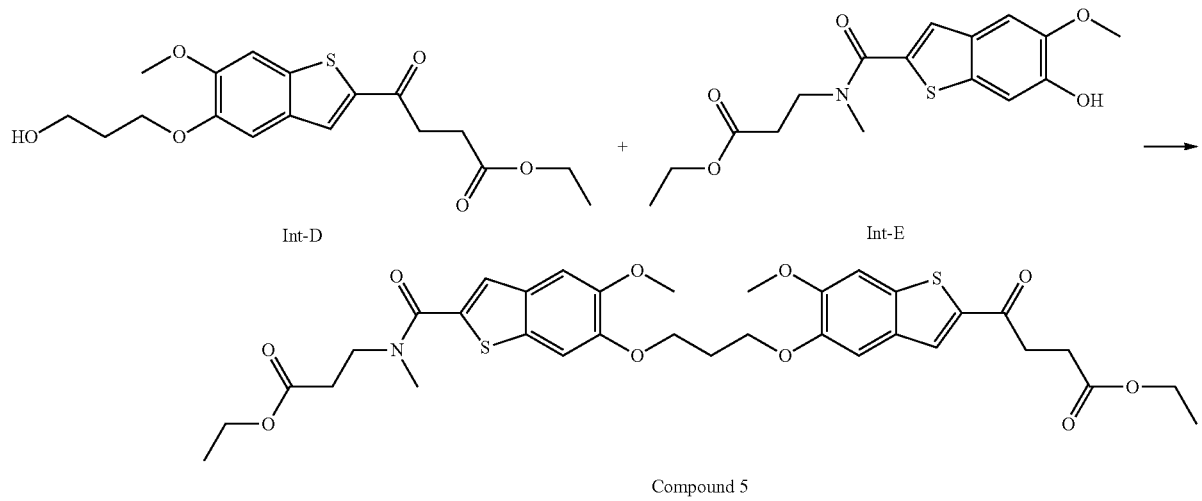

The title compound (56 mg, yield: 59.3%) was obtained using the synthetic route of Example 1, except that the starting material ethyl 4-(6-(3-hydroxypropoxy)-5-methoxybenzo[b]thiophen-2-yl)-4-oxobutyrate (Int-C) was replaced with ethyl 4-(5-(3-hydroxypropoxy)-6-methoxybenzo[b]thiophen-2-yl)-4-oxobutyrate (Int-D).

MS m/z (ESI): 686.2 [M+H]⁺.

¹H-NMR (400 MHz, DMSO-$d_6$) δ: 8.21-8.15 (m, 1H), 7.66-7.65 (m, 1H), 7.62-7.60 (m, 2H), 7.56-7.48 (m, 1H), 7.42 (s, 1H), 4.27-4.20 (m, 4H), 4.09-4.03 (m, 4H), 3.86-3.82 (m, 6H), 3.77-3.74 (m, 2H), 3.30-3.26 (m, 2H), 3.33 (s, 3H), 2.68-2.65 (m, 4H), 2.30-2.27 (m, 2H), 1.24-1.10 (m, 6H).

Example 6: Preparation of 4-(5-(3-((2-((2-carboxyethyl)(methyl)carbamoyl)-5-methoxybenzo[b]thiophen-6-yl)oxy)propoxy)-6-methoxybenzo[b]thiophen-2-yl)-4-oxobutanoic acid (compound 6)

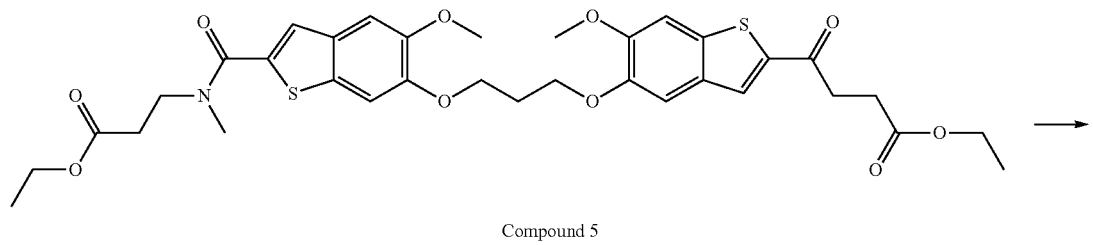

Compound 5

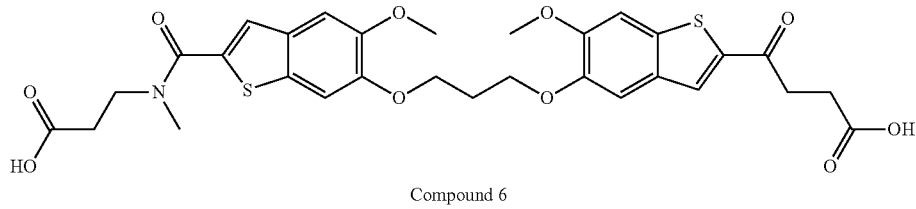

Compound 6

The title compound (26 mg, yield: 66.7%) was obtained using the synthetic route of Example 2, except that the starting material ethyl 4-(6-(3-((2-((3-ethoxy-3-oxopropyl)(methyl)carbamoyl)-5-methoxybenzo[b]thiophen-6-yl)oxy)propoxy)-5-methoxybenzo[b]thiophen-2-yl)-4-oxobutyrate (compound 1) was replaced with ethyl 4-(5-(3-((2-((3-ethoxy-3-oxopropyl)(methyl)carbamoyl)-5-methoxy benzo[b]thiophen-6-yl)oxy)propoxy)-6-methoxybenzo[b]thiophen-2-yl)-4-oxobutyrate (compound 5).

MS m/z (ESI): 630.1 [M+H]⁺.

¹H-NMR (400 MHz, DMSO-$d_6$) δ: 12.28 (s, 2H), 8.20-8.14 (m, 1H), 7.66-7.60 (m, 3H), 7.56-7.48 (m, 1H), 7.42 (s, 1H), 4.27-4.17 (m, 4H), 3.92-3.80 (m, 6H), 3.71 (s, 2H), 3.27-3.24 (m, 2H), 3.18 (s, 3H), 2.62-2.59 (m, 4H), 2.30-2.27 (m, 2H).

Example 7: Preparation of 4-(5-(3-((2-((2-carboxyethyl)(methyl)carbamoyl)-6-methoxybenzo[b]thiophen-5-yl)oxy)propoxy)-6-methoxybenzo[b]thiophen-2-yl)-4-oxobutanoic Acid (Compound 8)

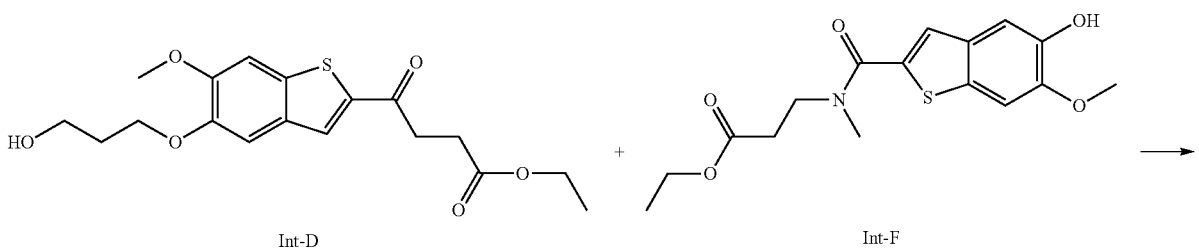

Int-D + Int-F

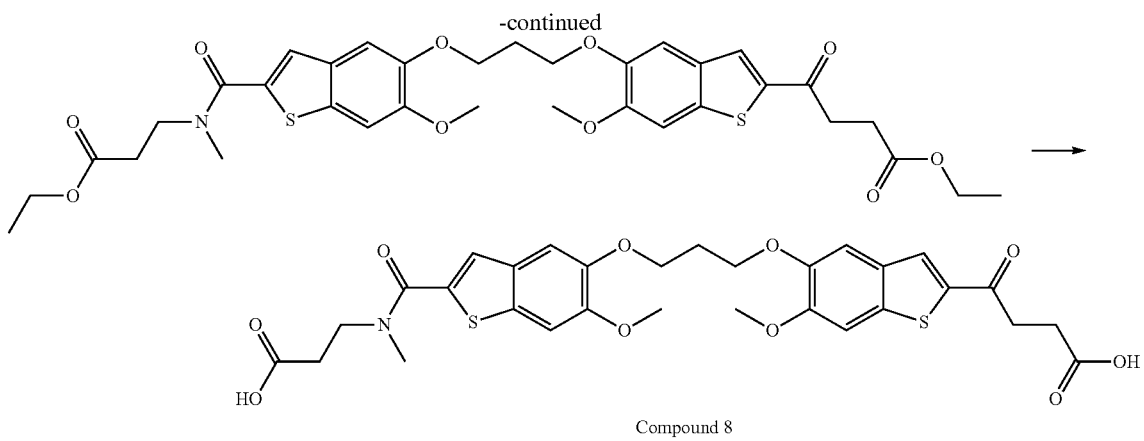

Compound 8

Step 1: Preparation of ethyl 4-(5-(3-((2-((3-ethoxy-3-oxopropyl)(methyl)carbamoyl)-6-methoxy benzo[b]thiophen-5-yl)oxy)propoxy)-6-methoxybenzo[b]thiophen-2-yl)-4-oxobutyrate The title compound (43 mg, yield: 63.6%) was obtained using the synthetic route of Example 1, except that the starting material ethyl 4-(6-(3-hydroxypropoxy)-5-methoxybenzo[b]thiophen-2-yl)-4-oxobutyrate (Int-C) was replaced with ethyl 4-(5-(3-hydroxypropoxy)-6-methoxybenzo[b]thiophen-2-yl)-4-oxobutyrate (Int-D), and the starting material ethyl 3-(N-methyl-6-hydroxy-5-methoxybenzo[b]thiophene-2-formamido)propionate (Int-E) was replaced with ethyl 3-(N-methyl-5-hydroxy-6-methoxybenzo[b]thiophene-2-formamido)propionate (Int-F).

MS m/z (ESI): 686.2 [M+H]$^+$.

Step 2: Preparation of 4-(5-(3-((2-((2-carboxyethyl)(methyl)carbamoyl)-6-methoxybenzo[b]thiophen-5-yl)oxy)propoxy)-6-methoxybenzo[b]thiophen-2-yl)-4-oxobutanoic Acid (Compound 8)

The title compound (26 mg, yield: 67.2%) was obtained using the synthetic route of Example 2, except that the starting material ethyl 4-(6-(3-((2-((3-ethoxy-3-oxopropyl)(methyl)carbamoyl)-5-methoxy benzo[b]thiophen-6-yl)oxy)propoxy)-5-methoxybenzo[b]thiophen-2-yl)-4-oxobutyrate (compound 1) was replaced with ethyl 4-(5-(3-((2-((3-ethoxy-3-oxopropyl)(methyl)carbamoyl)-6-methoxybenzo[b]thiophen-5-yl)oxy)propoxy)-6-methoxybenzo[b]thiophen-2-yl)-4-oxobutyrate.

MS m/z (ESI): 630.1 [M+H].
$^1$H-NMR (400 MHz, DMSO-d$_6$) δ: 12.26 (s, 2H), 8.17 (s, 1H), 7.66-7.60 (m, 2H), 7.56-7.54 (m, 2H), 7.49-7.47 (m, 1H), 4.26-4.20 (m, 4H), 3.86-3.84 (m, 6H), 3.73-3.69 (m, 2H), 3.27-3.24 (m, 2H), 3.19 (s, 3H), 2.61-2.58 (m, 4H), 2.30-2.27 (m, 2H).

Example 8: Preparation of ethyl 4-(6-methoxy-5-(3-((6-methoxy-2-((3-methoxypropyl)(methyl)carbamoyl)benzo[b]thiophen-5-yl)oxy)propoxy)benzo[b]thiophen-2-yl)-4-oxobutyrate (compound 23)

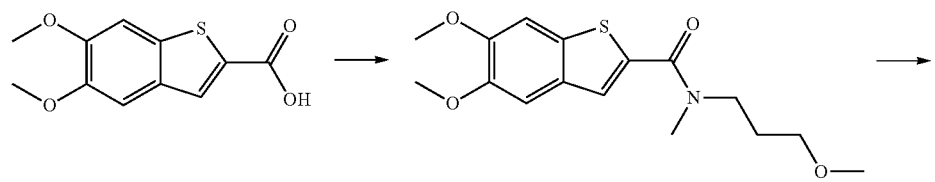

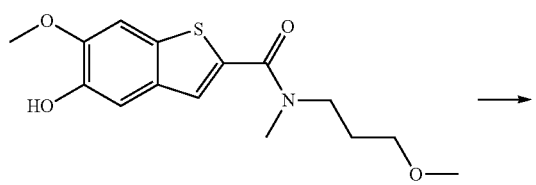

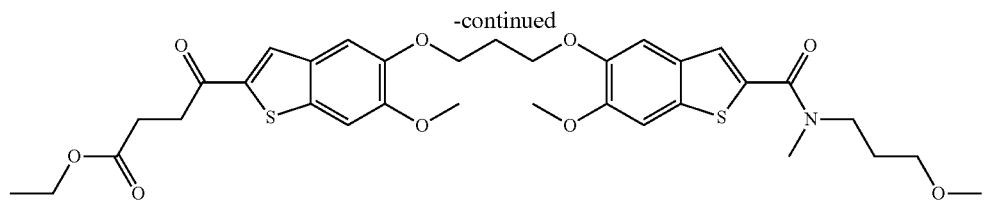

Compound 23

Step 1: Preparation of 5,6-dimethoxy-N-(3-methoxypropyl)-N-methylbenzo[b]thiophene-2-formamide The title compound (823 mg, yield: 72.6%) was obtained using the synthesis method of Step 1 in Intermediate Preparation Example 4, except that the starting material ethyl 3-(methylamino)propionate was replaced with 3-methoxy-N-methyl-1-propylamine.

MS m/z (ESI): 324.1 [M+H]$^+$.

Step 2: Preparation of 5-hydroxy-6-methoxy-N-(3-methoxypropyl)-N-methylbenzo[b]thiophene-2-formamide The title compound (126 mg, yield: 37.5%) was obtained using the synthesis method of Step 2 in Intermediate Preparation Example 4, except that the starting material ethyl 3-(N-methyl-5,6-dimethoxybenzo[b]thiophene-2-formamido)propionate was replaced with 5,6-dimethoxy-N-(3-methoxypropyl)-N-methylbenzo[b]thiophene-2-formamide.

MS m/z (ESI): 310.1 [M+H]$^+$.

Step 3: Preparation of ethyl 4-(6-methoxy-5-(34(6-methoxy-2-((3-methoxypropyl)(methyl)carbamoyl)benzo[b]thiophen-5-yl)oxy)propoxy)benzo[b]thiophen-2-yl)-4-oxobutyrate (compound 23)

The title compound (39 mg, yield: 58.3%) was obtained using the synthetic route of Example 1, except that the starting material ethyl 4-(6-(3-hydroxypropoxy)-5-methoxybenzo[b]thiophen-2-yl)-4-oxobutyrate (Int-C) was replaced with ethyl 4-(5-(3-hydroxypropoxy)-6-methoxybenzo[b]thiophen-2-yl)-4-oxobutyrate (Int-D), and the starting material ethyl 3-(N-methyl-6-hydroxy-5-methoxybenzo[b]thiophene-2-formamido)propionate (Int-E) was replaced with 5-hydroxy-6-methoxy-N-(3-methoxypropyl)-N-methylbenzo[b]thiophene-2-formamide.

MS m/z (ESI): 658.2 [M+H]$^+$.

$^1$H-NMR (400 MHz, DMSO-d$_6$) δ: 8.18 (s, 1H), 7.62-7.61 (m, 2H), 7.56-7.53 (m, 2H), 7.47 (s, 1H), 4.24-4.16 (m, 4H), 4.08-4.03 (m, 2H), 3.87-3.82 (m, 6H), 3.55-3.51 (m, 4H), 3.33 (s, 3H), 2.68-2.65 (m, 5H), 2.30-2.27 (m, 2H), 2.02-1.97 (m, 2H), 1.19-1.16 (m, 3H).

Biological Assays

The control compound 1 used in the following experimental examples, ADU-S100 (1638750-96-5), was purchased from MCE, and the control compound 2,

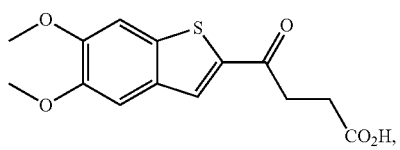 [SMILES: COc1cc2cc(C(=O)CCC(=O)O)sc2cc1OC]

was synthesized according to a prior art method.

Experimental Example 1. The Agonistic Effect of the Compound on the STING-Mediated Interferon (IFN) Signal Reporter Gene in THP1-Blue™ ISG Cells In this experiment, the activity of the SEAP (secreted embryonic alkaline phosphatase) reporter gene regulated by the IFN regulatory factor (interferon regulatory factor) was detected in the THP1-Blue™ ISG cells (InvivoGen) to evaluate the agonistic effect of the compounds to be tested on the STING-mediated IFN signal pathway at the cellular level.

The THP1-Blue™ ISG cells (InvivoGen) in the logarithmic phase were centrifuged, and resuspended in a cell culture solution to a density of 2×10$^6$ cells/ml. The cell suspension was inoculated in a 96-well cell culture plate (Corning) at 50 μL/well. The mother liquor of the compound to be tested was gradiently diluted with a cell culture solution to obtain a 2× working concentration diluted solution (control compounds 1 and 2 were diluted at a 3-fold gradient: 200, 66.67, 22.22, 7.41, 2.47, 0.82, 0.27 and 0 μM; compounds 1, 2, 4, 6, 8, and 23 were diluted at a 8-fold gradient: 60, 7.5, 0.94, 0.12, 0.015, 0.0018, 0.00023 and 0 μM; and compounds 3 and 5 were diluted at a 10-fold gradient: 10, 1, 0.1, 0.01, 0.001, 0.0001, 0.00001 and 0 μM). The 2× working concentration diluted solution of the compound was added into a 96-well plate (50 μl of the culture solution containing 2% DMSO was added into the negative control well) at 50 μL/well. The culture plate was then placed in a cell incubator, and incubated for 16 h. After the cell incubation, 10 μL of the cell culture supernatant was transferred to a 96-well plate, and a QUANTI-Blue (InvivoGen) solution was added at 90 μL/well. The cells were incubated at 37° C. for 3 h. The absorbance at 620 nm (OD$_{620nm}$) was read with a microplate reader. EC$_{50}$ was calculated through fitting by the Graphpad Prism software, and the experimental results are shown in Table 1.

TABLE 1

The agonistic effect of the tes compounds on the STING-mediated interferon (IFN) signal reporter gene

| Compound No. | EC$_{50}$ (μM) | E$_{max}$ (OD$_{620nm}$) |
|---|---|---|
| 1 | 0.00057 | 1.54 |
| 2 | 0.457 | 1.82 |
| 3 | 0.00358 | 1.92 |
| 4 | 0.03546 | 1.97 |
| 5 | 0.0014 | 1.94 |
| 6 | 0.0745 | 1.88 |
| 8 | 0.05534 | 1.73 |
| 23 | 0.9743 | 1.74 |

TABLE 1-continued

The agonistic effect of the tes compounds on the STING-mediated interferon (IFN) signal reporter gene

| Compound No. | $EC_{50}$ (μM) | $E_{max}$ ($OD_{620nm}$) |
|---|---|---|
| Control Compound 1 | 3.88 | 2.03 |
| Control Compound 2 | 4.95 | 1.49 |

In the table, $EC_{50}$ refers to the concentration of a compound when $ODM_{620nm}$ value generated by stimulation of the compound reaches half of $E_{max}$; and $E_{max}$ refers to the highest $OD_{620nm}$ value generated by stimulation of the compound.

The results showed that compounds 1, 2, 3, 4, 5, 6, 8 and 23 have strong agonistic effects on the STING-mediated Interferon (IFN) signal pathway in THP1-Blue™ ISG cells.

Experimental Example 2. The Agonistic Effect of the Compound on the Phosphorylation of the STING Signal Pathway Protein in Human THP-1 Cells In this experiment, the changes in the phosphorylation levels of STING and its downstream proteins TBK1 (TANK-binding kinase 1) and IRF3 (interferon regulatory factor 3) were detected by protein blotting to evaluate the agonistic effect of the test compounds on the STING signal pathway at the cellular level.

The THP-1 cells in the logarithmic phase were centrifuged, and resuspended in a cell culture solution to a density of $4\times10^1$ cells/mL. The cell suspension was inoculated into a 12-well cell culture plate (Corning) at 0.5 mL/well. The compound to be tested was diluted with a cell culture solution to 2× working solution concentration (control compounds 1 and 2: 60 μM; compounds 1 and 3: 0.6 μM, 6 μM, and 60 μM; compounds 2, 4, 6 and 8: 6 μM, 20 μM, and 60 μM). 0.5 mL of the diluted solution of the compound was added into a 12-well plate (500 μl of the culture solution containing 2% DMSO was added into the negative control well), and the plate was incubated in a cell incubator for 3 hours. After the incubation, the cells were collected by centrifugation, lysed with 60 μL cell lysis buffer (CST) for 30 minutes, and centrifuged at 12,000 rpm for 15 minutes. The supernatant was collected to determine the protein concentration, and then an appropriate amount of 5× protein loading buffer was added. The mixture was heated at 95° C. for 10 minutes to prepare a protein electrophoresis sample. Finally protein blotting was performed to detect the phosphorylation level of the corresponding protein. The experimental results are shown in FIGS. 1-5. The primary antibodies used in the protein blotting were purchased from CST: STING (D2P2F) rabbit mAb, Phospho-STING (Ser366) rabbit mAb, Phospho-IRF3 (Ser396) (D601M) rabbit mAb, IRF3 (D83B9) rabbit mAb, TBK1/NAK (D1B4) rabbit mAb, Phospho-TBK1/NAK (Ser172) (D52C2) XP® rabbit mAb, and GAPDH (D16H11) rabbit mAb; and the secondary antibody horseradish peroxidase-conjugated goat anti-rabbit IgG (H+L) was purchased from Zsgb-bio.

As shown in FIGS. 1-5, compounds 1, 2, 3, 4, 6 and 8 have strong agonistic effects on the phosphorylation levels of STING and its downstream proteins TBK1 and IRF3 in THP-1 cells.

Experimental Example 3. The Agonistic Effect of the Compound on the Expression of STING Signal Pathway Cytokine hIFN-β in Human THP-1 Cells In this experiment, the expression of STING signal pathway cytokine hIFN-β was detected in THP1 cells (Nanjing Cobioer) by the ELISA method, so as to evaluate the agonistic effect of the compounds to be tested on the expression of STING pathway cytokine hIFN-β at the cellular level.

THP1 cells (Nanjing Cobioer) in the logarithmic phase were centrifuged, and resuspended in a cell culture solution to a density of $8\times10^6$ cells/ml. The cell suspension was inoculated into a 24-well cell culture plate (Corning) at 250 μL/well.

The mother liquor of the compound to be tested was diluted with a cell culture solution to obtain a 2× working concentration diluted solution (control compounds 1 and 2 were diluted at a 2-fold gradient: 200, 100, 50, 25, 12.5, 6.25, 3.125, 1.5625 and 0 μM; and compounds 4, 6, and 8 were diluted at a 3-fold gradient: 200, 66.67, 22.22, 7.41, 2.47, 0.82, 0.27, 0.091 and 0 μM). The 2× working concentration diluted solution of the compound was added into 24-well plate (250 μl of the culture solution containing 2% DMSO was added into the negative control well) at 250 μL/well. The culture plate was placed in a cell culture incubator, and incubated for 8 hours. After the cell incubation, the supernatant was collected by centrifugation at 300 g×5 min, and the hIFN-β content (pg/ml) in the cell culture supernatant was detected according to the operating instructions of the VeriKine Human IFN-0 ELISA kit from PBL (obtained by conversion of the $OD_{410\ nm}$ absorbance-hIFN-β standard concentration standard curve and the $OD_{450\ nm}$ absorbance value read by the microplate reader). ECs was calculated through log(agonist) vs. response—Variable slope fitting by the Graphpad Prism software, and the experimental results are shown in Table 2.

TABLE 2

The agonistic effect of the test compounds on the expression of the STING pathway cytokine hIFN-β in human THP-1 cells

| Compound No. | $EC_{50}$ (μM) | $E_{max}$ (pg/ml) |
|---|---|---|
| 4 | 5.57 | 908.0 |
| 6 | 1.82 | 829.6 |
| 8 | 1.25 | 917.1 |
| Control Compound 1 | 13.99 | 1476.6 |
| Control Compound 2 | 16.83 | 1373.9 |

In the table, $EC_{50}$ refers to the concentration of a compound when the expression of hIFN-β generated by stimulation of the compound reaches half of $E_{max}$ and $E_{max}$ refers to the highest expression of hIFN-β generated by stimulation of the compound.

The results show that compounds 4, 6 and 8 have a strong agonistic effect on the expression of the STING pathway cytokine hIFN-β in human THP-1 cells.

Experimental Example 4. The Agonistic Effect of the Compound on the Phosphorylation of STING Signal Pathway Protein in Mouse Raw264.7 Cells In this experiment, the changes in the phosphorylation levels of STING and its downstream proteins TBK1 (TANK-binding kinase 1) and IRF3 (interferon regulatory factor 3) were detected by protein blotting to evaluate the agonistic effect of the test compounds on the STING signal pathway at the cellular level.

Figure 6:
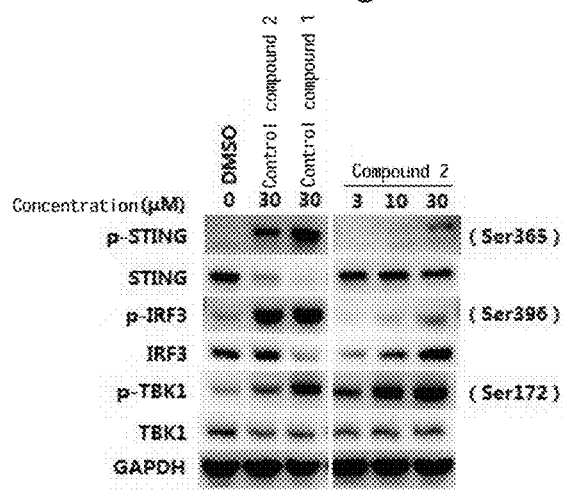
FIG. 6 is a graph showing the experimental results of Western blotting of STING signaling pathway proteins in mouse Raw264.7 cells using compound 2.
Figure 7:
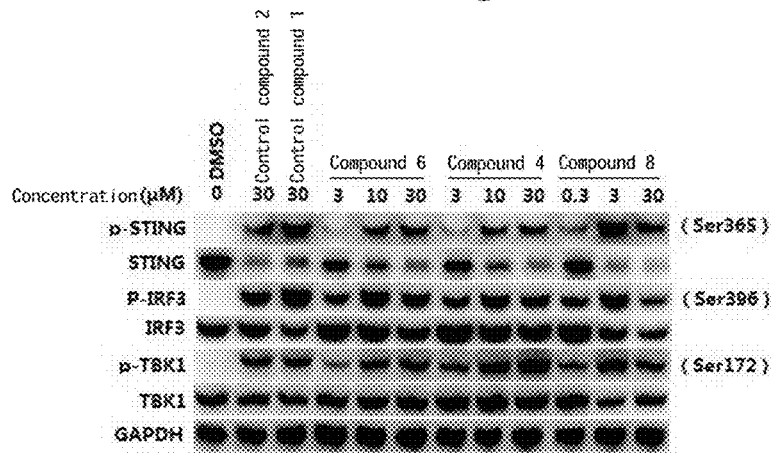
FIG. 7 is a graph showing the experimental results of Western blotting of STING signaling pathway proteins in mouse Raw264.7 cells using compounds 4, 6 and 8.

The Raw264.7 cells in the logarithmic phase were centrifuged, and resuspended in a cell culture solution to a density of $1.6 \times 10^6$ cells/mL. The cell suspension was inoculated into a 6-well cell culture plate (Corning) at 1 mL/well. The compound to be tested was diluted with a cell culture solution to 2× working solution concentration (control compounds 1 and 2: 60 µM; compound 8: 0.6 µM, 6 µM, and 60 µM; compounds 2, 4 and 6: 6 µM, 20 µM, and 60 µM). 1 mL of the diluted solution of the compound was added into a 6-well plate (1 mL of the culture solution containing 2% DMSO was added into the negative control well). The plate was placed in a cell incubator, and incubated for 3 hours. After the incubation, the cells were collected by centrifugation, lysed with 60 µL cell lysis buffer (CST) for 30 minutes, and centrifuged at 12000 rpm for 15 minutes. The supernatant was collected to determine the protein concentration, and then an appropriate amount of 5× protein loading buffer was added. The mixture was heated at 95° C. for 10 minutes to prepare a protein electrophoresis sample. Finally, protein blotting was performed to detect the phosphorylation level of the corresponding protein. The experimental results are shown in FIGS. 6-7. The primary antibodies used in the protein blotting were purchased from CST: STING (D2P2F) rabbit mAb, Phospho-STING (Ser365) rabbit mAb, Phospho-IRF3 (Ser396) (D601M) rabbit mAb, IRF3 (D83B9) rabbit mAb, TBK1/NAK (D1B4) rabbit mAb, Phospho-TBK1/NAK (Ser172) (D52C2) XPV rabbit mAb, GAPDH (D16H11) rabbit mAb; and the secondary antibody horseradish peroxidase-conjugated goat anti-rabbit IgG (H+L) was purchased from Zsgb-bio.

As shown in FIGS. 6-7, compounds 2, 4, 6 and 8 have strong agonistic effects on the phosphorylation levels of STING and its downstream proteins TBK1 and IRF3 in Raw264.7 cells.

Experimental Example 5. The Agonistic Effect of the Compound on the Expression of STING Pathway Cytokine mIFN-β in Mouse Raw264.7 Cells In this experiment, the expression of STING signal pathway cytokine mIFN-β was detected in Raw264.7 cells (Nanjing Cobioer) by the ELISA method, so as to evaluate the agonistic effect of the compound to be tested on the expression of STING pathway cytokine mIFN-β at the cellular level.

Raw264.7 cells (Nanjing Cobioer) in the logarithmic phase were centrifuged, and resuspended in a cell culture solution to a density of $1.6 \times 10^6$ cells/ml. The cell suspension was inoculated into a 24-well cell culture plate (Corning) at 250 µL/well. The mother liquor of the compound to be tested was gradiently diluted with a cell culture solution to obtain a 2× working concentration diluted solution (control compound 1 was diluted at a 3-fold gradient: 200, 66.67, 22.22, 7.41, 2.47, 0.82, 0.27 and 0 µM; control compound 2 was diluted at a 2-fold gradient: 200, 100, 50, 25, 12.5, 6.25, 3.125 and 0 µM; and compounds 4, 6 and 8 were diluted at a 4-fold gradient: 200, 50, 12.5, 3.13, 0.78, 0.20, 0.049 and 0 µM). The 2× working concentration diluted solution of the compound was added into a 24-well plate (250 µl of the culture solution containing 2% DMSO was added into the negative control well) at 250 µL/well. The culture plate was then placed in a cell incubator, and incubated for 6 h. After the cell incubation, the supernatant was collected by centrifugation at 300 g×5 min, and the mIFN-β content (pg/ml) in the cell culture supernatant was detected according to the operating instructions of the VeriKinem Mouse IFN Beta ELISA Kit from PBL (obtained by conversion of the $OD_{450\ nm}$ absorbance-mIFN-β standard concentration standard curve and the $OD_{450\ nm}$ absorbance value read by the microplate reader). $EC_{50}$ was calculated through log(agonist) vs. response—Variable slope fitting by the Graphpad Prism software, and the experimental results are shown in Table 3.

TABLE 3

The agonistic effect of the test compounds on the expression of the STING pathway cytokine mIFN-β in mouse Raw264.7 cells

| Compound No. | $EC_{50}$ (µM) | $E_{max}$ (pg/ml) |
|---|---|---|
| 4 | 3.60 | 1082.21 |
| 6 | 3.80 | 1012.51 |
| 8 | 0.56 | 1176.75 |
| Control Compound 1 | 2.74 | 1248.94 |
| Control Compound 2 | 24.60 | 1106.15 |

In the table, $EC_{50}$ refers to the concentration of a compound when the expression of mIFN-β generated by stimulation of the compound reaches half of $E_{max}$; and $E_{max}$ refers to the highest expression of mIFN-β generated by stimulation of the compound.

The results show that compounds 4, 6 and 8 have a strong agonistic effect on the expression of the STING pathway cytokine mIFN-β in mouse Raw264.7 cells.

Experimental Example 6. The Assay Detecting the Binding Affinity Between the Compound and hSTING Protein In this experiment, the capability of the compound and the specific ligand (d2-STING-ligand) in a Human STING binding kit from Cisbio for competitively binding to the 6×His-hSTING protein was detected using the Human STING binding kit (HTRF method), so as to evaluate the binding affinity between the compound to be tested and the hSTING protein.

The compound was gradiently diluted with a dilution buffer in the Human STING binding kit (the diluent buffer reagent) to obtain a 4× working concentration diluted solution. 5 µl of the diluted solution was added into a 384-well plate to ensure that the final concentration of DMSO in the reaction system was ≤2.5%. The 6×His-hSTING protein (50× in the mother liquor) was diluted to 1× with the detection buffer in the Human STING binding kit (the detection buffer reagent). 5 µl of the diluted solution was added into the corresponding wells of a 384-well plate, and the well with no protein and no compound was set as a negative control well (min), while the well with the protein and no compound was set as a positive control well (max). The d2-STING-ligand and $Tb^{3+}$-anti-6×His-antibody (both 50× in the mother liquor) were diluted to 1× with the detection buffer in the Human STING binding kit (the detection buffer reagent), and mixed uniformly at a ratio of 1:1. 10 µl of the mixed solution was added to the corresponding wells of a 384-well plate. The plate was sealed and incubated at room temperature (25° C.) for 3 h. A BMG microplate reader was used to read HTRF, and the ratio was calculated according to the following formula: Ratio=$signal_{665nm}/signal_{620nm} \times 10000$. The inhibition rate of the compound was calculated according to the following formula: IR (%)=$(R_{max}-R_t)/(R_{max}-R_{min})*100\%$, wherein $R_{max}$ was the HTRF reading ratio of the positive control well, $R_{min}$ was the HTRF reading ratio of the negative control well, and $R_t$ was the HTRF reading ratio of the corresponding compound treatment well. $IC_{50}$ was calculated through log(inhibitor) vs. response—Variable slope fitting by the Graphpad Prism software. $K_i$ was calculated according to the parameter formula ($K_i=1/2*IC_{50}$) provided in the instructions of the Human STING binding kit. The experimental results are shown in Table 4.

TABLE 4

The binding affinity between the test compounds and hSTING protein

| Compound No. | $IC_{50}$ (nM) | $K_i$ (nM) |
|---|---|---|
| 4 | 32.24 | 16.12 |
| 6 | 9.10 | 4.55 |
| 8 | 0.139 | 0.069 |
| Control Compound 1 | 948.6 | 474.3 |
| Control Compound 2 | 3782 | 1891 |

The results show that compounds 4, 6 and 8 have strong binding affinity to the hSTING protein.

Experimental Example 7: The In Vivo Efficacy of the Compound in the MC38 Mouse Colon Cancer Allograft Tumor Model In this experimental example, the changes in tumor volume and tumor weight of an MC38 mouse colon cancer transplanted tumor model were measured and recorded after intratumoral injection (i.t.) of compound 6 or compound 8, so as to test the efficacy of each test compound.

1. Experimental Cell Strain and Experimental Animals

Experimental cell strain: Mouse colon cancer MC38 cells (Nanjing Cobioer) were cultured in a 37° C., 5% $CO_2$ incubator (medium: RPMI-1640 (Hyclone) containing 10% fetal bovine serum (Gibco)). Trypsin-EDTA (Hyclone) was used for routine digestion and passage. When the cells were in the exponential phase with a saturation of 80%-900%, the cells were collected and counted.

Experimental animals: C57BL/6J mice, 6-8 weeks old, female, weighing 18-20 grams. All mice were purchased from Beijing Vital River Laboratory Animal Technology Co., Ltd., and kept in a special pathogen-free (SPF) animal room.

2. Seeding and Grouping of Tumor Cells

The MC38 cells were resuspended in phosphate buffered saline (PBS) at a density of $5\times10^6$ cells/mL. 0.1 mL of PBS (containing $5\times10^5$ MC38 cells) was inoculated subcutaneously at the position of scapula at the right and left back of each mouse. When the average volume of the tumors at the left and right sides reached about 100 mm$^3$, the mice were randomly grouped according to the volumes of the tumors at the left and right sides.

3. Experimental Method

When the average volume of the subcutaneously transplanted tumors reached about 100 mm$^3$, the mice were randomly grouped according to the volume of the tumors at the left and right sides, with 8 in each group. Administration was performed on the tumors at the right side via intratumoral injection at an administration frequency of BIW×2 for 2 weeks in total, while no administration was performed on the tumors at the left side. The specific dosage regimen is shown in Table 5. After administration, the volumes of tumors at the left and right sides were measured twice a week, and the death of the animals was observed every day.

4. Experimental Indicators and Statistical Analysis

The anti-tumor efficacy of the test compound was evaluated by the tumor volume inhibitory rate $TGI_{volume}$ (%). The tumor volume was measured with a vernier caliper. The tumor volume is calculated according to the formula: $V=0.5\times a\times b^2$, wherein "a" and "b" represent the long diameter and short diameter of the tumor, respectively. The tumor volume inhibitory rate $TGI_{volume}$ (%)=[(1−(the average tumor volume at the end of dosing to a dosing group−the average tumor volume at the start of dosing to the dosing group)/(the average tumor volume at the end of dosing to a vehicle control group−the average tumor volume at the start of dosing to the vehicle control group)]×100%. When the tumor volume at the end of dosing was smaller than the tumor volume at the start of dosing (i.e., tumor regression), $TGI_{volume}$ (%)=[1−(the average tumor volume at the end of dosing to a dosing group−average the tumor volume at the start of dosing to the dosing group)/the average tumor volume at the start of dosing to the dosing group]×100%.

A statistical analysis was performed based on the tumor volume at the end of the experiment using the Graphpad Prism software. A comparison between the two groups was analyzed by Student's t-test. When P<0.05, it was considered as having a significant difference.

TABLE 5

The dosage regimen of the test compounds

| Group | Compound No. | Unit dose | Dosing volume (μL/animal) |
|---|---|---|---|
| 1 | Vehicle (physiological saline) | — | 25 |
| 2 | 6 | 10 μg | 25 |
| 3 | 8 | 10 μg | 25 |

5. Test Results

After 2 weeks of administration, the body weights of the animals in each dosage group were increased, and no animal died. See Table 6 for the test results of the tumor volume and tumor inhibitory effect in mice.

The experimental results showed that when compound 6 was injected intratumorally at a unit dose of 10 μg (i.t., BIW×2), it had a significant tumor inhibitory effect on the tumors at the dosing side of the model (the TGI at Day 18 after administration was 106.24% (P=0.0007)), and also had a tumor inhibitory effect on tumors at the non-dosing side (the TGI was 51.09% (P=0.055)). When compound 8 was injected intratumorally at a unit dose of 10 μg (i.t., BIW×2), it had a significant tumor inhibitory effect on the tumors at both the dosing side and the non-dosing side of the model. On Day 18 after administration, the TGI at the dosing side was 200.00% (P=0.0006), and the TGI at the non-dosing side was 58.09% (P=0.025).

TABLE 6

The tumor inhibitory effect (tumor volume) of test compounds 6 and 8 on the MC38 allograft tumor model on different days of administration

| | Day 0 | | Day 18 | | | |
|---|---|---|---|---|---|---|
| | Dosing side | Non-dosing side | Dosing side | | Non-dosing side | |
| Group | Tumor Volume$^a$ (mm$^3$) | Tumor Volume$^a$ (mm$^3$) | Tumor Volume$^a$ (mm$^3$) | TGI$_{volume}$$^b$ (%) | Tumor Volume$^a$ (mm$^3$) | TGI$_{volume}$$^b$ (%) |
| Vehicle (physiological saline) | 113.29 ± 9.37 | 95.33 ± 13.22 | 1443.44 ± 243.29 | — | 1454.20 ± 274.52 | — |
| Compound 6 | 112.09 ± 11.95 | 96.07 ± 10.17 | 105.10 ± 74.74 | 106.24 | 760.69 ± 174.22 | 51.09 |
| Compound 8 | 113.24 ± 12.33 | 96.60 ± 11.50 | 0.00 ± 0.00 | 200.00 | 666.08 ± 100.92 | 58.09 |

Note:
$^a$Tumor volume (mm$^3$) = mean ± standard error (SEM), n = 8.
$^b$The tumor volume inhibitory rate TGI$_{volume}$(%) = [(1 − (the average tumor volume at the end of dosing to a dosing group − the average tumor volume at the start of dosing to the dosing group)/(the average tumor volume at the end of dosing to a vehicle control group − the average tumor volume at the start of dosing to the vehicle control group))] × 100%. When tumor regression occurs (that is, the tumor volume at the end of dosing was smaller than the tumor volume at the start of dosing), TGI$_{volume}$(%) = [1 − (the average tumor volume at the end of dosing to a dosing group − the average tumor volume at the start of dosing to the dosing group)/the average tumor volume at the start of dosing to the dosing group] × 100%.

What is claimed is:
1. A compound of formula (I):

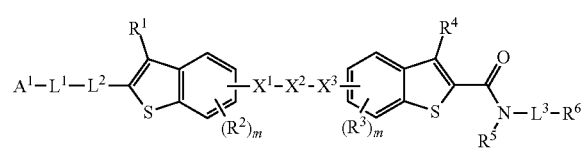

I wherein
both $X^1$ and $X^3$ are —O—;
$X^2$ is $C_{1-6}$ alkylene, wherein the $C_{1-6}$ alkylene, is optionally substituted with one or more substituents independently selected from the group consisting of halogen, cyano, hydroxy, $C_{1-6}$ alkyl and $C_{1-6}$ alkoxy;
$L^1$ is —$(C(R^8)_2)_p$—;
$L^2$ is —C(O)—;
$L^3$ is —$(C(R^9)_2)_q$—;
$A^1$ is —C(O)—OR$^a$;
$R^1$ and $R^4$ are H;
$R^2$ and $R^3$ are the same or different, and are each independently selected from the group consisting of H, halogen, cyano, —OR$^a$, —SR$^a$, —S(O)R$^a$, —S(O)$_2$R$^a$, —NR$^a$R$^b$, —C(O)—NR$^a$R$^b$, —NR$^a$—C(O)—R$^a$, $C_{1-6}$ alkyl, $C_{2-6}$ alkenyl, $C_{2-6}$ alkynyl, $C_{3-6}$ cycloalkyl, 3-6 membered heterocyclyl, $C_{6-10}$ aryl and 5-10 membered heteroaryl, wherein the $C_{1-6}$ alkyl, $C_{2-6}$ alkenyl, $C_{2-6}$ alkynyl, $C_{3-6}$ cycloalkyl, 3-6 membered heterocyclyl, $C_{6-10}$ aryl and 5-10 membered heteroaryl are each optionally substituted with one or more substituents independently selected from the group consisting of halogen, $C_{1-6}$ alkyl, $C_{1-6}$ haloalkyl, cyano, hydroxy and $C_{1-6}$ alkoxy;
$R^5$ is selected from the group consisting of H, $C_{1-6}$ alkyl, $C_{3-10}$ cycloalkyl and 3-10 membered heterocyclyl, wherein the $C_{1-6}$ alkyl, $C_{3-10}$ cycloalkyl and 3-10 membered heterocyclyl are each optionally substituted with one or more substituents independently selected from the group consisting of halogen, cyano, hydroxy, $C_{1-6}$ alkyl, $C_{3-10}$ cycloalkyl, 3-10 membered heterocyclyl, $C_{1-6}$ haloalkyl, $C_{1-6}$ alkoxy, $C_{1-6}$ haloalkoxy, —NR$^a$R$^b$, —CO$_2$R$^a$ and —S(O)$_2$R$^a$;
$R^6$ is OR$^a$ or —C(O)$_2$R$^7$;
$R^7$ is selected from the group consisting of H and $C_{1-6}$ alkyl;
$R^8$ is each independently selected from the group consisting of H and $C_{1-6}$ alkyl;
$R^9$ is each independently selected from the group consisting of H and $C_{1-6}$ alkyl;
$R^a$ and $R^b$ are each independently selected from the group consisting of H and $C_{1-6}$ alkyl wherein the $C_{1-6}$ alkyl is optionally substituted with one or more substituents independently selected from the group consisting of hydroxy, halogen and $C_{1-6}$ alkyl;
m and n are each independently selected from the group consisting of 0, 1, 2 and 3; and
p and q are each independently selected from the group consisting of 1, 2, and 3,
or a pharmaceutically acceptable salt, a stereoisomer, a tautomer, a polymorph, a solvate, an N-oxide, or an isotope-labeled compound thereof.

2. The compound according to claim 1, wherein
$X^2$ is unsubstituted $C_{1-4}$ alkylene;
or a pharmaceutically acceptable salt, a stereoisomer, a tautomer, a polymorph, a solvate, an N-oxide, or an isotope-labeled compound thereof.

3. The compound according to claim 1, wherein
$L^1$ is —(CH$_2$)$_2$—,
or a pharmaceutically acceptable salt, a stereoisomer, a tautomer, a polymorph, a solvate, an N-oxide, or an isotope-labeled compound thereof.

4. The compound according to claim 1, wherein
$L^3$ is —CH$_2$, —(CH$_2$)$_2$— or —(CH$_2$)$_3$—,
or a pharmaceutically acceptable salt, a stereoisomer, a tautomer, a polymorph, a solvate, an N-oxide, or an isotope-labeled compound thereof.

5. The compound according to claim 1, wherein
$A^1$ is selected from the group consisting of —C(O)—OH and —C(O)—O—(CH$_2$CH$_3$),
or a pharmaceutically acceptable salt, a stereoisomer, a tautomer, a polymorph, a solvate, an N-oxide, or an isotope-labeled compound thereof.

6. The compound according to claim 1, wherein R² and R³ are the same or different, and are each independently selected from the group consisting of H, halogen and —OR$^a$;

or a pharmaceutically acceptable salt, a stereoisomer, a tautomer, a polymorph, a solvate, an N-oxide, or an isotope-labeled compound thereof.

7. The compound according to claim 1, wherein R⁵ is selected from the group consisting of H, $C_{1-6}$ alkyl, and $C_{3-6}$ cycloalkyl;

or a pharmaceutically acceptable salt, a stereoisomer, a tautomer, a polymorph, a solvate, an N-oxide, or an isotope-labeled compound thereof.

8. The compound according to claim 1, wherein R⁶ is selected from the group consisting of —O($C_{1-6}$ alkyl), —C(O)₂H and —C(O)₂—($C_{1-6}$ alkyl);

or a pharmaceutically acceptable salt, a stereoisomer, a tautomer, a polymorph, a solvate, an N-oxide, or an isotope-labeled compound thereof.

9. The compound according to claim 1, wherein m and n are each independently selected from the group consisting of 0 and 1;

or a pharmaceutically acceptable salt, a stereoisomer, a tautomer, a polymorph, a solvate, an N-oxide, or an isotope-labeled compound thereof.

10. The compound according to claim 1, wherein the compound has a structure of formula (III):

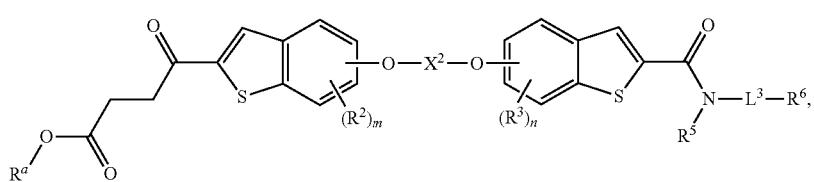

or a pharmaceutically acceptable salt, a stereoisomer, a tautomer, a polymorph, a solvate, an N-oxide, or an isotope-labeled compound thereof.

11. The compound according to claim 10, wherein the compound has a structure of formula (III-1):

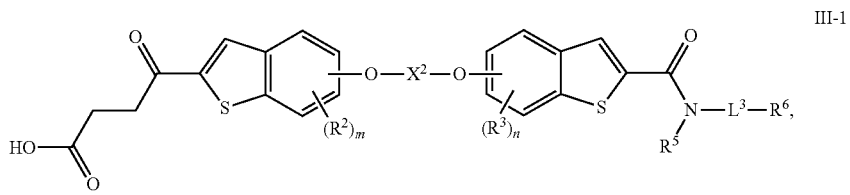

or a pharmaceutically acceptable salt, a stereoisomer, a tautomer, a polymorph, a solvate, an N-oxide, or an isotope-labeled compound thereof.

12. The compound according to claim 10, wherein the compound has a structure of formula (IV):

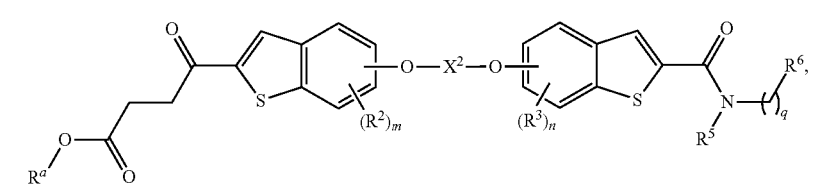

or a pharmaceutically acceptable salt, a stereoisomer, a tautomer, a polymorph, a solvate, an N-oxide, or an isotope-labeled compound thereof.

13. The compound according to claim 2, wherein
$X^2$ is propylene;
or a pharmaceutically acceptable salt, a stereoisomer, a tautomer, a polymorph, a solvate, an N-oxide, or an isotope-labeled compound thereof.

14. The compound according to claim 6, wherein
$R^2$ and $R^3$ are the same or different, and are each independently selected from the group consisting of —OH and —O($C_{1-6}$ alkyl), wherein the $C_{1-6}$ alkyl in the —O($C_{1-6}$ alkyl) is optionally substituted with one or more substituents selected from the group consisting of halogen, hydroxy and $C_{1-6}$ alkyl;
or a pharmaceutically acceptable salt, a stereoisomer, a tautomer, a polymorph, a solvate, an N-oxide, or an isotope-labeled compound thereof.

15. The compound according to claim 14, wherein
$R^2$ and $R^3$ are the same or different, and are each independently selected from the group consisting of methoxy, 2-hydroxy-2-methylpropoxy and 3-hydroxy-3-methylbutoxy;
or a pharmaceutically acceptable salt, a stereoisomer, a tautomer, a polymorph, a solvate, an N-oxide, or an isotope-labeled compound thereof.

16. The compound according to claim 7, wherein
$R^5$ is $C_{1-6}$ alkyl;
or a pharmaceutically acceptable salt, a stereoisomer, a tautomer, a polymorph, a solvate, an N-oxide, or an isotope-labeled compound thereof.

17. The compound according to claim 16, wherein
$R^5$ is methyl;
or a pharmaceutically acceptable salt, a stereoisomer, a tautomer, a polymorph, a solvate, an N-oxide, or an isotope-labeled compound thereof.

18. The compound according to claim 8, wherein
$R^6$ is selected from the group consisting of methoxy, —C(O)$_2$H and —C(O)$_2$—(CH$_2$CH$_3$);
or a pharmaceutically acceptable salt, a stereoisomer, a tautomer, a polymorph, a solvate, an N-oxide, or an isotope-labeled compound thereof.

19. The compound according to claim 9, wherein
both m and n are 1;
or a pharmaceutically acceptable salt, a stereoisomer, a tautomer, a polymorph, a solvate, an N-oxide, or an isotope-labeled compound thereof.

20. The compound according to claim 1, wherein the compound has a structure selected from the group consisting of:

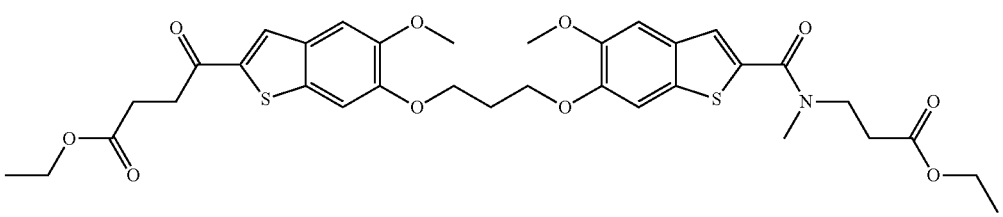

1

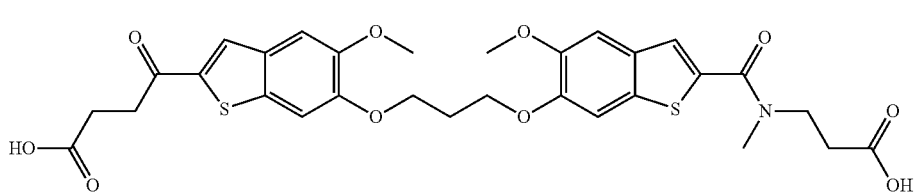

2

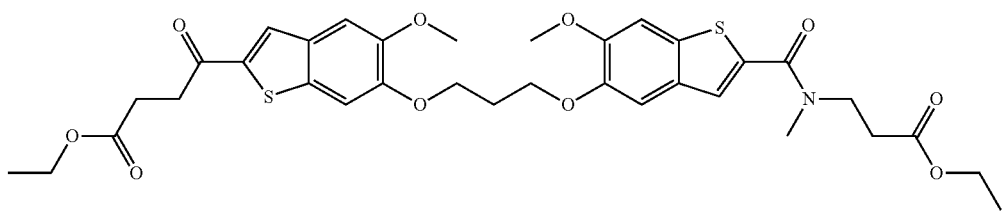

3

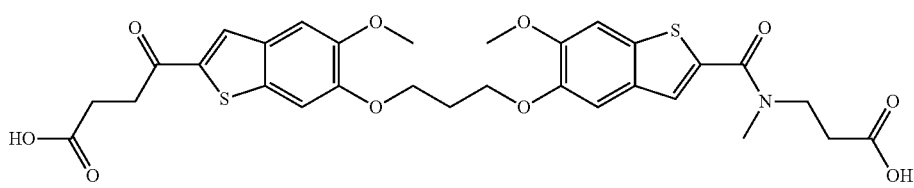

4

-continued
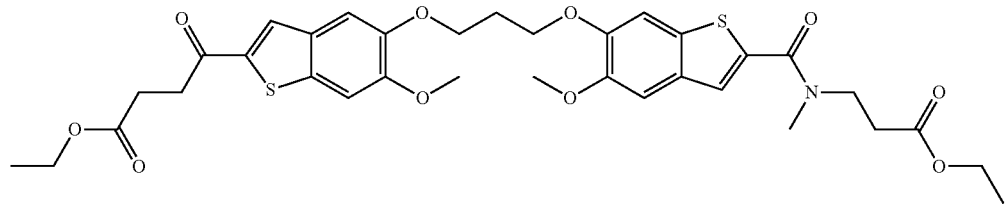
5
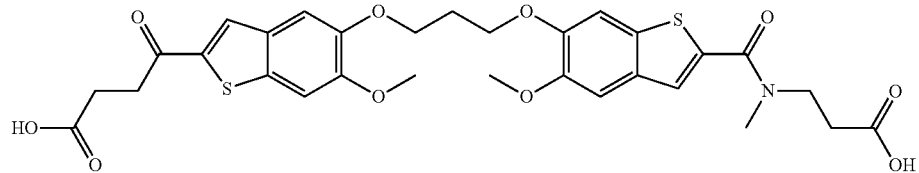
6
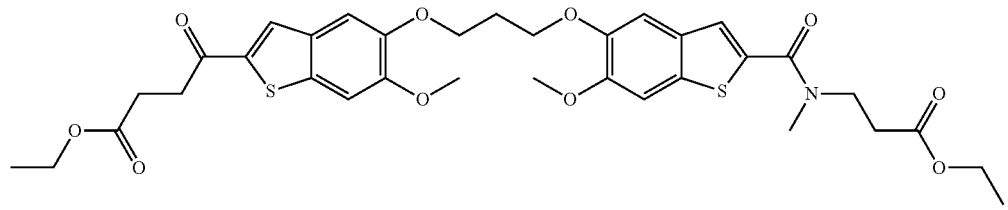
7
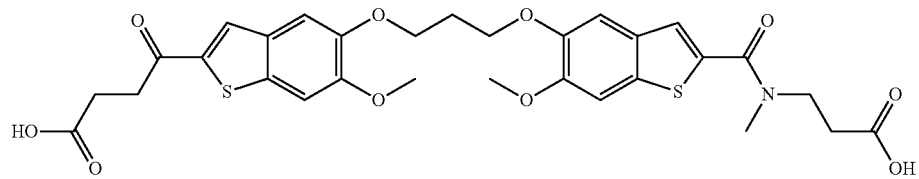
8
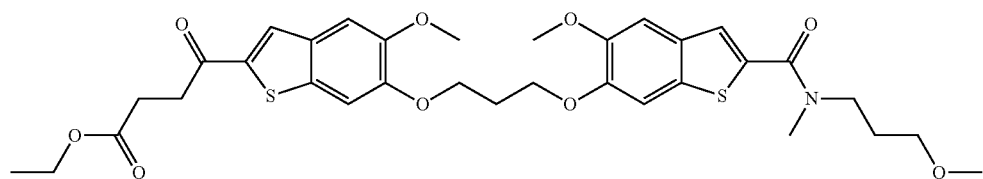
17
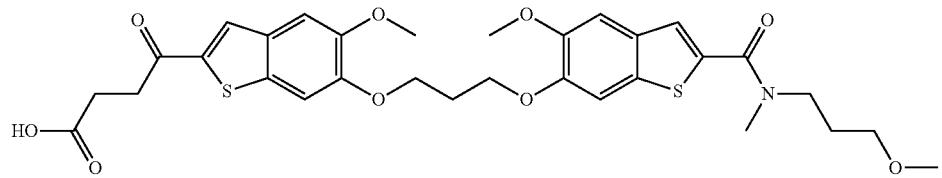
18
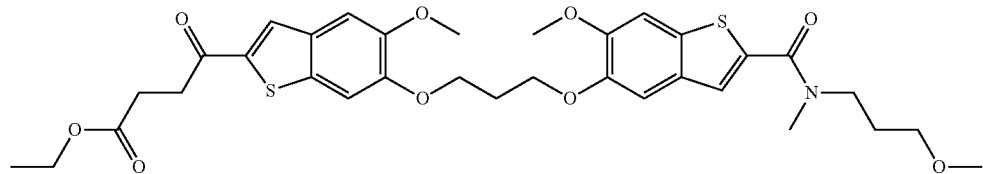
19
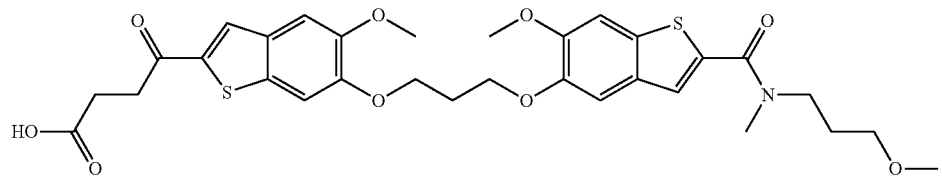
20

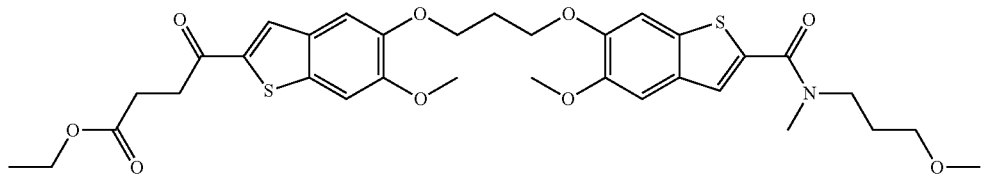

21

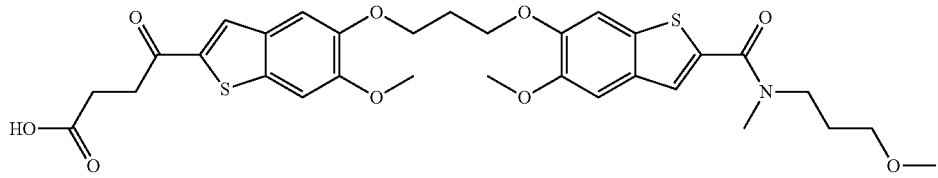

22

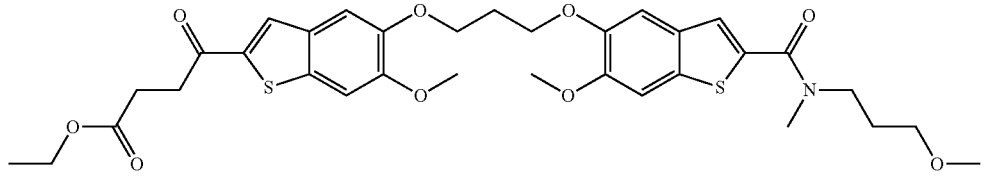

23

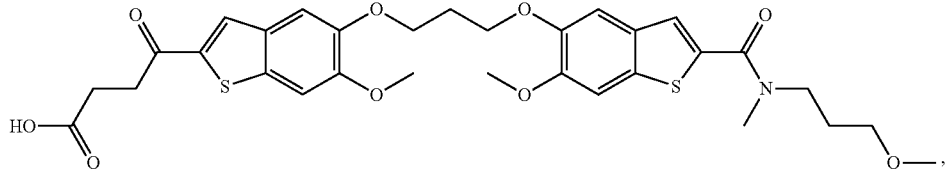

24 or a pharmaceutically acceptable salt, a stereoisomer, a tautomer, a polymorph, a solvate, an N-oxide, or an isotope-labeled compound thereof.

21. A pharmaceutical composition, comprising a prophylactically or therapeutically effective amount of the compound according to claim 1, or a pharmaceutically acceptable salt, a stereoisomer, a tautomer, a polymorph, a solvate, an N-oxide, or an isotope-labeled compound thereof, and one or more pharmaceutically acceptable carriers.

22. A pharmaceutical composition, comprising a prophylactically or therapeutically effective amount of the compound according to claim 10, or a pharmaceutically acceptable salt, a stereoisomer, a tautomer, a polymorph, a solvate, an N-oxide, or an isotope-labeled compound thereof, and one or more pharmaceutically acceptable carriers.

23. A pharmaceutical composition, comprising a prophylactically or therapeutically effective amount of the compound according to claim 20, or a pharmaceutically acceptable salt, a stereoisomer, a tautomer, a polymorph, a solvate, an N-oxide, or an isotope-labeled compound thereof, and one or more pharmaceutically acceptable carriers.

24. A kit, comprising the compound according to claim 1, or a pharmaceutically acceptable salt, a stereoisomer, a tautomer, a polymorph, a solvate, an N-oxide, or an isotope-labeled compound thereof.

25. A method for preparing the compound according to claim 10, comprising the following steps:

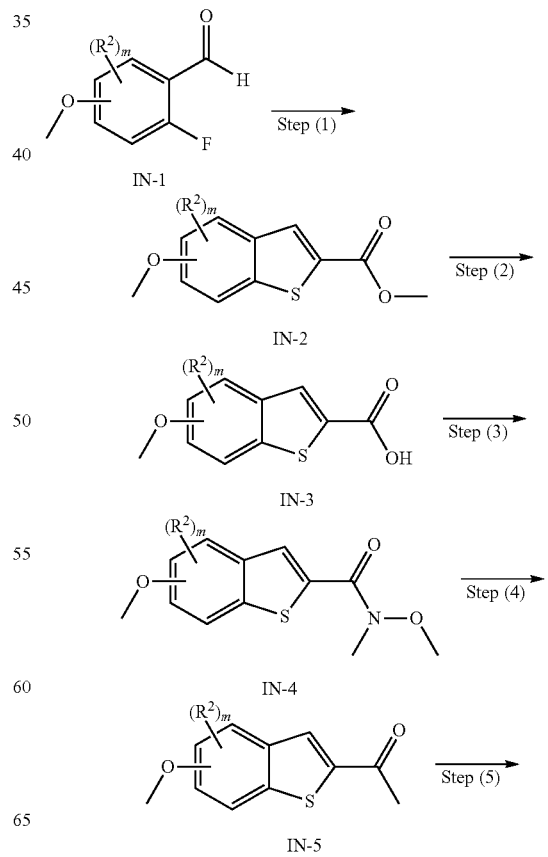

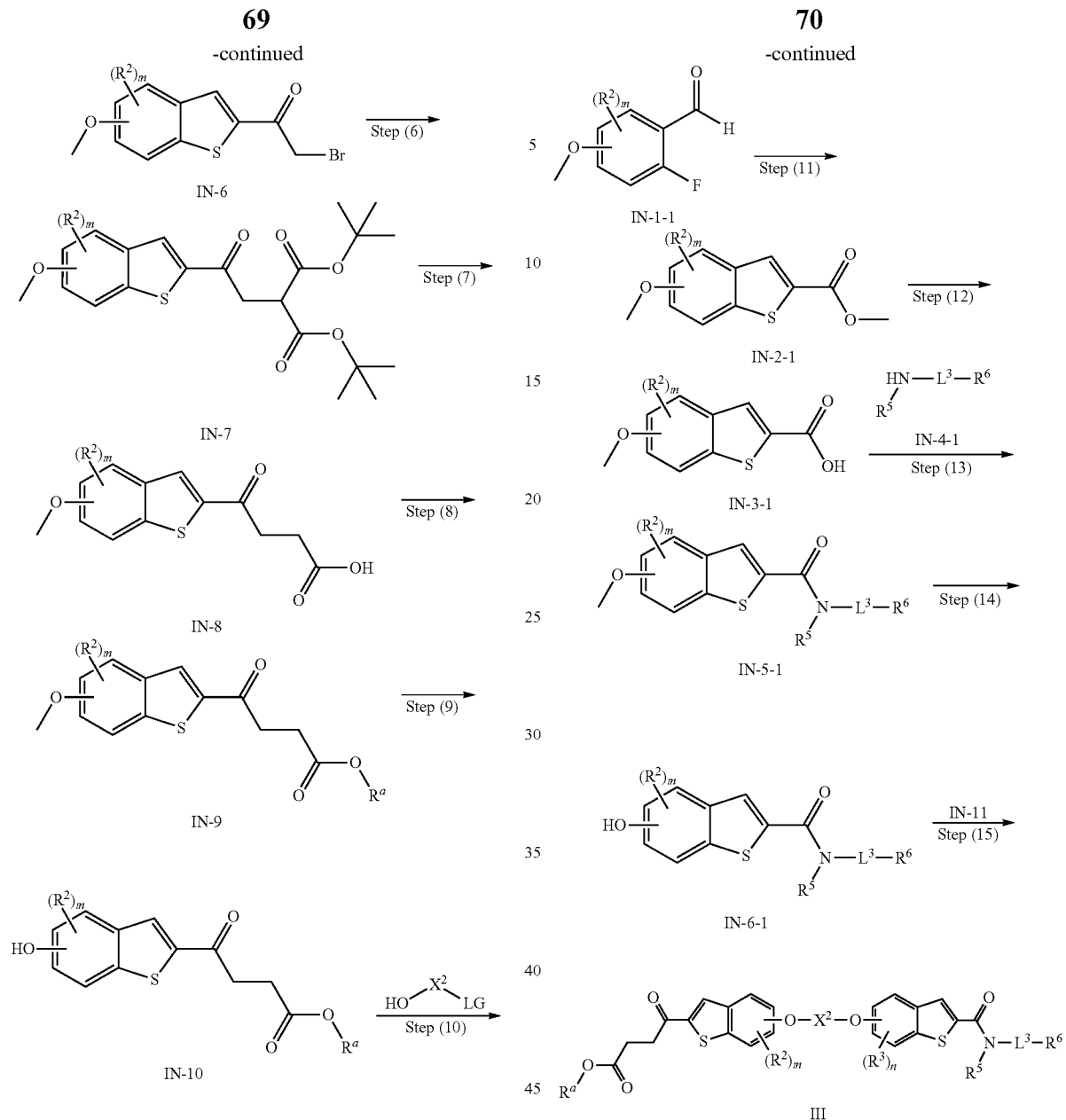
wherein
L³, R², R³, R⁵, R⁶, X², m and n are as defined in claim 14;
Rᵃ is $C_{1-6}$ alkyl; and
LG represents a leaving group, wherein the leaving group includes, but is not limited to, a halogen atom, methanesulfonyloxy, p-toluenesulfonyloxy, and the like.
26. A method for preparing the compound according to claim 11, comprising the following steps:
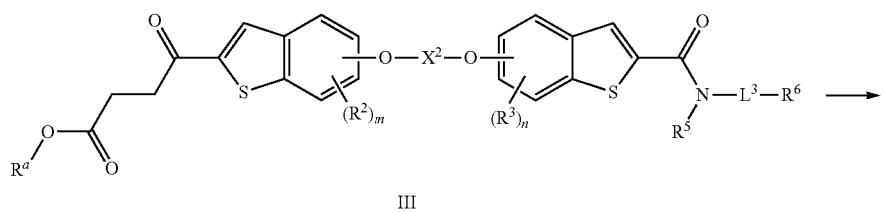

-continued

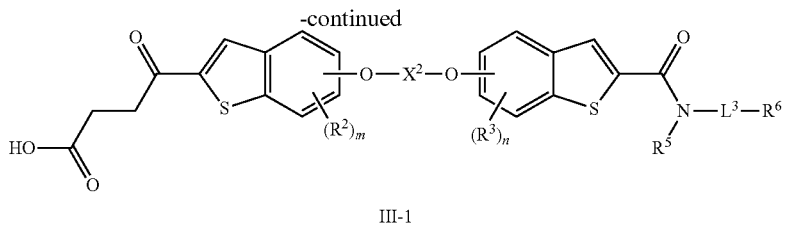

III-1 wherein $L^3, R^2, R^3, R^5, R^6, X^2$, m and n are as defined in claim 11; and $R^a$ is $C_{1-6}$ alkyl.

27. A method for the prophylaxis or treatment of a STING-mediated disease, comprising administering to a subject in need thereof a prophylactically or therapeutically effective amount of the compound according to claim 1, or a pharmaceutically acceptable salt, a stereoisomer, a tautomer, a polymorph, a solvate, an N-oxide, or an isotope-labeled compound thereof.

28. The method of claim 27, wherein the compound is administered via an oral, intravenous, intraarterial, subcutaneous, intraperitoneal, intramuscular or transdermal route.

29. The method of claim 27, wherein the STING-mediated disease is a tumor.

* * * * *